(12) United States Patent
Doranz

(10) Patent No.: US 8,377,691 B2
(45) Date of Patent: Feb. 19, 2013

(54) LIPOPARTICLES COMPRISING ION CHANNELS, METHODS OF MAKING AND USING THE SAME

(75) Inventor: Benjamin J. Doranz, Drexel Hill, PA (US)

(73) Assignee: Integral Molecular, Inc., Philadelphia, PA (US)

( * ) Notice: Subject to any disclaimer, the term of this patent is extended or adjusted under 35 U.S.C. 154(b) by 1509 days.

(21) Appl. No.: 11/698,607

(22) Filed: Jan. 25, 2007

(65) Prior Publication Data

US 2007/0225227 A1 Sep. 27, 2007

Related U.S. Application Data

(60) Provisional application No. 60/762,798, filed on Jan. 26, 2006.

(51) Int. Cl.
*G01N 33/53* (2006.01)
(52) U.S. Cl. ........................................................ 435/375
(58) Field of Classification Search ........................ None
See application file for complete search history.

(56) References Cited

U.S. PATENT DOCUMENTS

| | | | |
|---|---|---|---|
| 7,763,258 B2 | 7/2010 | Doms et al. | |
| 8,158,130 B2 | 4/2012 | Doms et al. | |
| 2005/0009186 A1* | 1/2005 | Bebbington et al. | 435/456 |
| 2005/0123563 A1* | 6/2005 | Doranz et al. | 424/204.1 |
| 2007/0191418 A1* | 8/2007 | Vohra et al. | 514/292 |
| 2009/0209029 A1* | 8/2009 | Guia et al. | 435/288.7 |
| 2012/0195882 A1 | 8/2012 | Doms et al. | |

OTHER PUBLICATIONS

Mould et al. (2000) J. Biol. Chem. 275: 31038-31050.*
Adamson CS. et al. Erratum to "A block in virus-like particle maturation following assembly of murine leukaemia virus in insect cells" [Virology 314 (2003) 488A96]in Virology. Dec. 20, 2003;317(2):384-6.
Kim, J-S. et al. "Development of a packaging cell line for propagation of replication-deficient adenovirus vector" Experimental and Molecular Medicine, vol. 33, No. 3, 145-149, Sep. 2001.
Morikawa Y. et al. "In vitro processing of human immunodeficiency virus type 1 Gag virus-like particles" Virology, Jul. 5, 2000;272(2):366-74.
Chen, "Influenza Virus Hemagglutinin and Neuraminidase, but Not the Matrix Protein, Are Required for Assembly and Budding of Plasmid-Derived Virus-Like Particles" J. Virology, 81(13):7111-7123, 2007.
Adamson CS, et al. "A block in virus-like particle maturation following assembly of murine leukaemia virus in insect cells." Virology. Sep. 30, 2003;314(2):488-96.
Mills K. et al "HIV p24-specific helper T cell clones from immunized primates recognize highly conserved regions of HIV-1". J Immunol. Mar. 1, 1990;144(5):1677-83.
Hoffman TL. et al "A biosensor assay for studying ligand-membrane receptor interactions: Binding of antibodies and HIV-1 Env to chemokine receptors" PNAS 2000, 97: 11215-11220.
Seifert R. et al"GPCR-G alpha fusion proteins: molecular analysis of receptor-G-protein coupling". Trends Pharmacol Sci. Sep. 1999; 20(9):383-9).
Milligan G et al. "Chimaeric G alpha proteins: their potential use in drug discovery". Trends Pharmacol Sci. Mar. 1999;20(3):118-424.
Martinez X. et al. "CD4-Independent protective cytotoxic T cells induced in early life by a non-replicative delicery system based on virus-like particles" Virology 305, 428-435 (2003).
Non-final office action issued on Mar. 28, 2007 in U.S. Appl. No. 10/901,399.
Non-final office action issued on Aug. 6, 2008 in U.S. Appl. No. 10/901,399.
Non-final office action issued on Jan. 6, 2010 in U.S. Appl. No. 10/901,399.
Final office action issued on Jan. 18, 2007 in U.S. Appl. No. 10/901,399.
Final office action issued on Jul. 22, 2009 in U.S. Appl. No. 10/901,399.
Final office action issued on Aug. 17, 2010 in U.S. Appl. No. 10/901,399.
Advisory Action issued on Oct. 29, 2010 in U.S. Appl. No. 10/901,399.
Supplemental Advisory Action issued on Dec. 7, 2010 in U.S. Appl. No. 10/901,399.
McEwen DP et a. "Fluorescent BODIPY-GTP analogs: real-time measurement of nucleotide binding to G proteins". Anal Biochem. Apr. 1, 2001;291(1):109-17.
U.S. Appl. No. 09/006,678, filed Jan. 13, 1998, now abandoned.

* cited by examiner

*Primary Examiner* — Michael Pak
(74) *Attorney, Agent, or Firm* — Pepper Hamilton LLP

(57) ABSTRACT

The present invention relates to the use of lipoparticles, virus-like particles, and viruses. The present invention also relates to testing ion channel function and modulators of ion channels.

21 Claims, 32 Drawing Sheets

Figure 1.
A. Lipoparticle Titration
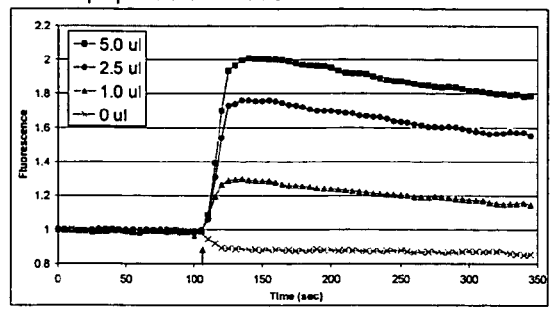
B. Dependence on Valinomycin
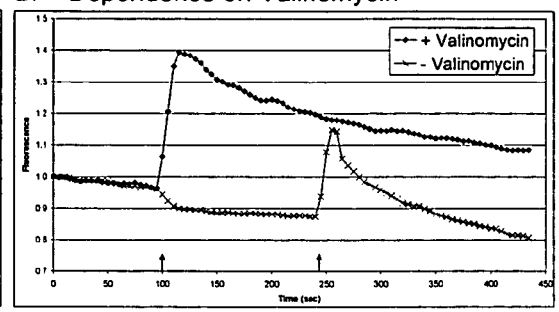
C. K⁺ Titration
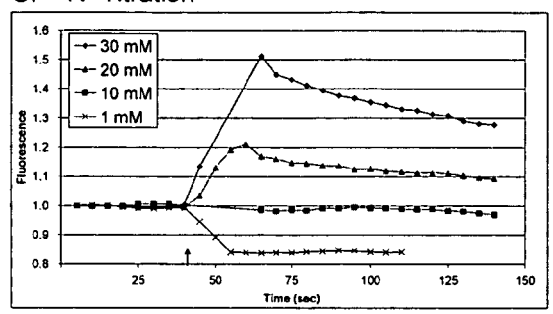
D. Control Treatments
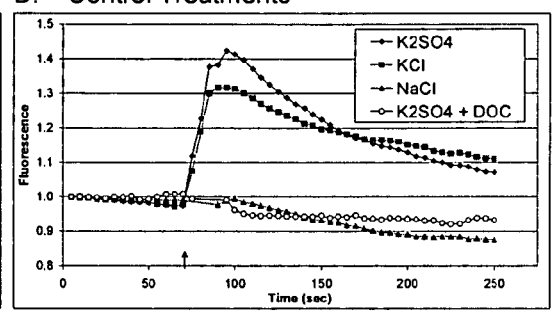

Figure 3.
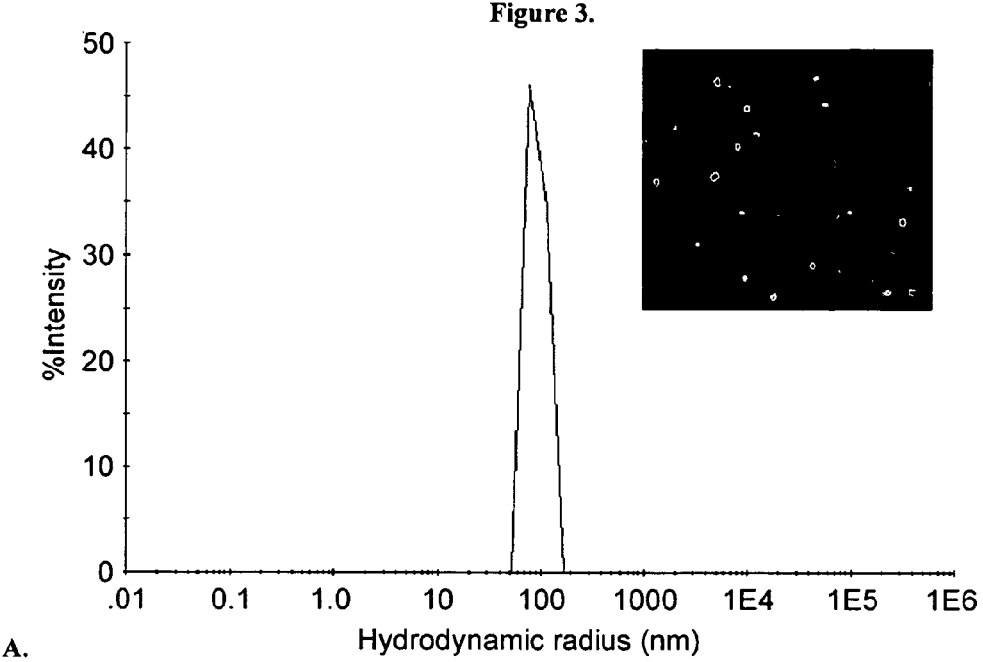
A.
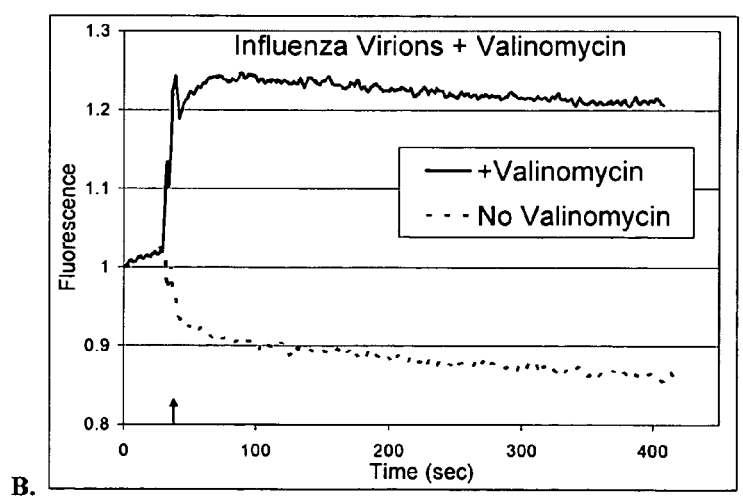
B.

Figure 7.
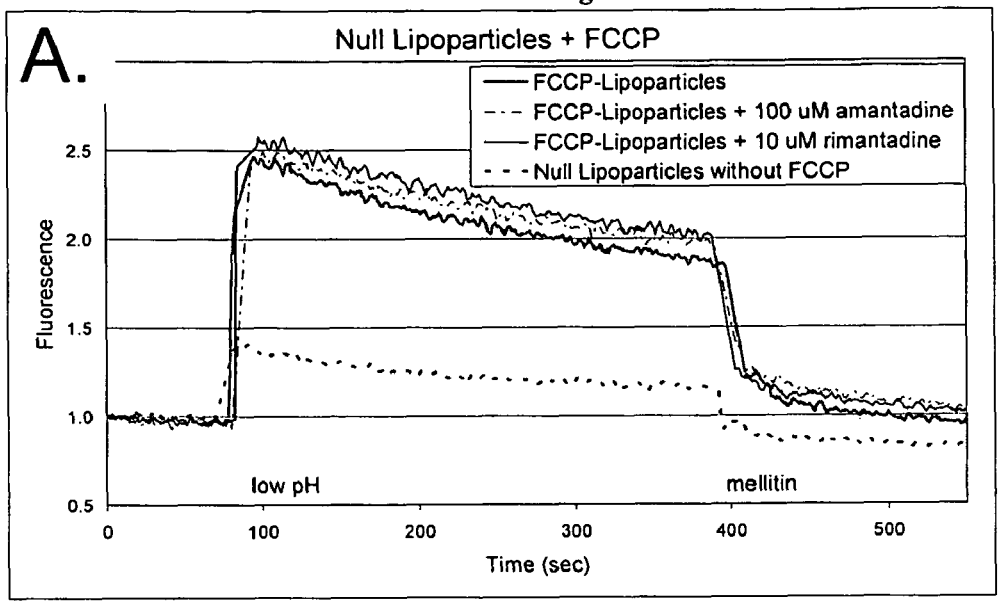
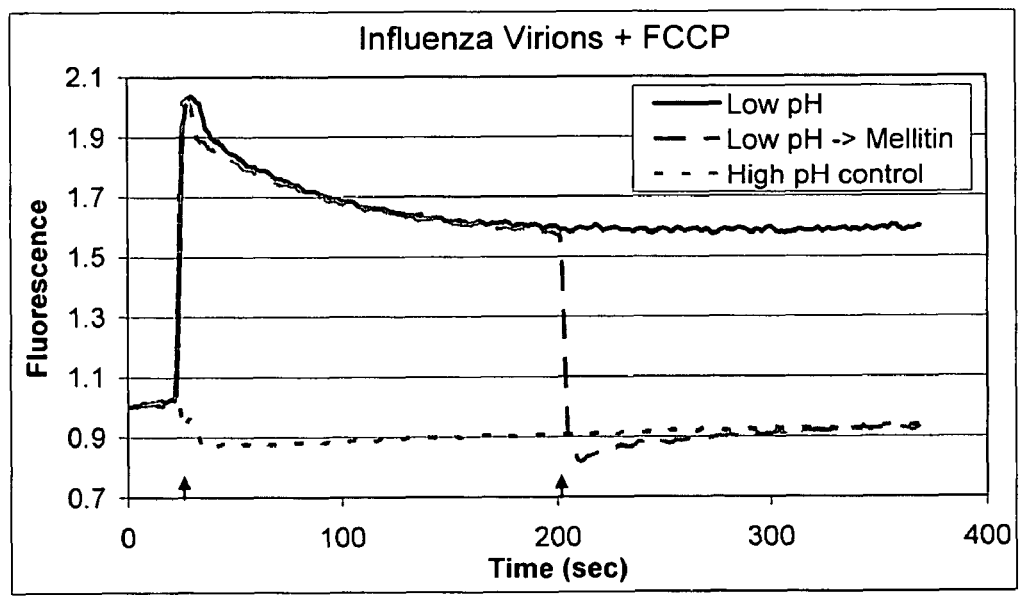

Figure 8.
A.
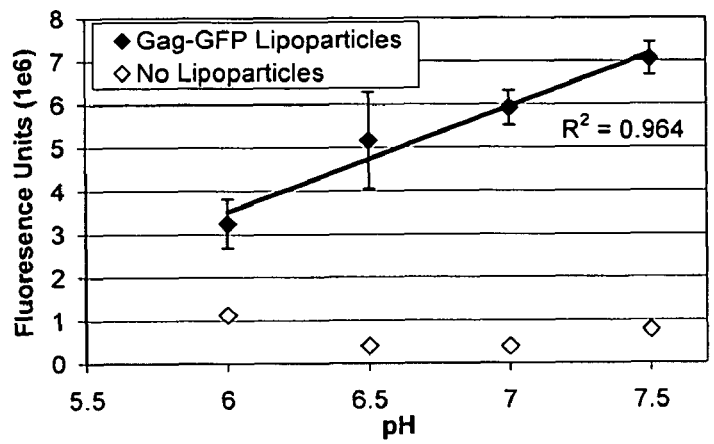
B.
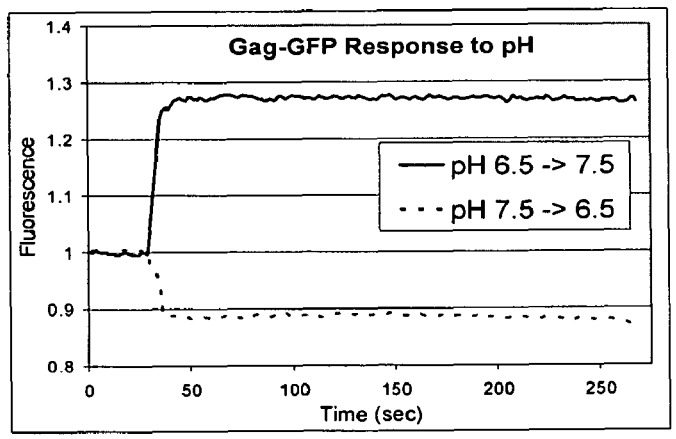
C.
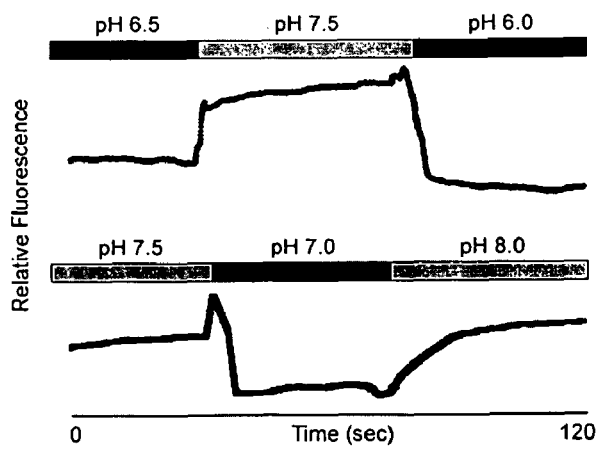

Figure 15
A. Titration of FMP dye
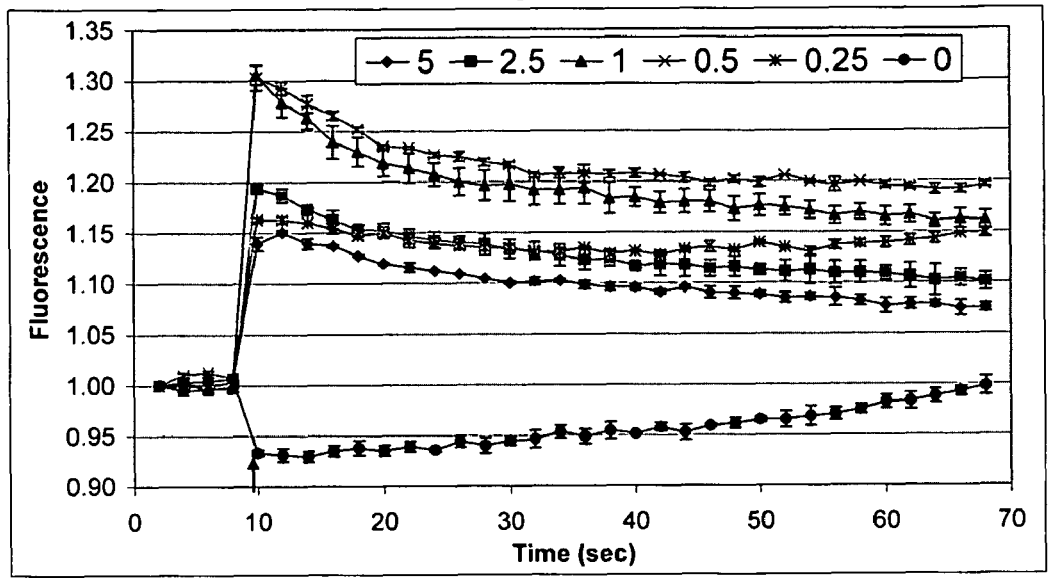
B. Titration of Lipoparticles
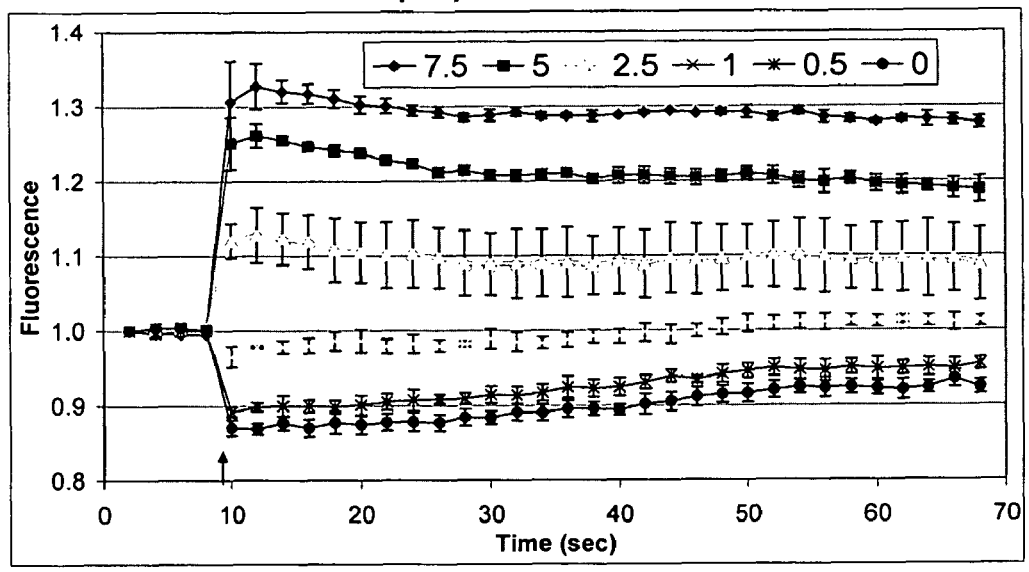

C.

Figure 18
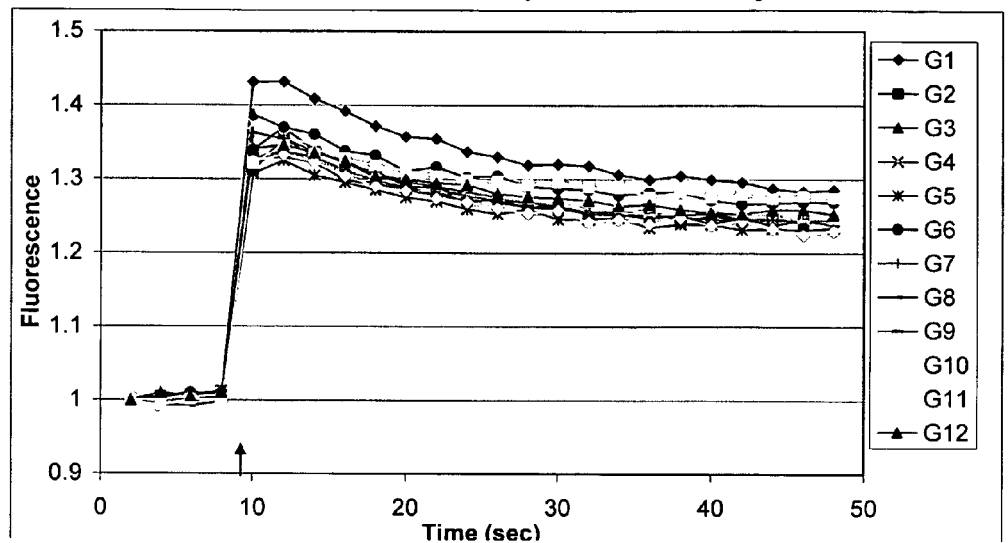
A. Positive Control Reproducibility
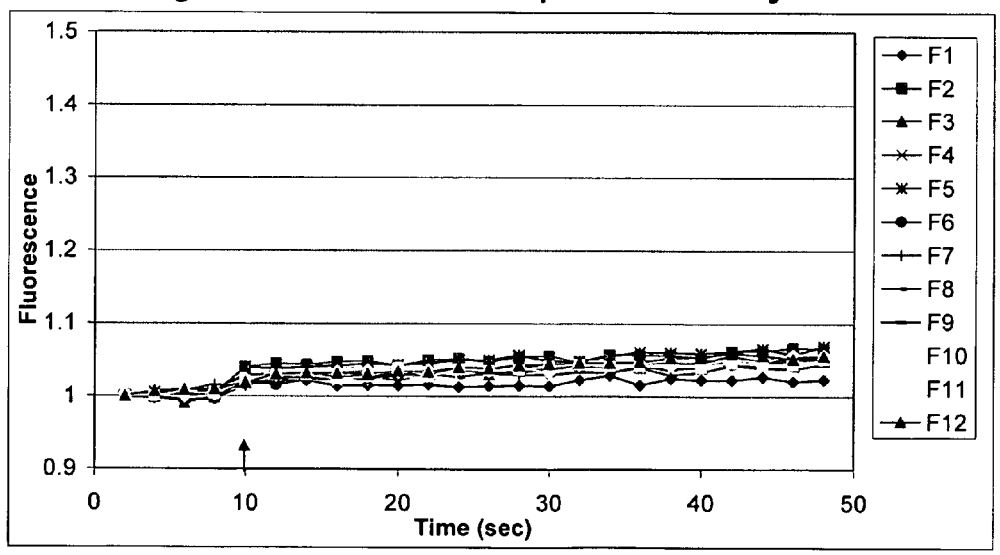
B. Negative Control Reproducibility Figure 19.
A. Detection on FlexStationII-384
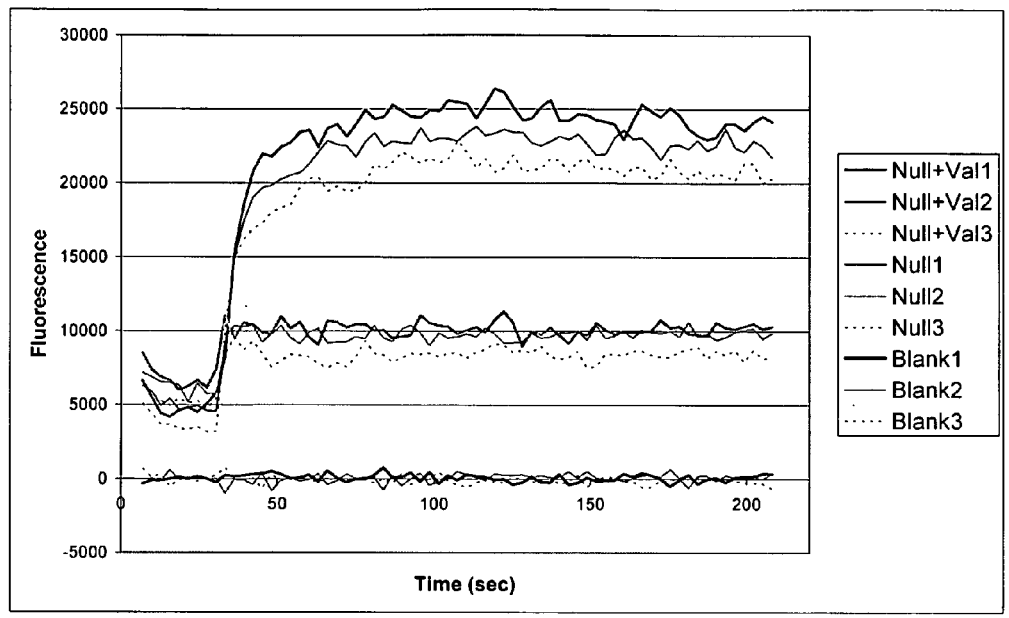
B. Detection on FLIPR-Tetra
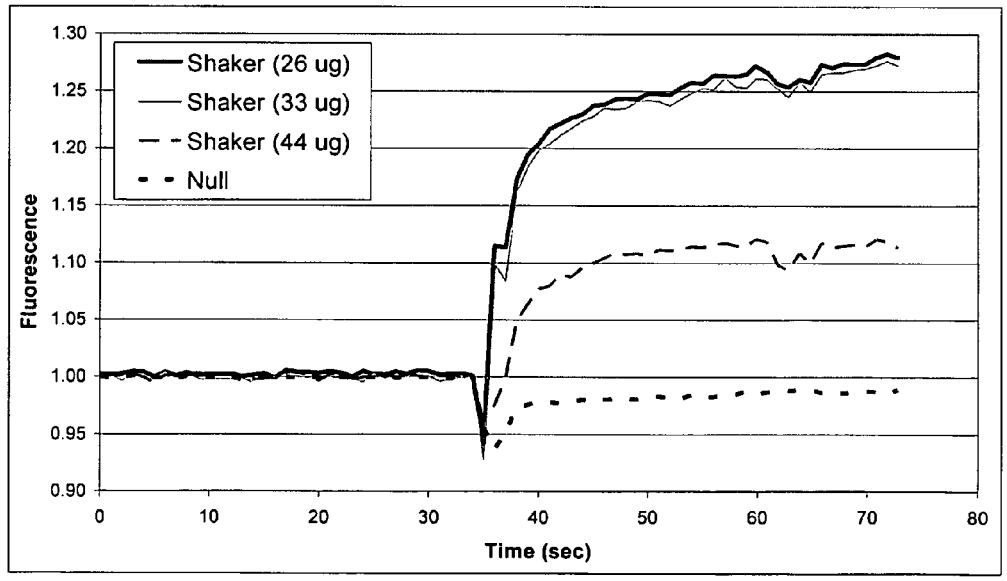

Figure 29.
A.
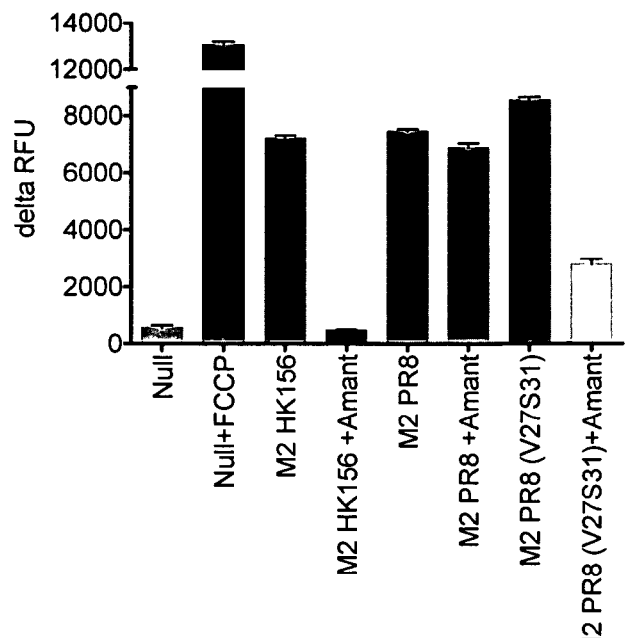
B.
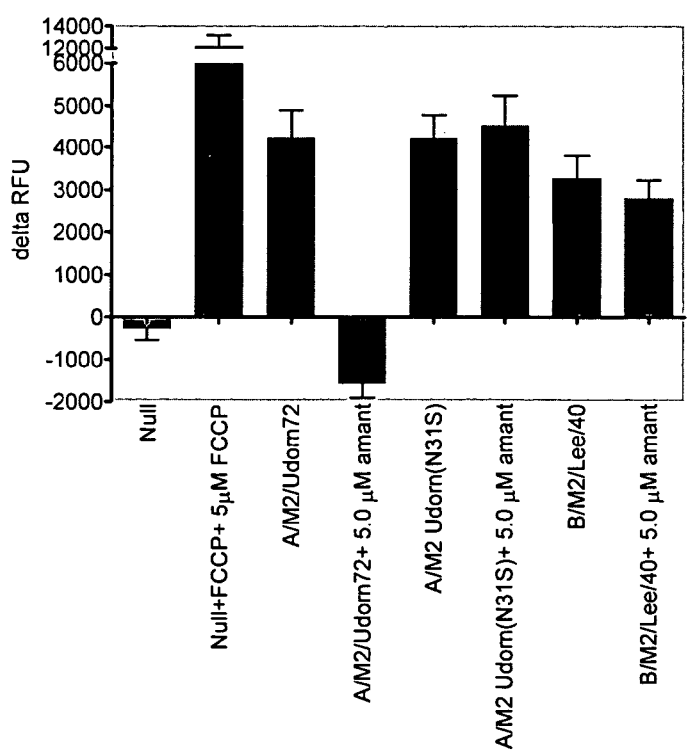

LIPOPARTICLES COMPRISING ION CHANNELS, METHODS OF MAKING AND USING THE SAME

CROSS-REFERENCE TO RELATED APPLICATIONS

This application claims priority under 35 U.S.C. 119(e) to U.S. Provisional Application Ser. No. 60/762,798, filed Jan. 26, 2006, and is related to U.S. Provisional Application Ser. No. 60/491,477, filed Jul. 30, 2003, U.S. Provisional Application Ser. No. 60/491,633, filed Jul. 30, 2003, U.S. Provisional Application Ser. No. 60/498,755, filed Aug. 29, 2003, U.S. Provisional Application Ser. No. 60/502,478, filed Sep. 12, 2003, U.S. Provisional Application Ser. No. 60/509,677, filed Oct. 7, 2003, U.S. Provisional Application Ser. No. 60/509,608, filed Oct. 7, 2003, and U.S. Provisional Application Ser. No. 60/509,575, filed Oct. 7, 2003, U.S. patent application Ser. No. 10/901,399, filed Jul. 28, 2004, which published as U.S. Patent Application Publication 20050123563, each of which is herein incorporated by reference in its entirety.

GOVERNMENT SUPPORT

This invention was made with U.S. Government support (NIH Grant Nos. GM68322 and A1071337) and the U.S. Government may therefore have certain rights in the invention.

BACKGROUND OF THE INVENTION

Membrane potential is an electrical potential difference across an impermeable lipid bilayer (reviewed in (Hille (2001))). Membrane potentials occur across the plasma membrane of most living prokaryotic and eukaryotic cells, as well as across the membranes of some organelles such as chloroplasts and mitochondria. The cell's membrane potential results from the active translocation of ions (by 'pumps') between the extracellular fluid and the cytoplasm, generating electrochemical concentration gradients along which these ions then have the potential to flow. By selectively regulating the flow of ions (often sodium and potassium) down these gradients, ion channels are the primary effectors of electrophysiological events that mediate cell signaling, development, differentiation of function, and pathology. The membrane potential of a typical resting cell is −70 mV (the cytoplasm being electrically negative with respect to the extracellular fluid). Changes in this membrane potential are usually effected by the coordinated action of many types of ion channels. Changes in membrane potential in the positive direction (i.e. resulting in a net positive intracellular charge) are referred to as depolarization. Changes in the negative direction (i.e. resulting in a net negative intracellular charge) are referred to as hyperpolarization.

Ion channels are membrane-bound proteins that control the flow of ions across biological membranes. There are about 400 recognized ion channel genes in the human genome (Venter, et al. (2001), Science, 291:1304-51), encoding proteins specific for potassium ($K^+$), sodium ($Na^+$), chloride ($Cl^-$), calcium ($Ca^{2+}$), and hydrogen ($H^+$) translocation. Many ion channels are capable of transporting more than one ion species. Potassium ion ($K^+$) channels have been particularly well studied due to their primary importance in excitable cells (Ford, et al. (2002), Prog Drug Res, 58:133-168)). A number of toxins are known to bind specifically to K-channels, a handful of K-channels have been crystallized, and a variety of K-channels with various regulatory features have been defined and characterized.

Ion channels are responsible for a variety of essential cellular processes throughout the body, most notably (although by no means exclusively) the generation of action potential in excitable tissues (muscle and nerve). In cardiac ventricular cells, for example, depolarization is achieved by the inward-translocation of $Na^+$ by cardiac sodium channels (e.g. SCN5a), while hyperpolarization involves a diverse number of potassium channels, including the KCNQ1 and hERG $K^+$ channels. The dysfunction of ion channels is responsible for many common disorders such as cardiac arrhythmias, neurological and behavioral diseases, diabetes, hypertension, angina pectoris, and cystic fibrosis. In addition to being important molecular targets for treating human disease, ion channels are also a major cause of off-target adverse effects and poor drug safety. For example, more than 50% of all drug withdrawals from the market since 1998 have been due to adverse and unpredicted effects on the functions of the hERG $K^+$ channel. For these reasons, high-throughput systems that facilitate the screening of compounds against ion channels are of significant interest to the pharmaceutical industry, both for monitoring drug safety as well as for developing disease therapeutics.

About 15% of the top 100 best-selling drugs target ion channels. New drugs that target ion channels are therefore highly sought after by pharmaceutical companies. However, traditional methods of discovering ion channel drugs have consistently failed to identify novel ion channel inhibitors. Ion channels therefore remain one of the most promising, but underexploited, molecular targets in drug discovery.

Among the most important ion channels needed for High Throughput Screening ("HTS") are those involved in the pathogenesis of cardiac arrhythmias. More than 300,000 deaths each year are attributed to ventricular tachyarrhythmia, the most dangerous form of cardiac arrhythmia. Among the ion channels important for regulating the ventricular action potential are KCNQ1, hERG, SCN5a, and their beta-subunits minK and MiRP1 (reviewed in (Keating, et al. (2001), Cell, 104:569-80)). Collectively, these five proteins are involved in the pathogenesis of over 95% of inherited cardiac arrhythmias (including long QT syndrome (LQT), familial ventricular fibrillation, and Jervell and Lange-Nielsen syndrome). KCNQ1 and hERG alone are responsible for 87% of inherited LQT. Although familial LQT is relatively rare, linkage of these genes to LQT validates them as targets to treat acquired forms of the disease.

Perhaps of broader significance, off-target inhibition of the $I_{Kr}$ current (hERG+MiRP1) is responsible for nearly all drug-induced LQT (Keating, et al. (2001), Cell, 104:569-80), and has been responsible for 50% of all drug withdrawals from the market since 1998. Cross-screening for hERG reactivity is now highly recommended by the FDA for all drugs, and is being integrated into the drug-development process of most pharmaceutical companies.

Many FDA-approved drugs that inhibit ion channels preferentially bind open or inactivated states of their target channels, often with 1-2 orders of magnitude greater affinity. Drug targeting to particular states of an ion channel can involve open-state block, inactivated-state block, voltage-dependent block, and use-dependent block (reviewed in (Birch, et al. (2004), Drug Discov Today, 9:410-418)). The "open" state of an ion channel also includes certain inactivated states in which the channel is in a non-conducting but open conformation. Examples include nearly all drugs that exert effects on the hERG $K^+$ channel (Kamiya, et al. (2001), Mol Pharmacol, 60:244-53, Mitcheson, et al. (2000), Proc Natl Acad Sci USA, 97:12329-33, Sanguinetti, et al. (2005), Trends Pharmacol Sci, 26:119-24), most $Na_v$-channel drugs (particularly anticonvulsants and anesthetics) (Yang, et al. (2002), Mol Pharmacol, 62:1228-37), the alkyl ammonium class of ion channel inhibitors (e.g. TEA), and a large number of $Ca^{2+}$ channel modulators. However, most ion channels presented by cells during a typical HTS screen are in the closed state (in a typical cell-based HTS, the channels are simply expressed on the cell surface, a resting state in which most ion channels will be closed). Thus, potential inhibitors that require an open state to bind may not be easily detected in a typical cell-based screen. The ability to screen for compounds that preferentially bind different ion channel conformations could greatly facilitate the identification of novel drugs.

The 97 amino acid influenza A M2 protein is the best-characterized of a growing number of putative ion channels encoded by different viruses (reviewed in (Kelly, et al. (2003), FEBS Lett, 552:61-7). This pH-activated $H^+$ ion channel functions as a homotetramer, its gating properties and specificity have been well-studied, and it is an established determinant of influenza pathogenicity and infectivity (reviewed in (Fischer, et al. (2002), Biochim Biophys Acta, 1561:27-45, Pinto, et al. (2004), FEBS Lett, 560:1-2)). M2 is expressed in large quantities on the plasma membrane of infected cells, from where it is incorporated into the viral membrane during virion budding. As influenza particles enter new target cells by endocytosis, they become exposed to low pH within endosomes. The low pH triggers M2 gating which is believed to allow $H^+$ to enter the virus and lower the internal viral pH. Acidification of the virion interior is necessary to facilitate release of viral nucleic acid and nucleocapsid protein (together, the 'RNP' complex) from the M1 structural protein, a pre-requisite for nuclear migration of the viral genome. The M2 protein also has a separate function late in viral assembly, neutralizing Golgi pH to ensure that the viral envelope (HA) is not prematurely activated.

M2 is conserved in all strains of influenza, and artificially engineered M2-deficient strains are attenuated (Takeda, et al. (2002), J Virol, 76:1391-9, Watanabe, et al. (2001), J Virol, 75:5656-62), indicating the vital role of this protein in viral pathogenicity. Two of the four FDA-approved influenza therapeutics target the M2 ion channel, validating it as a molecular target for the treatment of influenza infection. FDA-approved influenza drugs (non-vaccines) include amantadine (α-M2, 1976), rimantadine (α-M2, 1993), zanamivir (α-NA, 1999), and oseltamivir (α-NA, 1999). Amantadine, and the structurally-related rimantadine, inhibit viral entry and assembly, and are the only FDA-approved influenza drugs for treatment and prophylaxis. Influenza B and C possess M2 proteins that likely play similar roles to that of influenza A M2, but these targets are not yet completely validated (in part because inhibitors do not yet exist).

The need for new, broad-spectrum inhibitors of M2 is urgent, as influenza strains resistant to existing M2 drugs are becoming increasingly prevalent (Abed, et al. (2005), Antimicrob Agents Chemother, 49:556-9). However, no new M2 drugs have been developed in over a decade (and the last, rimantadine, is a structural derivative of amantadine), in part due to the difficulty of screening for new M2 inhibitors. Ion channels in general are among the most difficult proteins to manipulate for HTS. The primary strategy for detecting M2 ion channel activity and its inhibition employs patch clamp of cells (mammalian or oocyte). Both the patch clamp technique and the use of cell expression vehicles are poorly suited for HTS of M2 inhibitors.

A number of other putative viral ion channels, including influenza B M2 and NB, influenza C M2, HIV-1 Vpu, and Vpr, Chlorella Kcv, Paramyxovirus SH, and rhinovirus 3AB, possess potential ion conducting activities (reviewed in (Fischer, et al. (2002), Biochim Biophys Acta, 1561:27-45, Lamb, et al. (1997), Virology, 229:1-11)). However, their contributions to viral entry and replication are largely unknown. A confluence of indirect evidence supports the role of some of these proteins (particularly BM2, CM2, and Vpu) in the viral lifecycle, but has been inconclusive, unavailable, or contradictory regarding others. For example, the NB protein is similar in some respects to M2 (NB is a 100 amino acid single-TM protein incorporated into influenza B virions that can, if reconstituted into lipid bilayers, demonstrate ion conducting activity (Fischer, et al. (2001), Eur Biophys J, 30:416-20, Sunstrom, et al. (1996), J Membr Biol, 150:127-32)), but its function as an ion channel within the virus has been highly controversial (Lamb, et al. (1997), Virology, 229:1-11, Mould, et al. (2003), Dev Cell, 5:175-84). The uncertainties of indirect measurement have hindered the development of viral ion channels as targets for the control of infection, and primarily exist because methods of studying the function of viral ion channels directly within their native virus structures have been unavailable. New methods for identifying viral ion channels and understanding their role in viral infection could enable a number of new questions to be asked about the function of the proteins within the viral structure and allow new possibilities for anti-viral drug development.

The traditional method for measuring membrane potential involves directly inserting glass microelectrodes into or onto isolated cells (patch clamp) to directly measure the difference in electrical potential across the cell membrane. Although it is a very powerful technique, this is usually a cumbersome and low-throughput approach to monitoring ion channel activity. Recently, automated planar patch-clamp systems have increased the ability to perform patch-clamps from about a dozen per day by hand to several hundred or several thousand by machine (Xu, et al. (2003), Assay Drug Dev Technol, 1:675-84). Despite its advances, however, planar patch-clamp (50-3,000 assays per day with an assay failure rate of >25%) is not being used for high-throughput screening (current high-throughput requirements are 100,000+ screens per day with a failure rate of <<1%). Automated patch-clamp systems are also expensive and require specialized technical expertise and attention. In addition, taking measurements from single cells increases error due to biological variation, resulting in unacceptable variability compared to required HTS standards (Sorota, et al. (2005), Assay Drug Dev Technol, 3:47-57). For these reasons, planar patch-clamp is primarily being used as a secondary screen for validating and characterizing lead compounds discovered by other techniques.

A high-throughput alternative to direct electrophysiological measurement techniques is the use of fluorescent probes that respond to changes in electrical membrane potential (reviewed in (Haugland (2003), Plasek, et al. (1996), J of Photochemistry and Photobiology, 33:101-124, Smith (1990), Biochim Biophys Acta, 1016:1-28)). Membrane potential-sensitive fluorescent probes are lipophilic dyes that associate with the lipid bilayer and change their spectral properties in response to membrane potential changes across that bilayer. The dyes are classified either as "slow" or "fast" depending on how they respond to the re-distribution of charges across the membrane. Slow dyes migrate to the opposite side of the membrane over seconds or minutes, while fast dyes respond within milliseconds by flipping their orientation within the membrane. Membrane potential-sensitive fluorescent probes were first employed in the 1970s, and have since evolved in capability, speed of response, and sensitivity (Cohen, et al.

(1978), Rev Physiol Biochem Pharmacol, 83:35-88, Plasek, et al. (1996), J of Photochemistry and Photobiology, 33:101-124, Smith (1990), Biochim Biophys Acta, 1016:1-28, Wolff, et al. (2003), J Biomol Screen, 8:533-43, Zochowski, et al. (2000), Biol Bull, 198:1-21). For example, many membrane potential probes can now be measured "ratiometrically" to provide a more stable baseline (independent of dye loading and leakage) and to increase signal-to-noise values (up to 10-fold compared with single wavelength measurements) (Haugland (2003), Montana, et al. (1989), Biochemistry, 28:4536-4539). Many lipophilic membrane potential dyes partition quickly into lipid bilayer membranes, and have little or no fluorescence in aqueous solution (and therefore excess dye need not be washed away after loading into membranes). Membrane potential-sensitive dyes have been used to monitor membrane potential in eukaryotic cells, prokaryotic cells, and lipid vesicles, but have not been used previously to measure membrane potential in viral structures. Several popular commercial devices rely on membrane potential probes to enable high-throughput screening of ion channel activity within cells, including Panvera/Invitrogen's VIPR platform and Molecular Device's FLIPR system (Gonzalez, et al. (1997), Chem Biol, 4:269-77, Larson (2003), Discovery HTS, 1:5-6, Whiteaker, et al. (2001), J Biomol Screen, 6:305-12).

There are many examples of membrane potential dyes. Molecular Devices' FMP dye, consists of the DiSBAC(1)3 voltage-sensitive dye combined with a quencher, Direct Blue 71, that improves signal-to-noise (Baxter, et al. (2002), J Biomol Screen, 7:79-85, Whiteaker, et al. (2001), J Biomol Screen, 6:305-12, Wolff, et al. (2003), J Biomol Screen, 8:533-43)(U.S. Pat. No. 6,852,504) The commercially available FMP dye has been optimized for cellular applications. For many years, DiSC3(5) was considered to be the gold-standard for membrane potential assays due its high sensitivity (50-80% per 100 mV, the highest of all cyanine dyes, (Plasek, et al. (1996), J of Photochemistry and Photobiology, 33:101-124)). However, this high signal is achieved by a concomitant high accumulation of the dye in cells that reduces cell health and can cause cell death, precluding its use for many applications. Its high sensitivity, its ability to be measured ratiometrically (Haugland (2003), Montana, et al. (1989), Biochemistry, 28:4536-4539), and the lack of toxicity restrictions in lipoparticles, make DiSC3(5) an excellent choice for use in lipoparticles. RH 421 has the highest sensitivity of the "fast" membrane potential probes, greater than 20% fluorescence change per 100 mV (Haugland (2003)), making it an excellent choice. Its use has been restricted by cellular toxicity and cell type variability, both of which are overcome using lipoparticles. The ANEPPS dyes (di-4-ANEPPS, di-8-ANEPPS, and related derivatives) exhibit good photostability, a very fast response (<1 msec), and a uniform 10% change in fluorescence intensity per 100 mV (Haugland (2003), Rohr, et al. (1994), Biophysical Journal, 67:1301-1315, Zochowski, et al. (2000), Biol Bull, 198:1-21). The dye is essentially nonfluorescent in aqueous solution but has an absorption/emission maxima of 467/631 nm, which can be measured ratiometrically (dual excitation at 440/530).

Membrane proteins, including ion channels and G protein-coupled receptors (GPCRs), can be incorporated into viruses and virus-like particles (VLPs). We have previously incorporated both ion channels and GPCRs into MLV-based VLPs ((Doranz, et al. (2004)) U.S. patent application Ser. No. 10/901,399). Similarly, GPCRs have been incorporated into baculovirus and used for various assays (Bouvier, et al. (1998), Curr Opin Biotechnol, 9:522-7, Klaassen, et al. (1999), Biochem J, 342 (Pt 2):293-300, Loisel, et al. (1997), Nat Biotechnol, 15:1300-4, Masuda, et al. (2003), J Biol Chem, 278:24552-62).

Thus there is a need for methods and compositions to study ion channels and for screens to identify compounds that modulate the activity of ion channels. The present invention satisfies these needs as well as others.

SUMMARY OF THE INVENTION

In some embodiments, the present invention provides a particle comprising an ion channel polypeptide and a membrane potential-sensitive dye.

In some embodiments, the present invention provides a particle, wherein the particle comprises an enveloped virus.

In some preferred embodiments, the virus comprises an ion-channel polypeptide that is endogenous to the virus or cell from which the particle is derived.

In some preferred embodiments the virus is selected from the group consisting of influenza A, influenza B, influenza C, HIV-1, HIV-2, SIV, MLV, EIAV, RSV, VSV, ALV, and baculovirus In some embodiments, the particle is a lipoparticle which encompasses enveloped and non-enveloped virus-like particles.

In some preferred embodiments, the lipoparticle is an enveloped virus-like particle comprising a viral core protein, an ion channel polypeptide, and a fluorescent dye.

In some preferred embodiments, the lipoparticle comprises an ion-channel polypeptide that is exogenous to the virus or cell from which the particle is derived.

In some further preferred embodiments, the lipoparticle comprises MLV core protein.

In some preferred embodiments, the lipoparticle comprises an ion channel polypeptide that is selected from the group consisting of hERG, SCN5a, KCNQ1+minK, hERG+MiRP1, M2, 5HT3a, Shaker, KCNQ2+KCNQ3 and KCNQ1, and combinations thereof.

In some embodiments, the membrane potential-sensitive dye is selected from the group consisting of di-4-ANEPPS, di-8-ANEPPS, rhodamine 421, oxonol VI, JC-1, DiSC3(5), CC2-DMPE, DiSBAC2(3), and DiSBAC4(3), DiSBAC(1)$_3$, FMP-Blue, FMP-Red, VABSC-1, HLB 021-152, HLB 021-155, HLB 007-054, HLB 021-149, HLB 004-111, HLB 007-052, HLB 028-008, HLB 004-078, HLB 004-183, and combinations thereof.

In some embodiments, the particle comprises an ion channel polypeptide and an ion-sensitive dye.

In some embodiments, the particle comprises an ion channel polypeptide which further comprises a modification of a polypeptide.

In some embodiments, the present invention provides a method of detecting a change in membrane potential upon addition of a test compound comprising a) incubating a particle comprising an ion channel polypeptide with a test compound; and b) measuring a change in membrane potential.

In some embodiments, the present invention provides a method of detecting a change in membrane potential upon addition of a test compound comprising a) incubating a particle comprising an ion channel polypeptide and a fluorescent protein or dye with a test compound; and b) measuring a change in membrane potential.

In some embodiments, the present invention provides a method for testing modulators of ion channel activity comprising a) incubating a particle comprising an ion channel polypeptide with a test compound; and b) measuring change in fluorescence upon the addition of the ion channel's respective ion or ligand.

In some embodiments, the present invention provides a method for identifying novel viral ion channel polypeptides comprising a) incubating a particle comprising an ion channel polypeptide with one or more test ions; and b) measuring the change in fluorescence upon the addition of one or more test ions.

In some embodiments, the present invention provides a method of identifying a stimulator of an ion channel polypeptide comprising: a) contacting a particle comprising an ion channel polypeptide with one or more test compounds; and b) measuring change in fluorescence upon the addition of the ion channel's respective ion or ligand.

In some embodiments, the present invention provides a method of identifying an inhibitor of a known stimulator of an ion channel comprising the steps of: a) contacting a particle comprising an ion channel polypeptide with one or more test compounds; b) contacting said particle with a stimulator compound; c) measuring the change in fluorescence upon the addition of the stimulator.

In some embodiments, the present invention provides a method of detecting changes in ion concentration in a location comprising: a) microinjecting a particle comprising an ion channel polypeptide and a fluorescent protein or dye with a known interior ion concentration into said location; and b) detecting changes in ion concentration by measuring a change in fluorescence upon addition of stimulus.

In some embodiments, the present invention provides a method of altering the interior ion concentration of a particle comprising an ion channel polypeptide comprising: a) contacting said particle with a solution of known ion concentration; and b) electroporating the particle.

In some embodiments, the present invention provides a method for detecting the ability of a test compound to inhibit ion channel polypeptide activity comprising: a) contacting a particle comprising an ion channel polypeptide with a test compound; and b) detecting ion channel activity by inducing fluorescence due to a group of techniques consisting of ion transport, pH change, or combinations thereof; wherein a decrease in ion channel activity in the presence of said test compound indicates said test compound inhibits ion channel activity.

In some preferred embodiments, the present invention provides a method wherein the ion channel polypeptide is selected from the group consisting of hERG, SCN5a, KCNQ1+minK, hERG+MiRP1, M2, 5HT3a, Shaker, KCNQ2+KCNQ3 and KCNQ1, and combinations thereof.

In some embodiments, the present invention provides a particle comprising an ion channel polypeptide and a fluorescent protein, wherein said particle has been dried in the presence of sucrose.

In some embodiments, the present invention provides a method of detecting ion channel polypeptide activity comprising: a) stimulating a particle comprising an ion channel polypeptide with electricity from a computer controlled electrode array; and b) measuring the fluorescent wavelength of light emitted from said particle upon stimulation.

In some embodiments, the present invention provides a lipoparticle comprising an ion channel polypeptide and a fluorescent protein.

In some preferred embodiments, the present invention provides a lipoparticle wherein the ion channel polypeptide comprises a modification.

In some preferred embodiments, the present invention provides a lipoparticle wherein said fluorescent protein emits a fluorescent wavelength of light in response to the absence or presence of an ion.

In some preferred embodiments, the present invention provides a lipoparticle wherein said fluorescent protein emits a fluorescent wavelength of light in response to the absence or presence of a membrane potential.

In some preferred embodiments, the present invention provides a lipoparticle, wherein the fluorescent protein is GFP, pHFluorin, or a modification thereof.

In some embodiments, the present invention provides a particle comprising an ionophore.

In some embodiments, the present invention provides a microarray comprising particles which further comprise an ion channel polypeptide, fluorescent protein or dye, and combinations thereof.

In some embodiments, the present invention provides a microwell plate comprising the particles which further comprise an ion channel polypeptide, fluorescent protein or dye, and combinations thereof.

In some further embodiments, the present invention provides a kit comprising the microwell plate comprising the particles which further comprise an ion channel polypeptide, fluorescent protein or dye, and combinations thereof.

In some embodiments, the present invention provides a method of detecting ion channel polypeptide activity comprising: a) exposing a particle comprising an ion channel polypeptide to a radioactive element; and d) measuring radioactive ion efflux upon addition of a stimulator of said ion channel polypeptide.

In some embodiments, the present invention provides a microarray comprising particles further comprising an ion channel polypeptide and a fluorescent protein. In some embodiments, the present invention provides methods for detecting the ability of a test compound to inhibit hERG ion channel activity comprising contacting a particle with a test compound, and detecting hERG activity, wherein a decrease in hERG activity in the presence of the test compound indicates the test compound inhibits hERG activity.

In some embodiments, the present invention provides methods for detecting the ability of a test compound to inhibit M2 ion channel activity comprising contacting a particle with a test compound, and detecting M2 activity, wherein a decrease in M2 activity in the presence of the test compound indicates the test compound inhibits M2 activity.

BRIEF DESCRIPTION OF THE DRAWINGS

FIG. 1. A. Translocation of ions across viral membranes can be detected. Lipoparticles (1-5 ul) were incubated for 5 minutes with 1 uM valinomycin prior to addition to 45 ul of 10 mM Hepes containing 0.2 ul FMP dye in a total volume of 50 ul. Solutions were excited at 530 nm, during which 30 mM $K_2SO_4$ (final concentration) was added to each (arrow). Fluorescent emission, measured at 565 nm every 5 seconds, was proportional to the number of lipoparticles used, and was normalized to a baseline unit-less value of 1.0 for ease of comparison. A small decrease in signal of approximately 10% was observed in most negative control samples, proportional to the 10% dilution of dye upon injection of $K_2SO_4$. B. Valinomycin is needed to mediate translocation of $K^+$ across lipoparticle membranes. Lipoparticles (5 ul, or 20E6 DLS (Dynamic Light Scattering) units) were either treated with 1 uM valinomycin (treated) or buffer alone (control), and FMP dye in buffer added as described above. Upon addition of $K_2SO_4$ to a final concentration of 30 mM (first arrow at t=100 sec), a fluorescent signal was recorded only in lipoparticles pre-treated with valinomycin. The lipoparticles that were not treated exhibited no response. Upon addition of 1 uM valinomycin (second arrow at t=240 sec) to control lipoparticles, however, a fluorescent signal was recorded, indicating that valinomycin, which may be added prior to, or subsequent to, $K^+$, is required for ion transport across particle membranes. Buffer containing dye and $K_2SO_4$ (but no lipoparticles) did not respond to valinomycin (not shown) C. Translocation of ions is dependent on $K^+$ concentration. Lipoparticles treated with valinomycin and FMP dye, as described herein, were brought to final concentrations of $K_2SO_4$ as indicated, and fluorescence measured as described. Injection and final volumes were kept constant. Fluorescent signal was found to be positively correlated to the concentration of $K^+$ added. D. Translocation of ions is $K^+$-specific, and requires an intact membrane. Valinomycin- and FMP-treated lipoparticles generated a fluorescent signal upon addition of 30 mM $K_2SO_4$ (final concentration), or 60 mM KCl, but not with 60 mM NaCl. Prior disruption of lipoparticle structure using 0.05% deoxycholate detergent (DOC) eliminated the response to 30 mM $K_2SO_4$.

Figure 2:
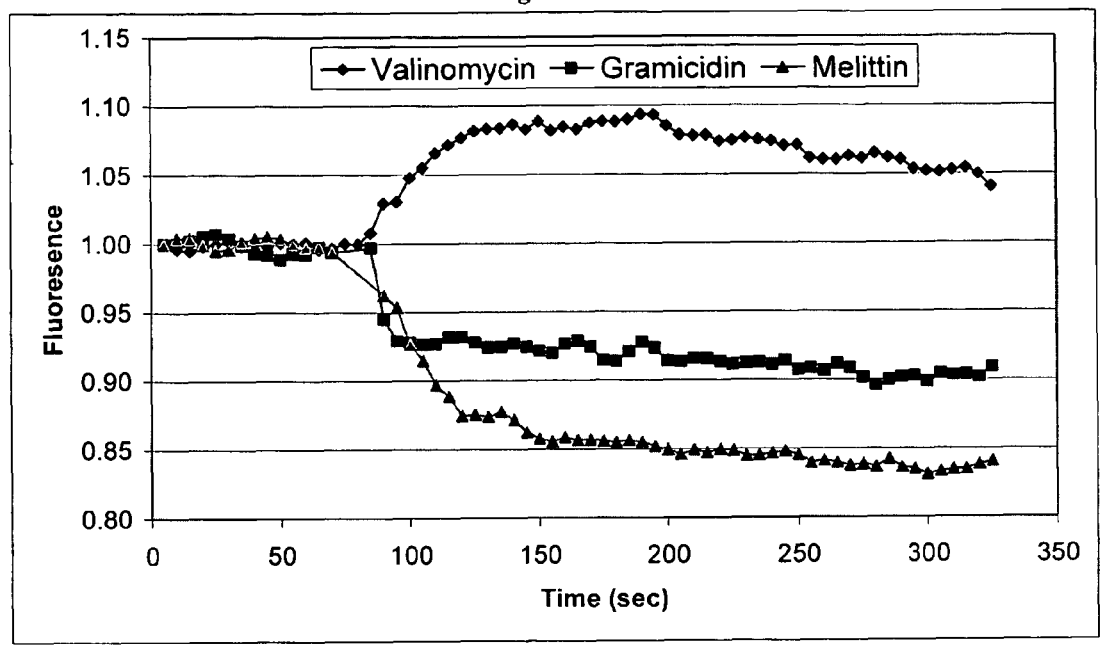

FIG. 2. Prior disruption of the lipoparticle structure using the non-specific pore-forming peptides gramicidin (1 uM), or melittin (5 uM), eliminated the response to 30 mM $K_2SO_4$.

FIG. 3. Detection of ion movement across the membranes of intact native influenza virions. A. Live influenza A virus were purified twice through 20% sucrose cushions and visualized by dynamic light scattering and fluorescent microscopy (inset, stained with Nile Red). B. Purified Influenza A virions treated with valinomycin and loaded with FMP dye demonstrated an increase in fluorescence upon challenge with K+ solution, suggesting $K^+$ movement to the virus interiors.

Figure 4:
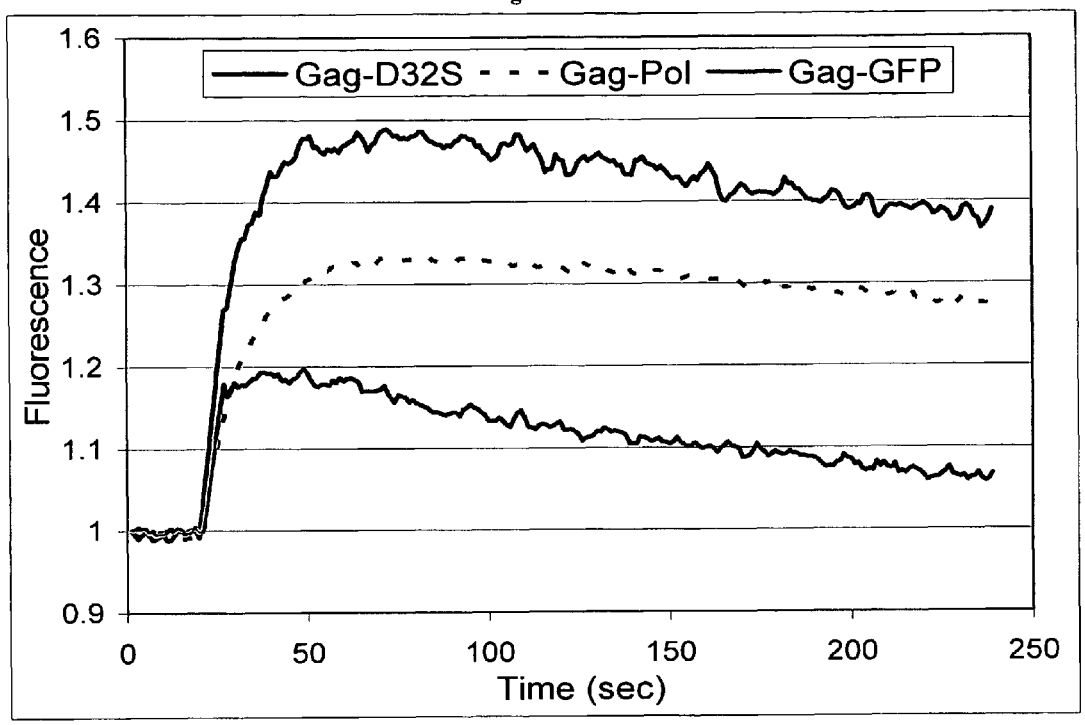

FIG. 4. Lipoparticles were produced using uncleaved wild-type MLV (murine leukemia virus) Gag-Pol, Gag-Pol with a D32S mutation in pol (which inactivates protease function), or a Gag-GFP fusion protein (no pol). Following treatment for 5 minutes with 1 uM valinomycin, lipoparticles were added to buffer containing FMP dye, as described herein. Upon addition of K2SO4 to a final concentration of 60 mM, an increase in fluorescent signal was recorded, indicating that lipoparticles produced using diverse core protein structures are capable of supporting a membrane potential. Gag-D32S Lipoparticles exhibited a slightly increased response.

Figure 5:
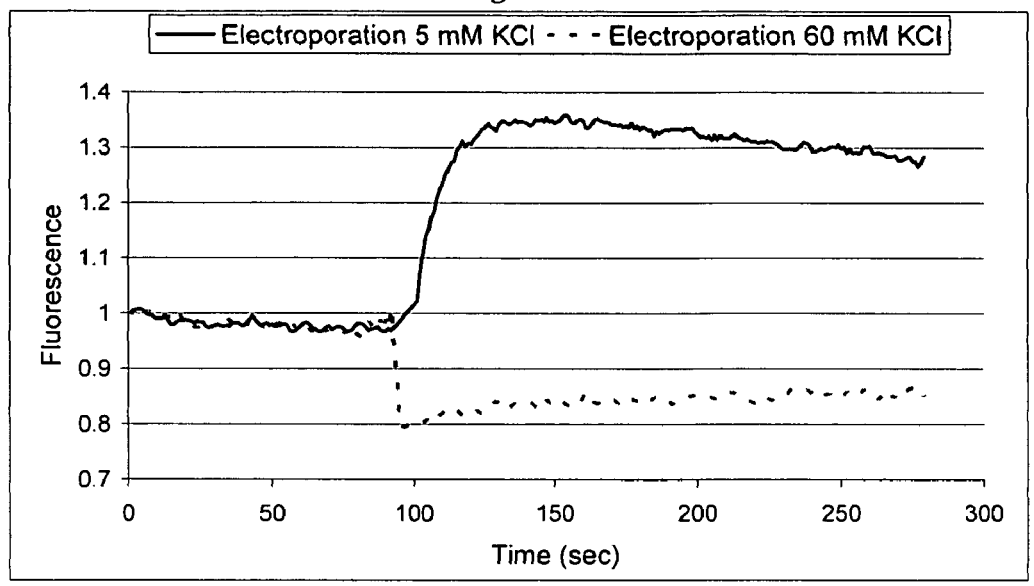

FIG. 5. MLV Lipoparticles were electroporated in the presence of 60 mM K+ (high-K), or 5 mM K+ (low-K). After electroporation, the K+ concentration of all buffers was adjusted to 60 mM and FMP dye was added. Addition of Valinomycin at t=100 to a final concentration of 1 uM caused a fluorescent signal in the low-K lipoparticles, but not in the high-K lipoparticles. This demonstrates that using electroporation, the internal ion concentrations of lipoparticles can be made to match those of the electroporation buffer.

Figure 6:
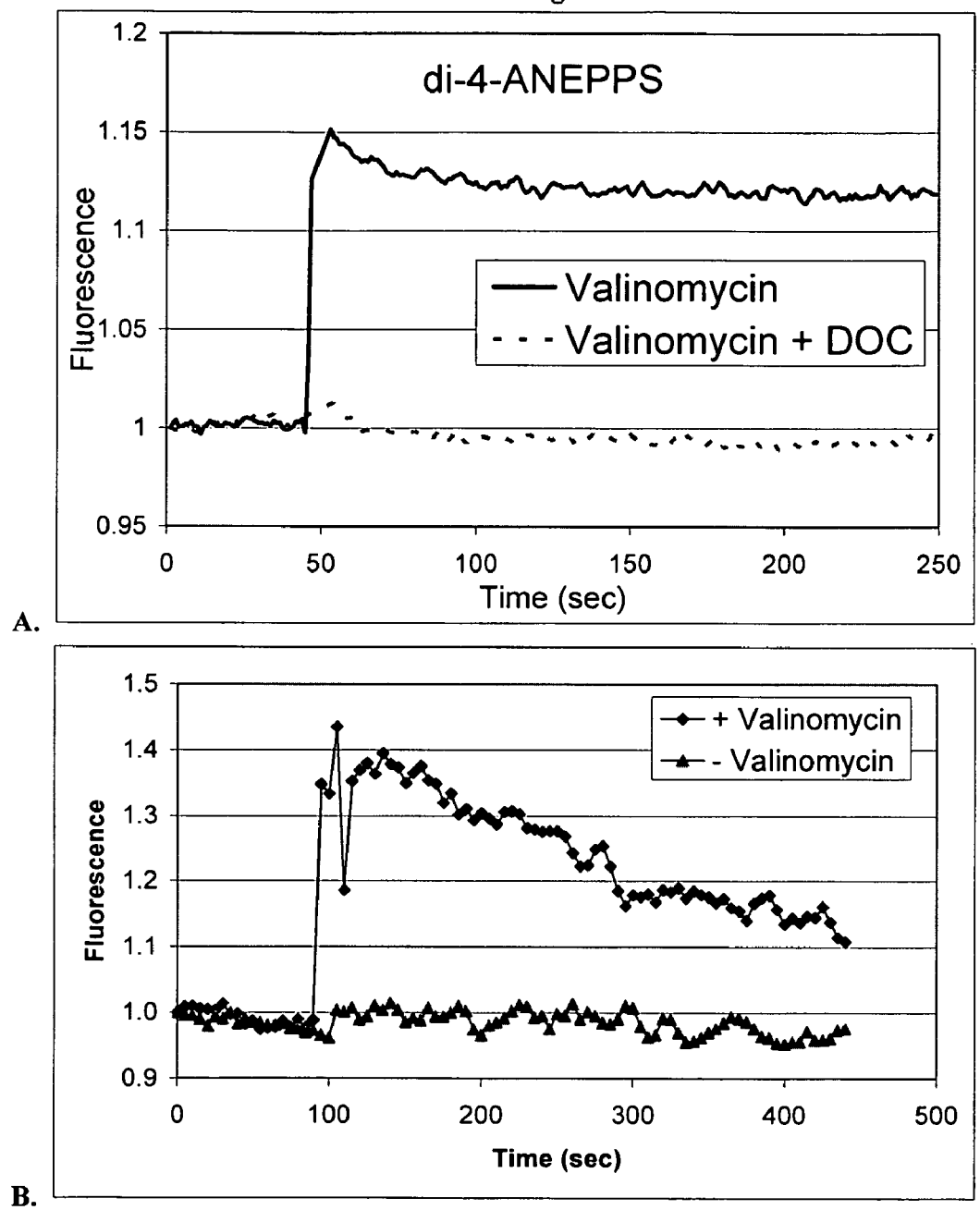

FIG. 6. Ion movement across intact viral membranes can be monitored using diverse membrane potential-sensitive lipophilic dyes. Lipoparticles were treated with valinomycin, and then loaded with either di-4-ANEPPS (A), or DiBAC4(3)(B). Both dyes were capable of reporting, by increased fluorescence, the movement of K+ across viral membranes. No fluorescent signal was recorded when viral structures were disrupted using DOC (A), or when valinomycin treatment was omitted (B). These data indicate that ion movement across intact viral membranes may be monitored using diverse membrane potential-sensitive dyes.

FIG. 7. A. Monitoring FCCP-mediated H+ movement across lipoparticle membranes. Lipoparticles pre-treated with the ionophore FCCP were added to a buffer containing the membrane potential-sensitive dye FMP. Following the addition of HCl to a final pH of approximately 6.0, an increase in fluorescence was observed, indicative of the movement of H+ across lipoparticle membranes. Addition of a pore-forming peptide (mellitin) 300 sec later attenuated the fluorescent signal to baseline, again confirming the ability to detect a H+-driven membrane potential in virus particles. Inhibitors of influenza A M2-mediated H+ transport were unable to abrogate the fluorescent signal, which was substantially attenuated in lipoparticles not pre-treated with FCCP. B. Purified influenza virions treated with the protonophore FCCP (20 uM) could support a $H^+$-driven membrane potential upon the addition of a low-pH solution. Membrane potential was destroyed by addition of the pore-forming peptide mellitin (arrow at t=200).

FIG. 8. Detection of pH changes within viral particles. A. Retroviral lipoparticles produced with a Gag-GFP fusion protein were purified and fluorescence measured after equilibrating with buffers of different pH, indicating that interior pH can be monitored. B and C. Purified Gag-GFP lipoparticle suspensions exhibited appropriate changes in fluorescence when solvent pH was adjusted, indicating that movement of H+ across viral membranes, and changes in the interior pH can be monitored in real time. The sequence of buffers used to change pH during the experiment were 2 mM MOPS pH 6.5+1 uL 100 mM MOPS pH 7.5+1 uL 1M Tris pH 6, and 2 mM MOPS pH 7.5+1 uL 100 mM MOPS pH 7+1 uL 1M Tris pH 8.

Figure 9:
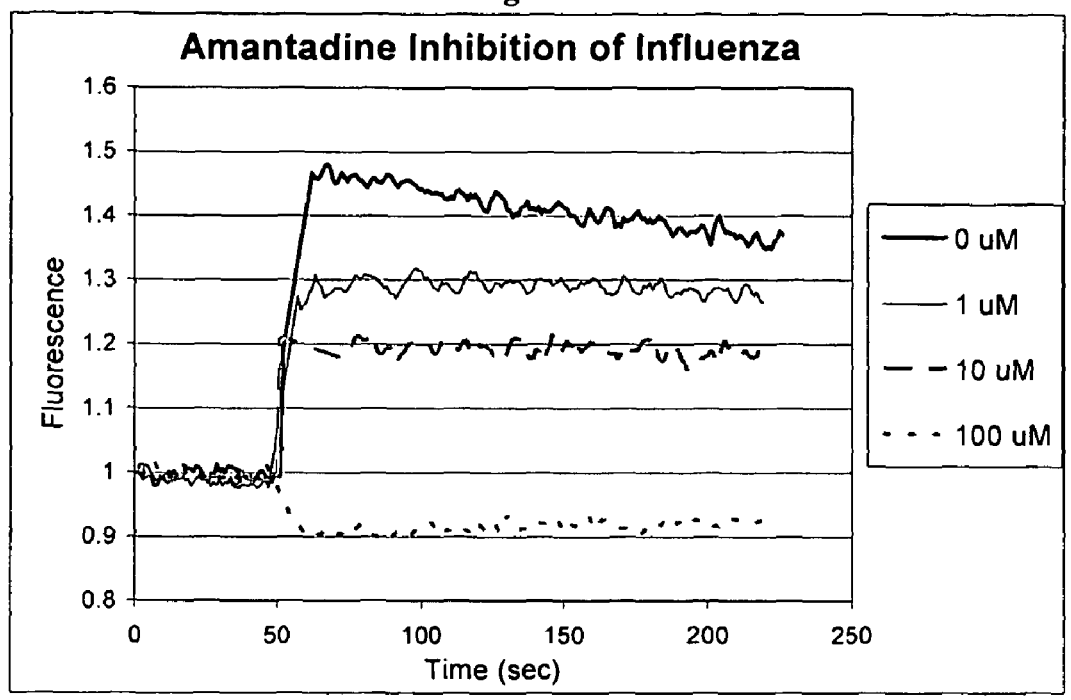

FIG. 9. Detection of M2 activity in intact native influenza virions. Purified influenza A virions challenged with low pH demonstrated an amantadine-inhibited membrane potential response when challenged with 1-100 uM amantadine.

Figure 10:
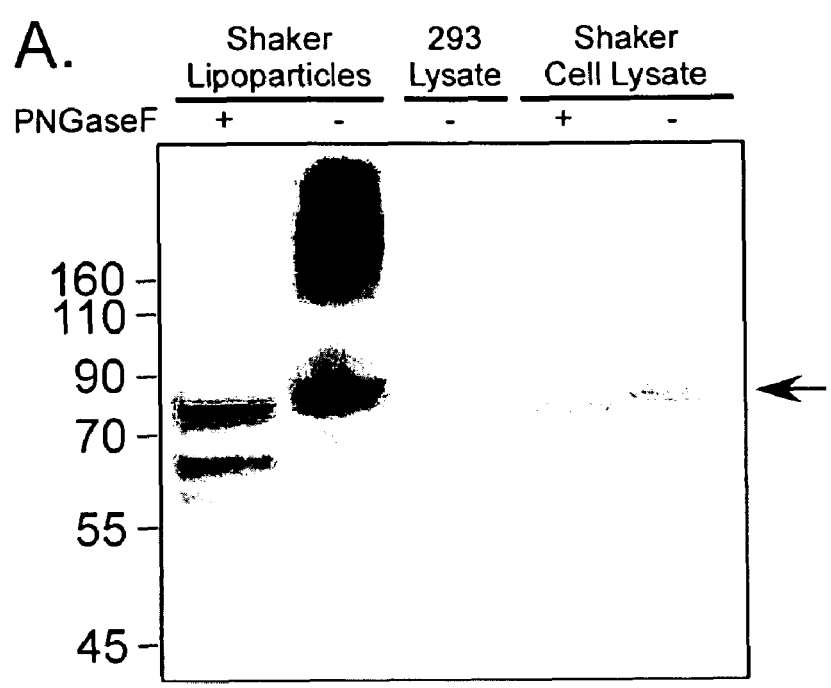

FIG. 10. Incorporation of Shaker into Lipoparticles. Lipoparticles containing the Shaker ion channel (Shaker(Δ6-46) T449V containing a FLAG epitope near its N-terminus) were produced, purified, and 4 ug of lipoparticles analyzed by western blot using an anti-FLAG antibody. Lysates from HEK-293 cells expressing Shaker were similarly analyzed by Western blot (50,000 cells per lane). Lipoparticle and cell lysate Shaker both migrated at the appropriate molecular weight (arrow). Analyses were conducted with or without deglycosylation using PNGase F (New England Biolabs). Shaker contains two N-linked carbohydrates (N259 and N263) in its first extracellular loop, and exhibited an appropriate reduction in molecular weight upon their removal. The recommended treatment procedure for PNGaseF digestion (extensive boiling and SDS treatment prior to digestion) also resulted in reduction of the artifactual high molecular weight aggregates seen in both lipoparticle and cell lysate lanes.

Figure 11:
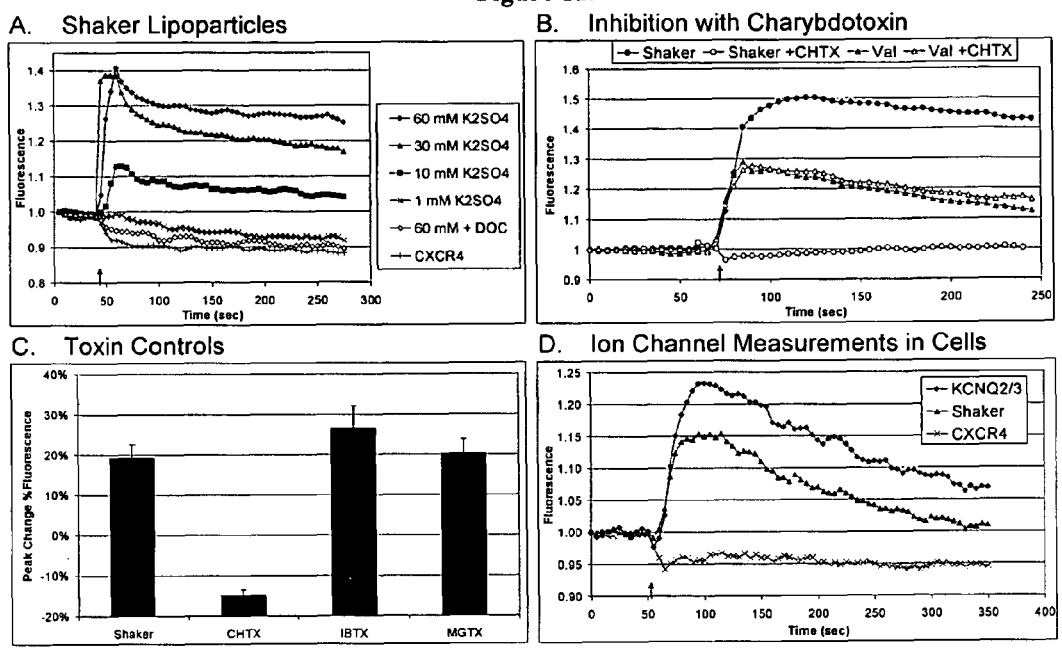

FIG. 11. A. Shaker mediates the translocation of $K^+$ across intact lipoparticle membranes. 5 ul of Shaker lipoparticles were added to 45 ul of 10 mM Hepes containing 0.2 ul FMP dye. Once baseline was established, 1-60 mM $K_2SO_4$ was injected (arrow), maintaining a constant final volume. Shaker lipoparticles pre-treated with 0.05% deoxycholate (DOC) and control CXCR4 lipoparticles showed no response to 60 mM $K_2SO_4$. Results for all curves are normalized to a baseline relative fluorescence value of 1.0 for ease of comparison. B. Lipoparticle Shaker activity is inhibited by CHTX. A membrane potential was established in Shaker lipoparticles by adding 30 mM $K_2SO_4$ after pre-incubation with 10 nM charybdotoxin (CHTX) or buffer control. Lipoparticles pre-treated with 1 uM valinomycin (Val) and 10 nM CHTX were also tested as a control. C. Non-specific toxins do not influence lipoparticle Shaker activity. Shaker lipoparticles were pre-treated with 10 nM CHTX, iberiotoxin (IBTX), margatoxin (MGTX), or buffer alone (Shaker), loaded with FMP, and 30 mM $K_2SO_4$ added. The average and range of duplicate experiments is shown. D. Lipoparticle ion channel activity is similar to that in cells. HEK-293 cells were transfected with the indicated ion channels (Shaker, KCNQ2/3) or a negative control protein (the G protein-coupled receptor CXCR4). $5 \times 10^5$ cells were mixed with 5 ul FMP dye and then stimulated with 30 mM $K_2SO_4$ (t=50 sec).

Figure 12:
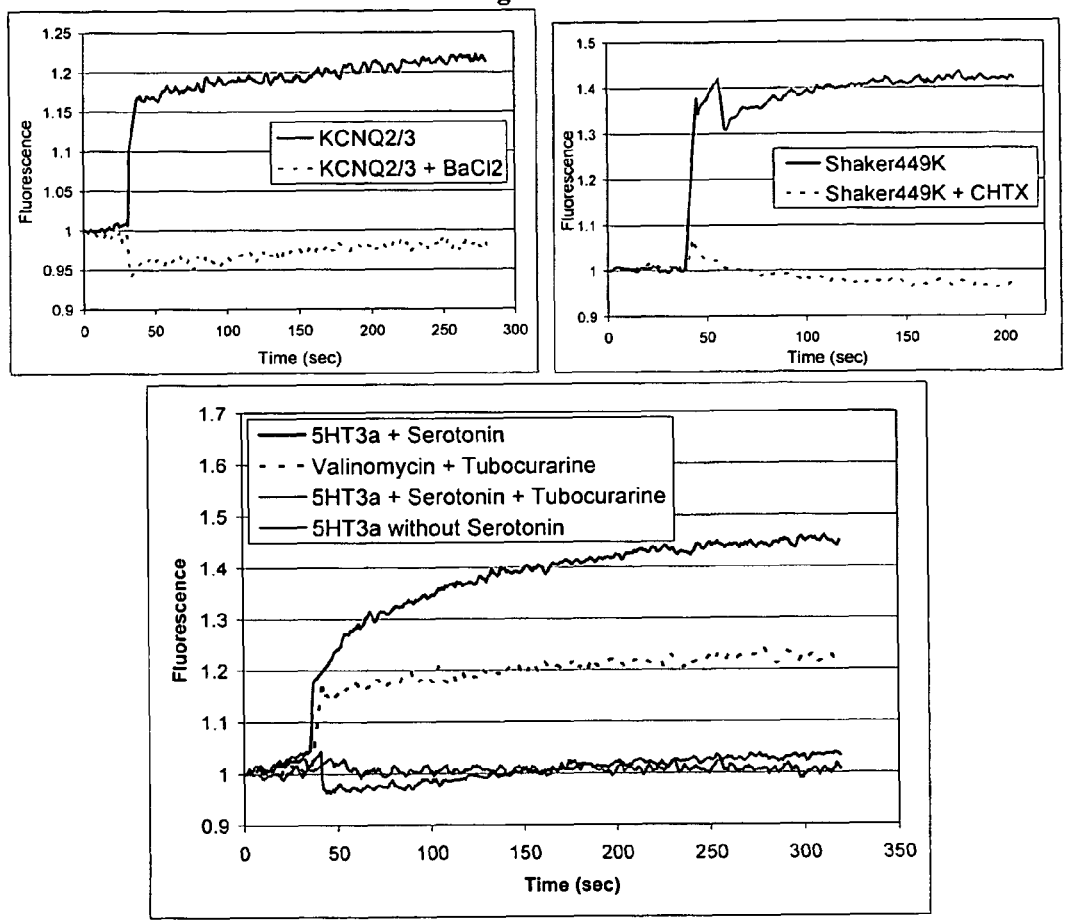

FIG. 12. The activity of structurally and functionally diverse ion channels can be monitored within lipoparticles. The hetero-oligomeric human $K^+$ channels KCNQ2 and KCNQ3 (A), the fast-inactivating (26 msec time constant) Shaker T449K mutant (B), and the ligand-activated 5HT3a ion channel were incorporated separately into lipoparticles. Lipoparticles were loaded with the membrane potential-sensitive dye, FMP, and fluorescence monitored while 30 mM $K_2SO_4$ was added (or NaCl for 5HT3a). A fluorescent signal, indicating $K^+$ movement across the lipoparticle membrane was recorded from KCNQ2/3 and Shaker-449K lipoparticles, and from 5HT3a lipoparticles in the presence (but not absence) of serotonin. Controls included inhibition by 20 mM $BaCl_2$ for KCNQ2/3, by 10 nM charybdotoxin (CHTX) for Shaker 449K, and by tubocurarine for 5HT3a. Tubocurarine was not, however, able to inhibit K+ movement mediated by the ionophore valinomycin, demonstrating specificity.

Figure 13:
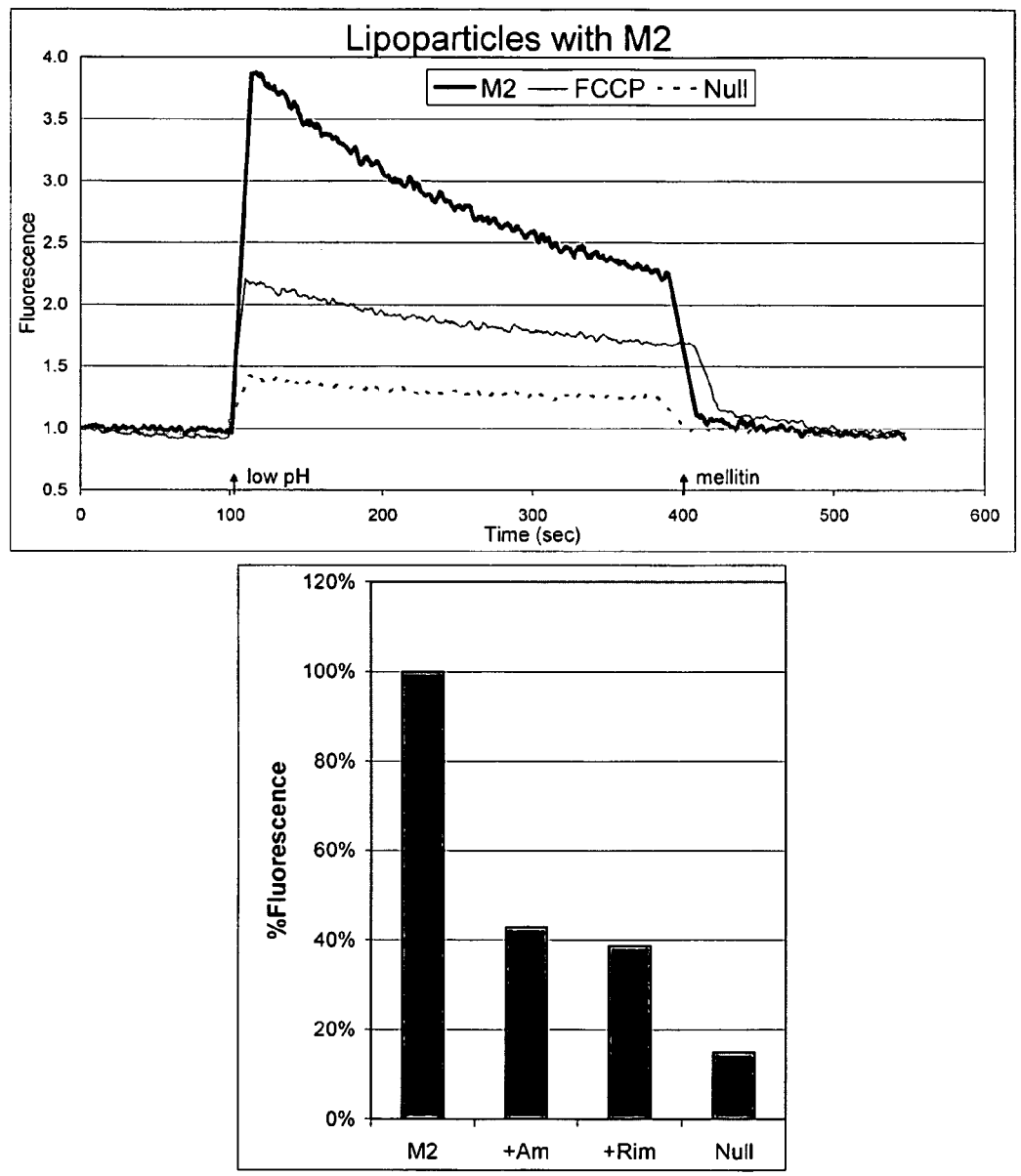

FIG. 13. Detection of M2 activity in lipoparticles. A. Lipoparticles prepared with the M2 ion channel ('M2'), a protonophore ('FCCP'), or no ion channel or ionophore ('Null') were tested for response to low pH. Addition of a pore-forming peptide (mellitin) 300 sec later attenuated the fluorescent signal to baseline, again confirming the ability to detect an M2-mediated membrane potential in virus particles. The same number of lipoparticles were used in each sample. B. Comparative fluorescent signal (% of maximum) from M2-lipoparticles, from M2-lipoparticles treated with amantadine (Am) and rimantadine (Rim), and from null-lipoparticles are shown.

Figure 14:
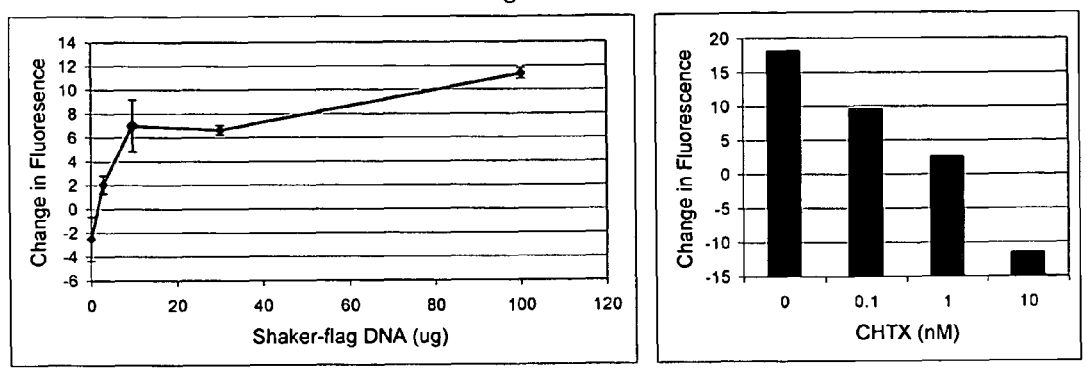

FIG. 14. A. Preparations of lipoparticles produced using different amounts of Shaker(Δ6-46)T449V plasmid (0, 3, 10, 30, or 105 ug), and loaded with FMP dye were tested, in triplicate, for their ability to conduct K+ across the lipoparticle membrane after the addition of 30 mM $K_2SO_4$. Lipoparticles produced from cells transfected with 10 ug or more of Shaker plasmid contained sufficient ion channels for nearly complete membrane depolarization. B. Lipoparticles produced using 10 ug Shaker plasmid were incubated with increasing amounts of Charybdotoxin (CHTX) prior to loading with FMP dye and addition of 30 mM $K_2SO_4$. The experiment was repeated three times with nearly identical results. Inhibition of membrane depolarization with even low concentrations (0.1 nM) of CHTX was evident, suggesting that both complete and intermediate inhibition of membrane depolarization can be detected. Concentrations of CHTX tested (up to 10 nM) had no effect on valinomycin-mediated $K^+$ flux (not shown). All data are indicated as the change in raw fluorescence units measured before and after $K^+$ challenge.

Figure 15:
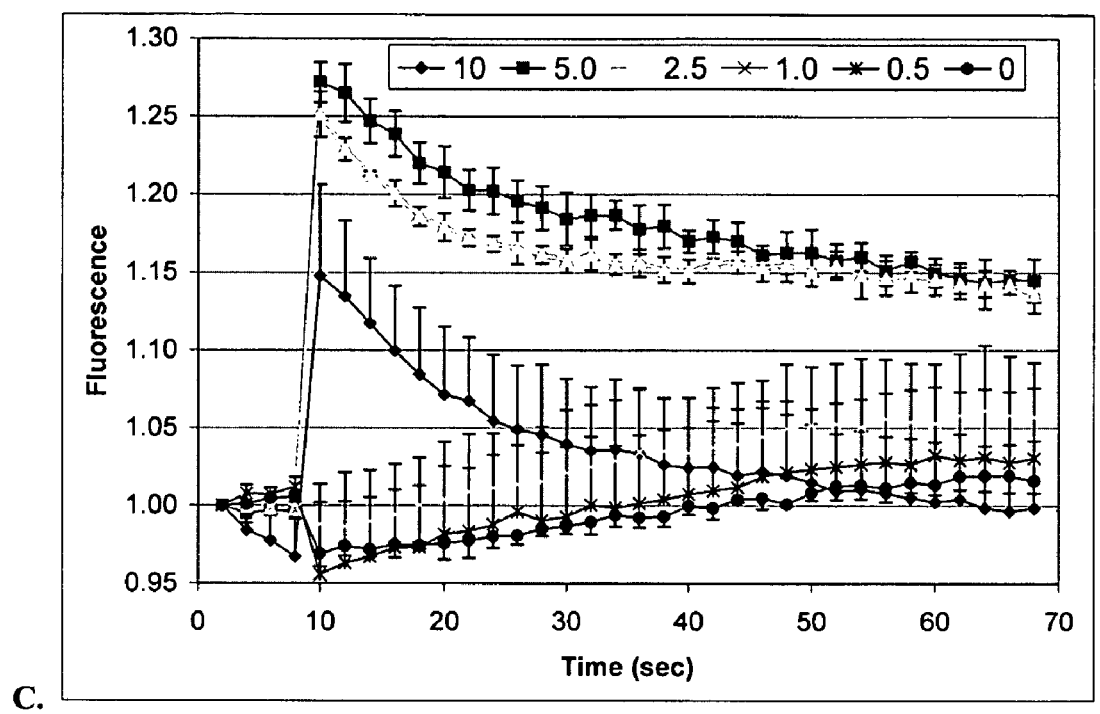

FIG. 15. A. Fluorescent signal can be optimized by titrating FMP dye quantity. The indicated amounts (ul) of FMP dye (Molecular Devices) were added to microplate wells containing 5 ul of valinomycin-treated lipoparticles in a total volume of 50 ul, and tested in duplicate for response to 50 mM $K_2SO_4$ using a Wallac Victor2V. B. Fluorescent signal can be optimized by titrating lipoparticle quantity. The indicated amounts (ul) of valinomycin-treated lipoparticles were mixed with 0.5 ul FMP dye in microplate wells in a constant volume of 50 ul, and tested in duplicate for response to 50 mM $K_2SO_4$. C. Optimization of Valinomycin. 5 ul of lipoparticles were mixed with the indicated final concentrations of valinomycin (uM) and 0.5 ul FMP dye before testing in duplicate for response on a Wallac Victor2V.

Figure 16:
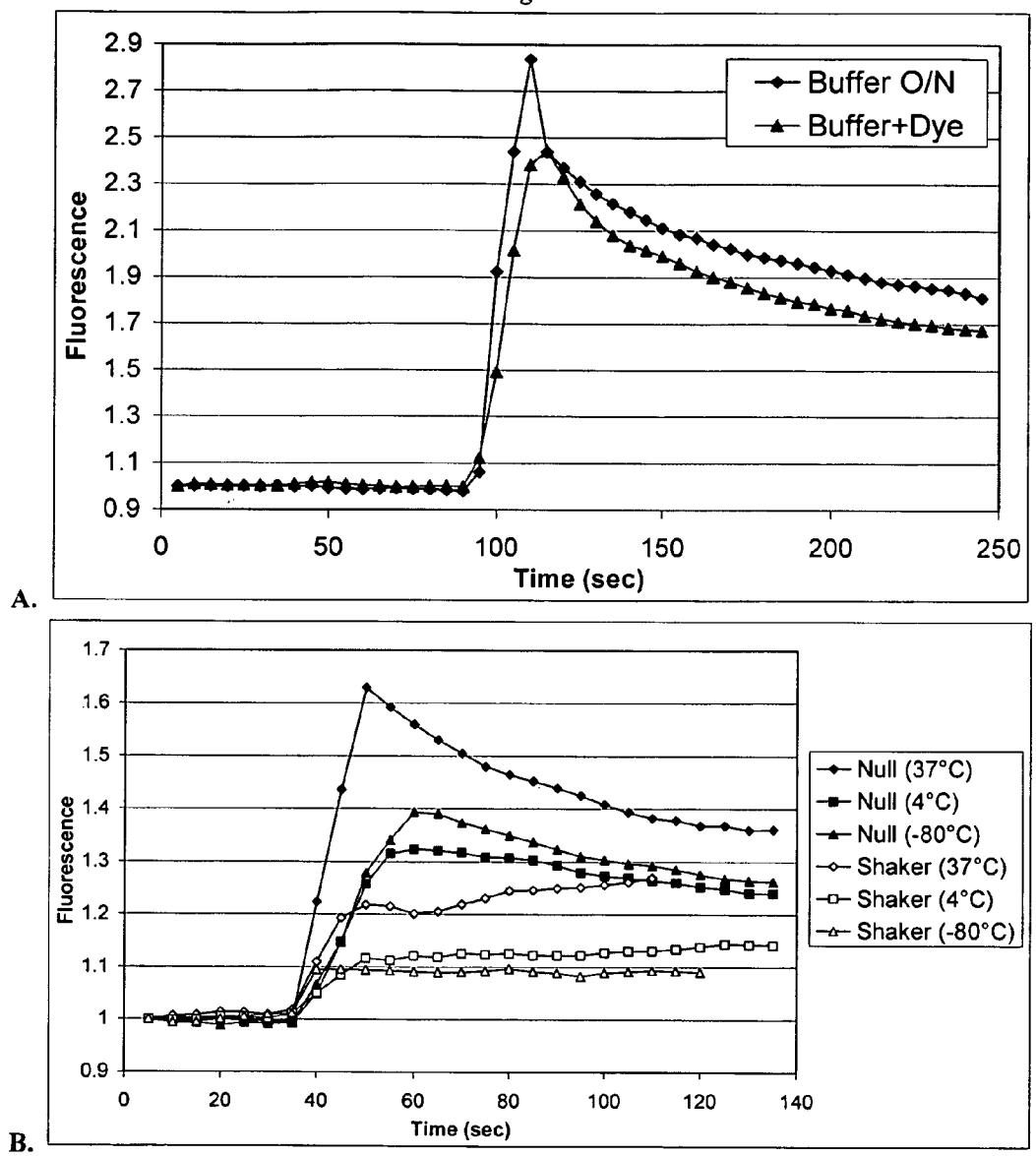

FIG. 16. A. Detection conditions are stable. Incubation of lipoparticles and valinomycin with FMP dye overnight or just prior to the addition of K+, resulted in a similar fluorescent signal upon challenge with K+. B. Storage of Null lipoparticles (treated with valinomycin just before assay) or Shaker lipoparticles at −80° C., 4° C., 37° C. for 1 hour had only minor effects on signal, demonstrating the stability of the lipoparticles for ion channel measurement at different temperatures. The experiments were conducted using a Perkin Elmer LS50B.

Figure 17:
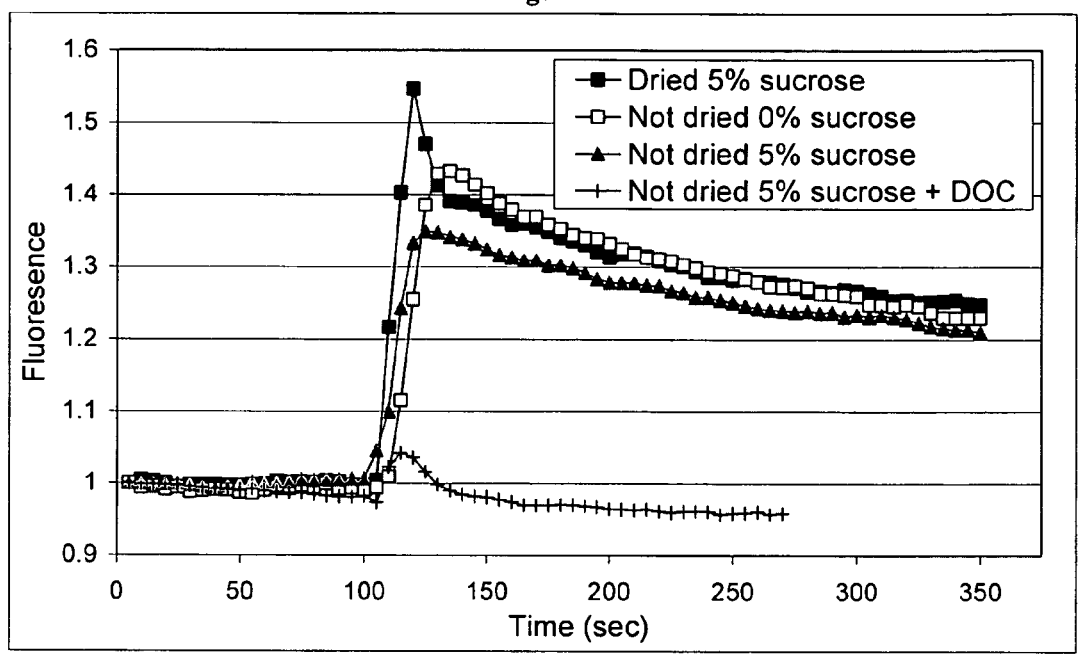

FIG. 17. Lipoparticles can be dried and reconstituted. Lipoparticles dried with 5% sucrose retained their ability to support a membrane potential once reconstituted.

FIG. 18. A and B. Detection of ion transport in lipoparticles is highly reproducible in high-throughput format. Twelve replicates of lipoparticles pre-treated with (C) and without (D) 2.5 uM valinomycin, and mixed with 0.5 ul FMP dye in a total volume of 50 ul, were tested for response to 50 mM $K_2SO_4$ injected into microplate wells.

FIG. 19. Detection of membrane potential in Lipoparticles using FLIPR and FlexStation. A. Lipoparticles prepared without a specific ion channel were prepared with or without 1 uM valinomycin, in triplicate. The Lipoparticles were mixed with FMP-Blue dye and aliquoted into wells of a clear-bottom 384-well microplate. The microplate was placed in a FlexStationII-384 (Molecular Devices). 30 mM K2SO4 was injected into each well at approximately 30 sec. Blank wells (with no particles or dye) were measured for comparison and used as plate blanks. B. Lipoparticles were prepared with varying amounts of the Shaker ion channel (26, 33, or 44 ug of plasmid during production) or with no ion channel (Null). The Lipoparticles were mixed with FMP-Blue dye and aliquoted into wells of a clear-bottom 384-well microplate. The microplate was placed in a FLIPR-Tetra (Molecular Devices). 30 mM K2SO4 was injected into each well at approximately 35 sec, and the response was measured.

Figure 20:
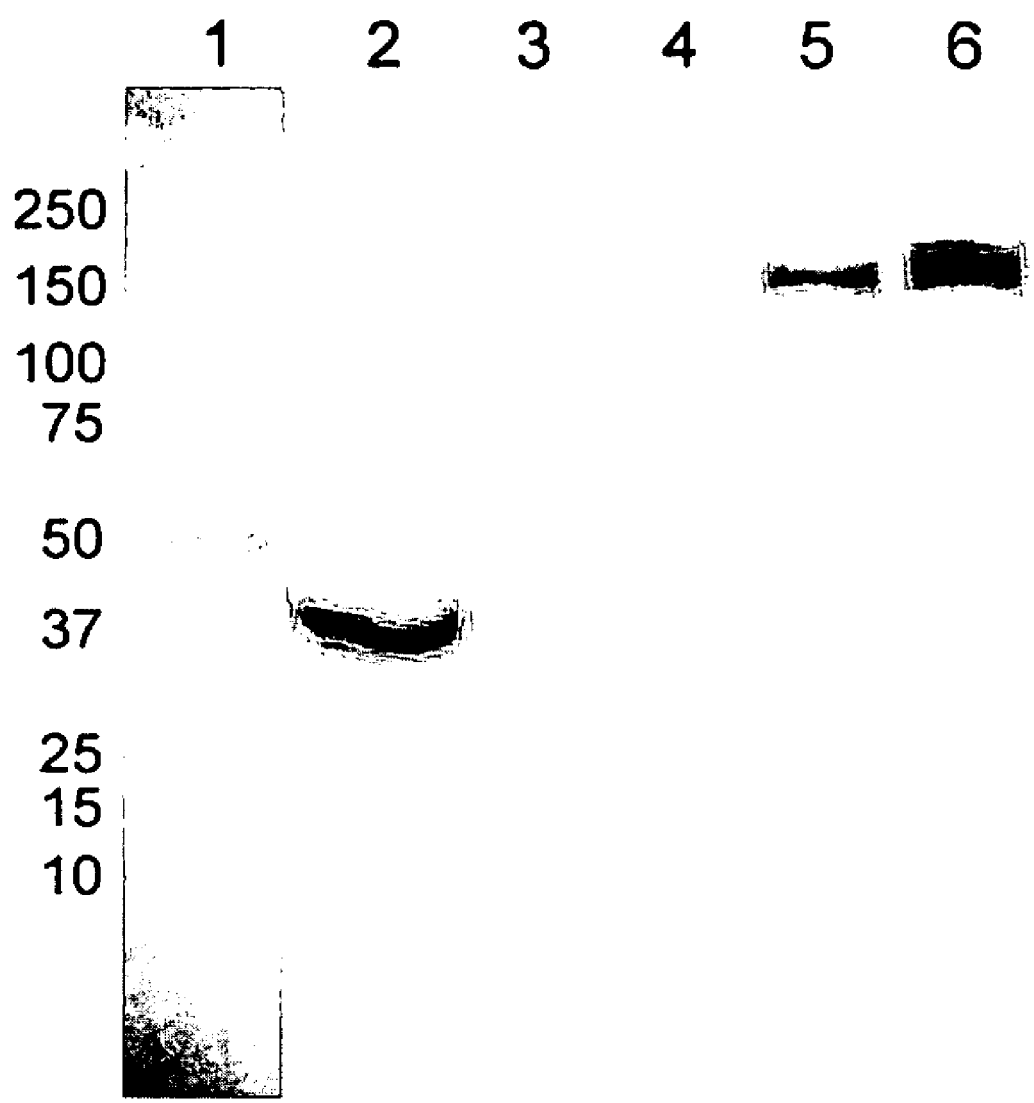

FIG. 20. Detection of the hERG ion channel in purified VLPs by Western Blot. The hERG K-channel was constructed with and without with an HA epitope tag near its N-terminus. Approximately $6 \times 10^6$ DLS counts/sec of VLPs, and approximately 10,000 293T cells were prepared and separated by SDS-PAGE, after which they were transferred to PVDF membranes and detected using a mouse anti-HA monoclonal antibody (HA.11, 1:2000, Covance) and an HRP-conjugated anti-mouse secondary monoclonal antibody (1:2000). Lanes: 1. molecular weight marker; 2. GFP-HA protein preparation (0.75 μg); 3. 293T cells expressing hERG; 4. VLPs incorporating hERG; 5. 293T cells expressing HA-hERG; 6. VLPs incorporating HA-hERG.

Figure 21:
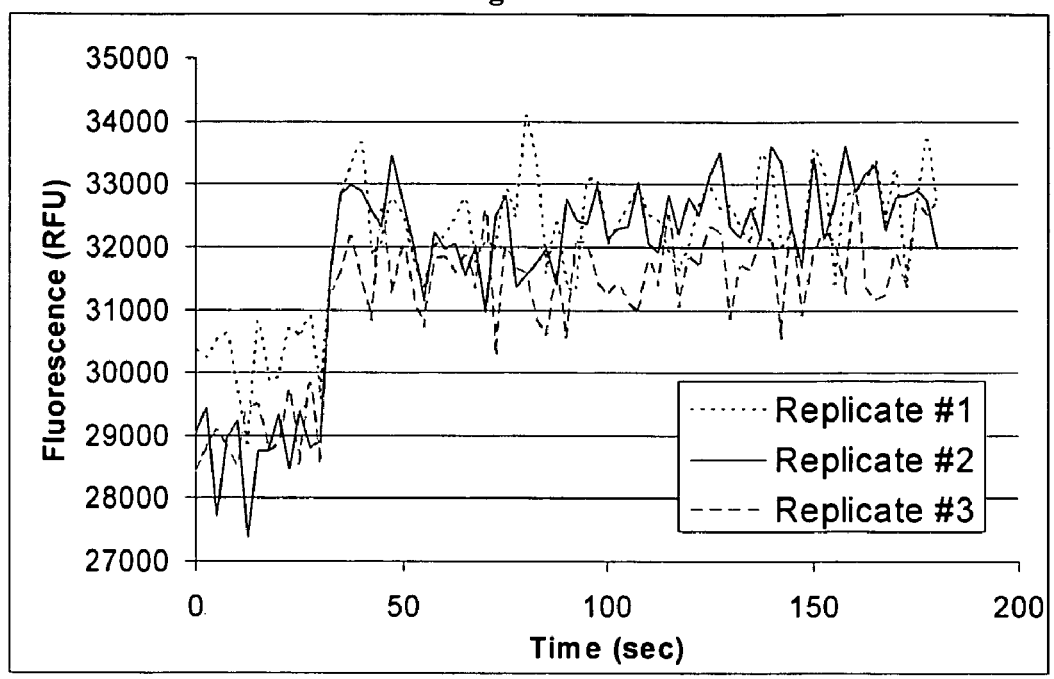

FIG. 21. Detection of ion channel function in hERG VLPs. VLPs containing hERG were suspended in a low-$K^+$ 10 mM Hepes buffer containing 1% FMP blue dye and aliquotted in a 384-well microplate ($5 \times 10^6$ DLS counts/sec of VLPs per well). $K_2SO_4$ was added to a final concentration of 30 mM in each well while monitoring fluorescence using a FlexStation II (Molecular Devices). An example of three replicates is shown. No significant response was observed when control VLPs containing a GPCR(CXCR4) were used (data not shown). Similar results were obtained using HA-hERG VLPS (data not shown).

Figure 22:
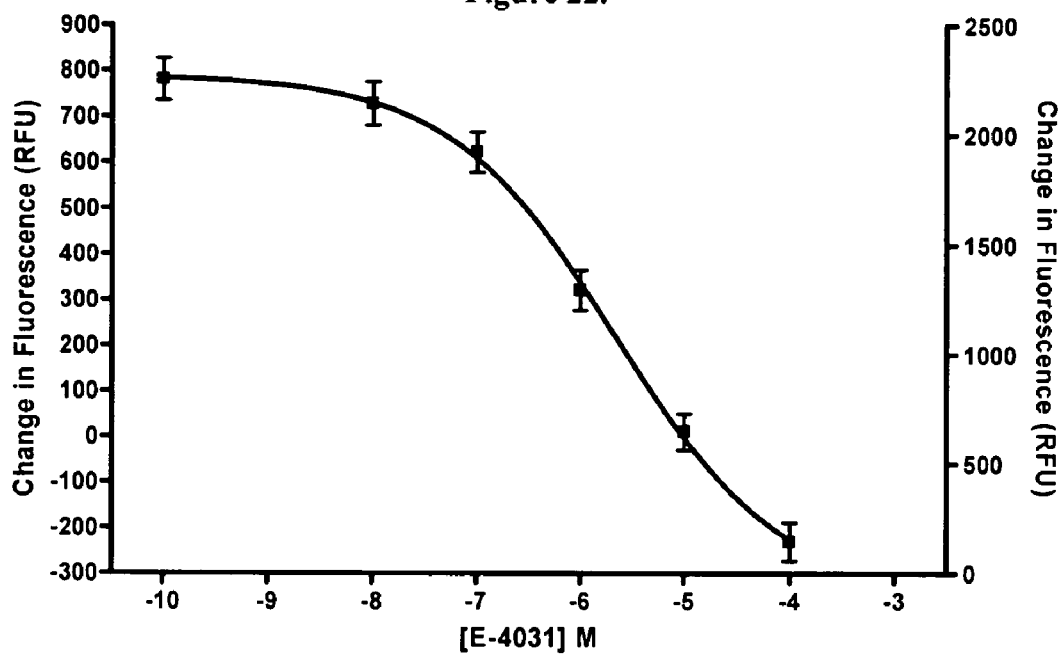

FIG. 22. Selective inhibition of hERG ion channel activity in intact VLPs. VLPs incorporating human hERG were suspended in 10 mM Hepes 7.0, 135 mM NaCl, 15 mM KCl, and containing 1% Molecular Devices' FMP dye. 0.001-100 μM of the selective hERG inhibitor E4031 was aliquotted into wells of a 384-well microplate. After 1 hour incubation at room temperature, fluorescence intensity was monitored during the addition of $K_2SO_4$ to a final concentration of 30 mM. After correction of fluorescence intensities for baseline values, an inhibition curve was constructed against the log of the mean E4031 concentration (Molar) in each well. E4031 was found to inhibit hERG $K^+$-transporting activity in VLPs with a potency (IC50) of 2.33 uM.

Figure 23:
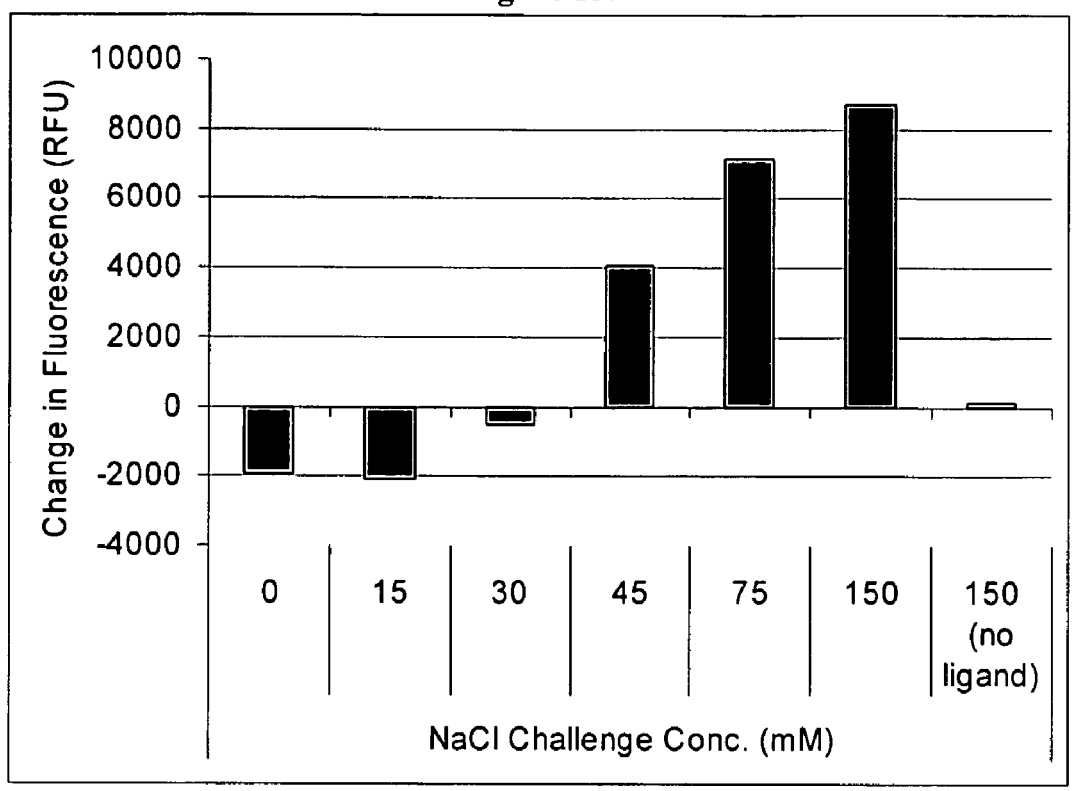

FIG. 23. Detection of 5HT3a ion channel activity in VLPs. VLPs incorporating the ligand-gated cation channel 5HT3a were prepared as described, suspended in 10 mM Hepes buffer containing 50 μM serotonin and 1% FMP dye, and aliquotted in triplicate in a 384-well microplate. Fluorescence was measured during addition of various concentrations of NaCl, and the change in fluorescence intensity, compared with baseline values, measured.

Figure 24:
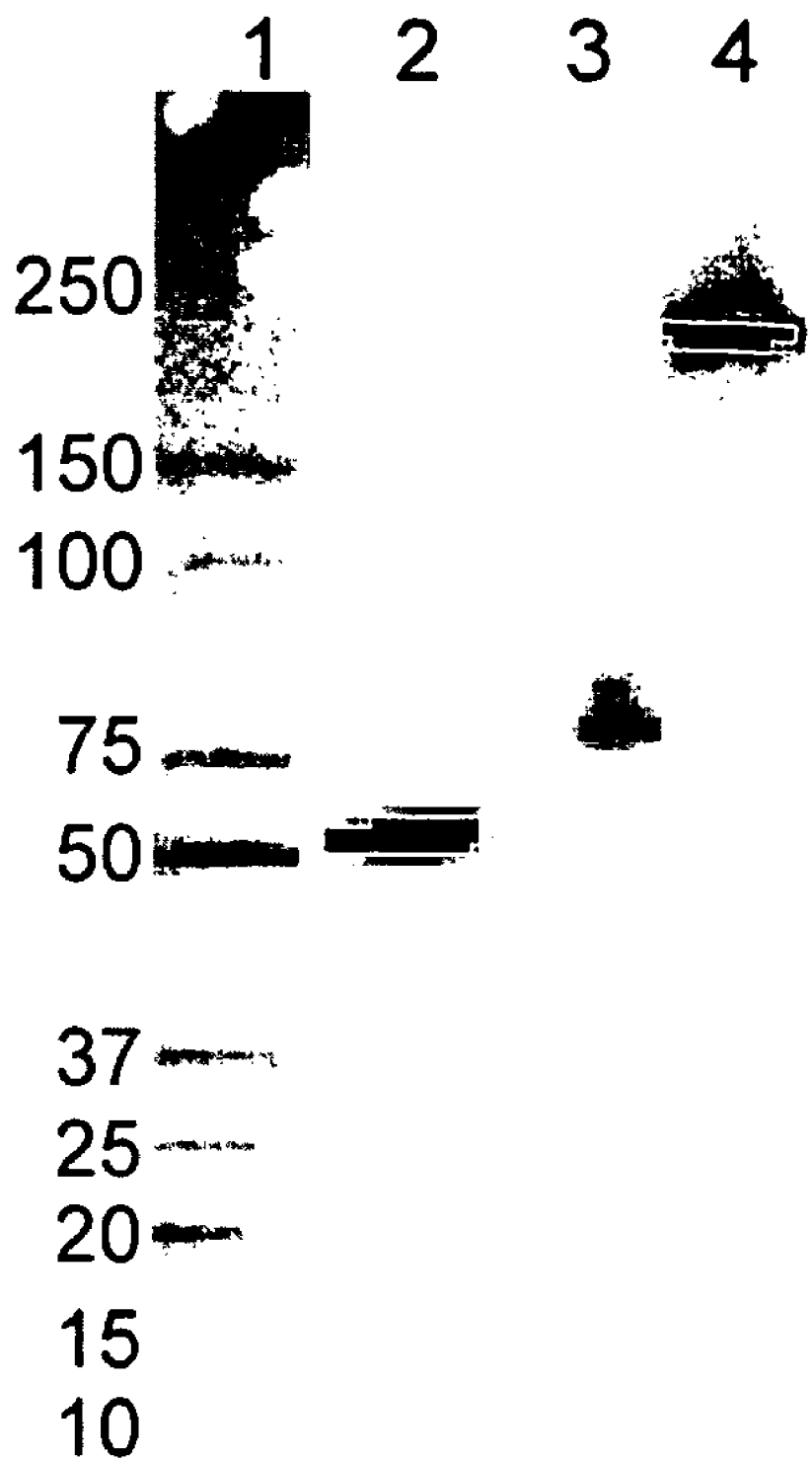

FIG. 24. Incorporation of the hERG ion channel into baculovirus particles. Baculovirus particles incorporating human hERG with a N-terminal HA tag, were produced and purified. Western blot analysis using a mouse anti-HA primary antibody (HA.11, 1:2000, Covance) and an HRP-conjugated anti-mouse secondary antibody (1:2000), confirmed incorporation of the HA-hERG construct in the baculovirus. Lanes: 1. molecular weight marker; 2. GFP-HA protein preparation (0.6 μg); 3. Baculovirus containing a chemokine receptor-V5 construct (negative control); 4. Baculovirus incorporating HA-hERG ($6 \times 10^6$ DLS counts/sec per lane).

Figure 25:
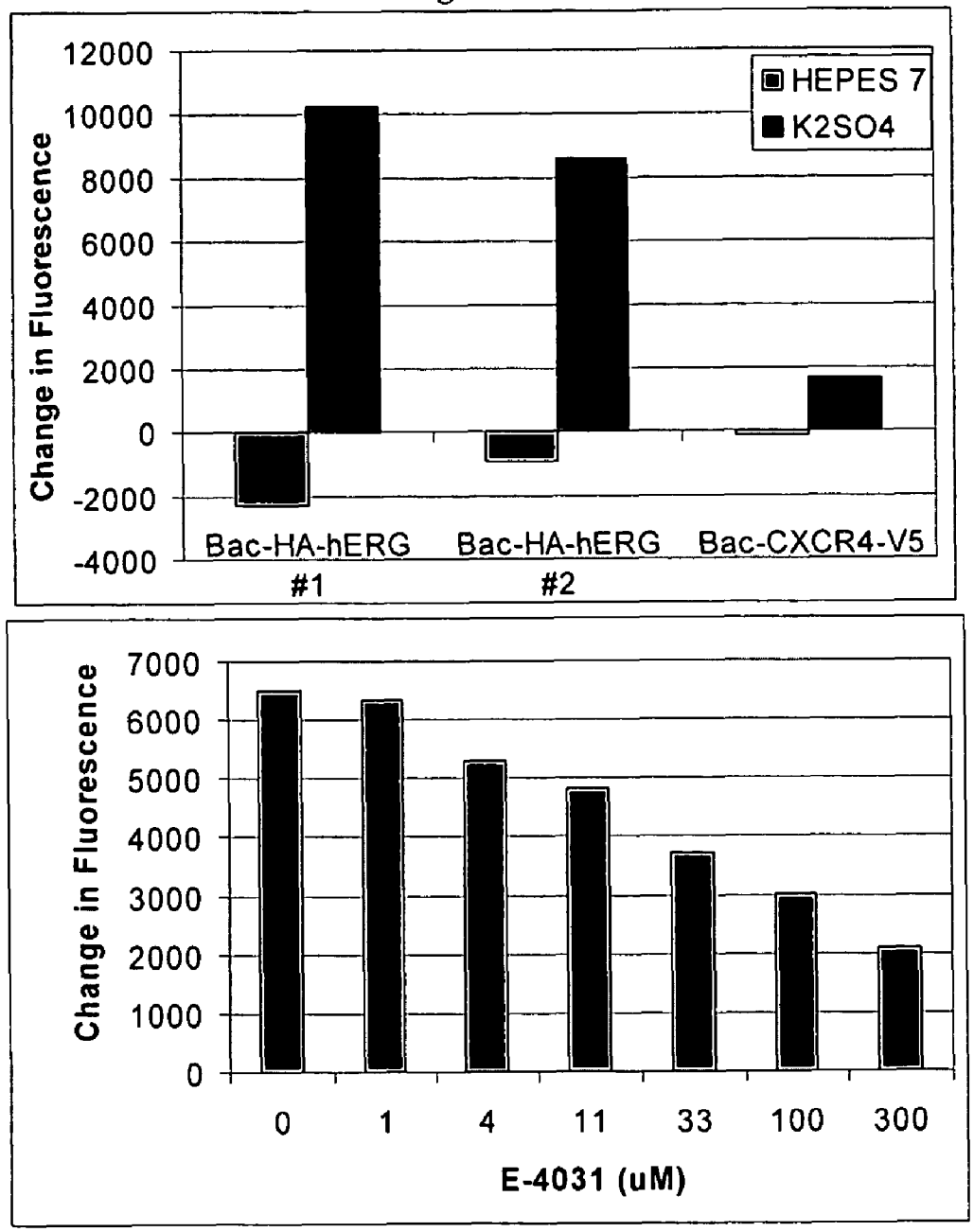

FIG. 25. A. Detection of ion channel function in intact baculovirus particles. Baculovirus incorporating human hERG $K^+$ ion channels were suspended in 10 mM Hepes pH 7.0, 135 mM NaCl, 15 mM KCl, and 1% FMP dye and aliquotted in 384-well microplates ($5 \times 10^6$ DLS counts/sec per well). Fluorescence was monitored using a FlexStationII microplate reader, and was corrected for baseline values. The addition of $K_2SO_4$ to a final concentration of 30 mM resulted in a substantial increase in fluorescence intensity, indicating translocation of $K^+$ across baculovirus membranes. $K^+$ was not substantially transported across the membranes of Baculoviral incorporating a non-ion channel protein (CXCR4), and the addition of Hepes buffer alone, instead of $K_2SO_4$, did not result in a significant change in fluorescence intensity in any wells. The results from two different clones of baculovirus HA-hERG are shown (#1 and #2). B. Inhibition of hERG ion channel activity in intact baculovirus particles. Pre-incubation of Baculoviral incorporating hERG with the selective hERG inhibitor E4031 for 1 hour at room temperature resulted in a concentration-dependent abrogation of $K^+$ translocation across baculovirus membranes by hERG.

Figure 26:
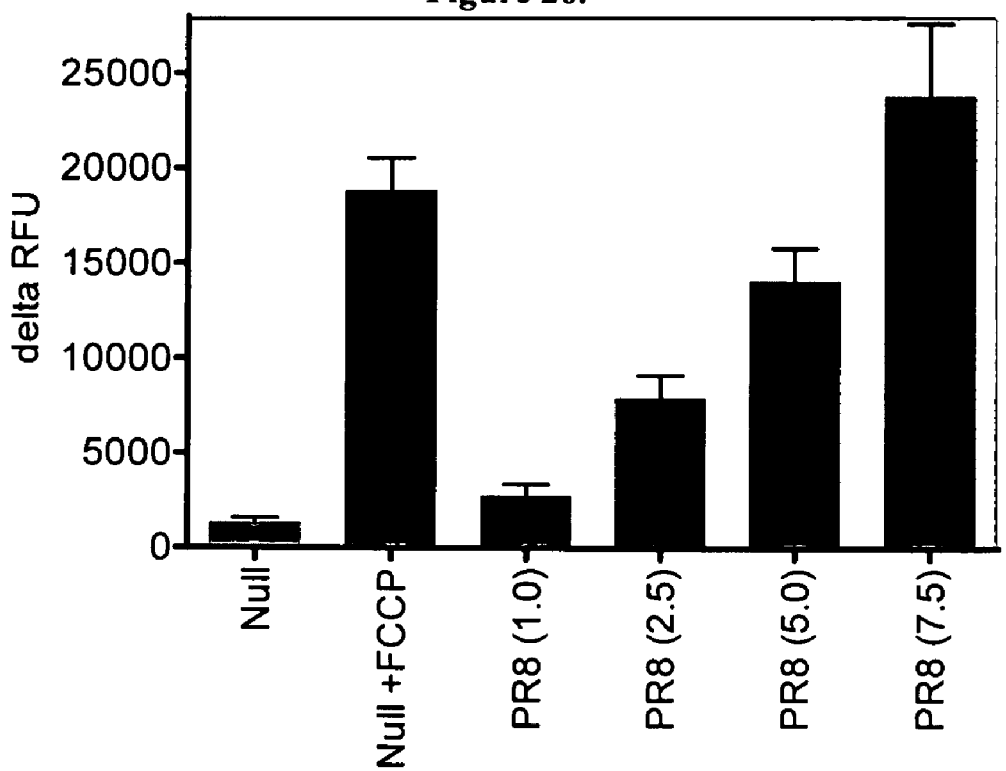

FIG. 26. Detection of M2 ion channel activity in intact influenza virions. PR8/34 influenza A virions grown in embryonated chicken eggs and purified, were suspended in HEPES buffer (pH 7.0) containing 0.4% FMP membrane potential dye. Fluorescence was monitored in a FlexStationII during the addition of MES buffer (pH 4.5). The increase in fluorescence intensity, after correction for baseline values, indicating transportation of $H^+$ across viral membranes, was found to be positively correlated to the number of particles in each well. The number of particles (in millions) is a relative value based on DLS counts/sec. MLV retroviral particles, which do not contain an $H^+$ ion channel, were used as a negative control (Null, $2.5 \times 10^6$ DLS counts), and MLV particles pre-treated with 5 uM of the protonophore FCCP were used as a positive control (Null+FCCP, $2.5 \times 10^6$ DLS counts).

Figure 27:
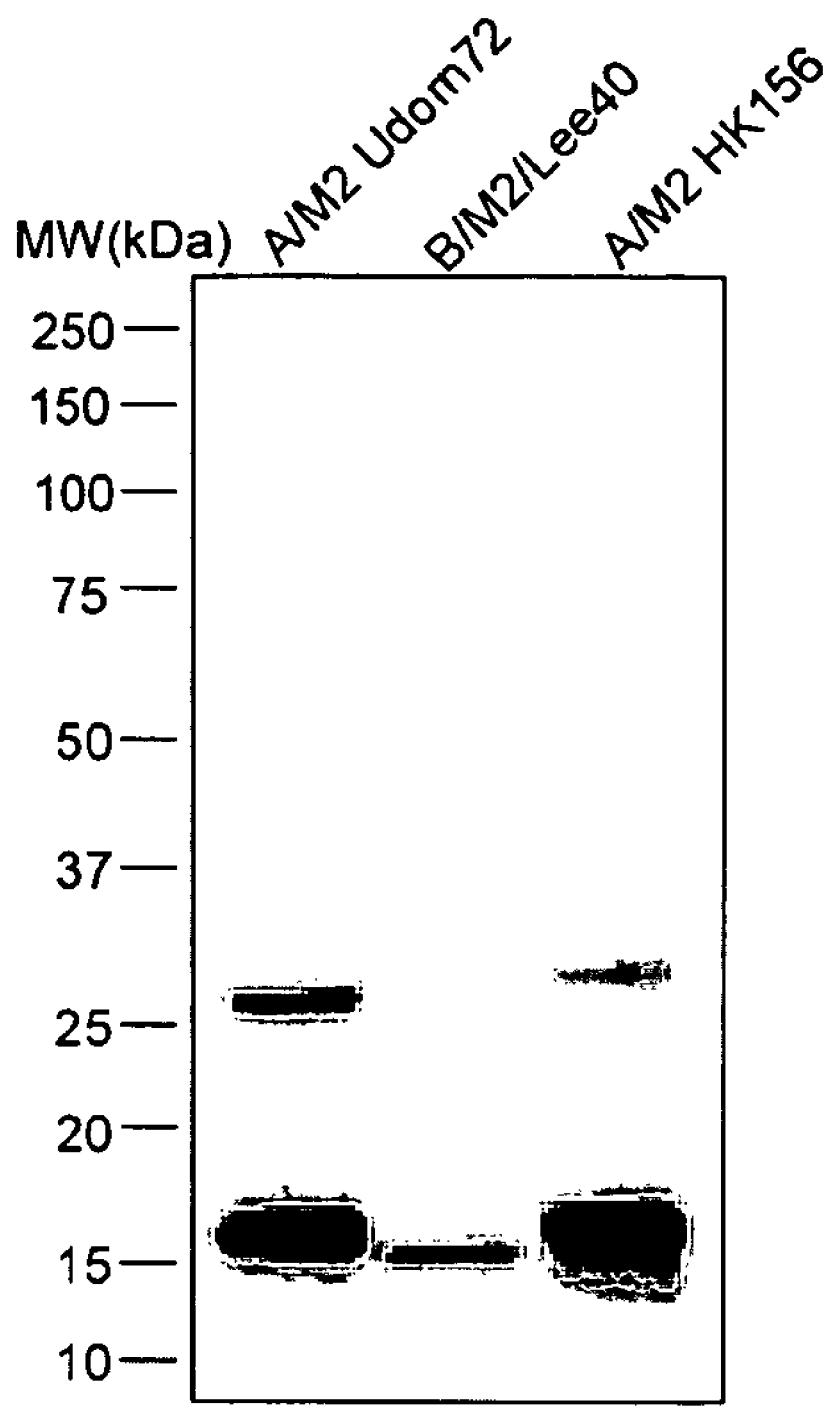

FIG. 27. M2 ion channels from various strains of Influenza A and B can be incorporated in purified VLPs. M2 ion channels were cloned by gene synthesis, and contained a C-terminal V5 epitope tag. VLPs with the M2 proteins were produced using MLV Gag, and incorporation of the 17 kDa M2 protein confirmed, after lysing VLPs, by Western blot analysis using an anti-V5 primary antibody and an HRP-conjugated anti-mouse secondary antibody. A 30 kDa M2 dimer is also apparent in lanes containing A/M2, which was expressed at higher concentrations than B/M2. The incorporation of other M2 channels into MLV-based VLPs were similarly confirmed, including A/M2/VN1194 and A/M2/PR8/34 (data not shown).

Figure 28:
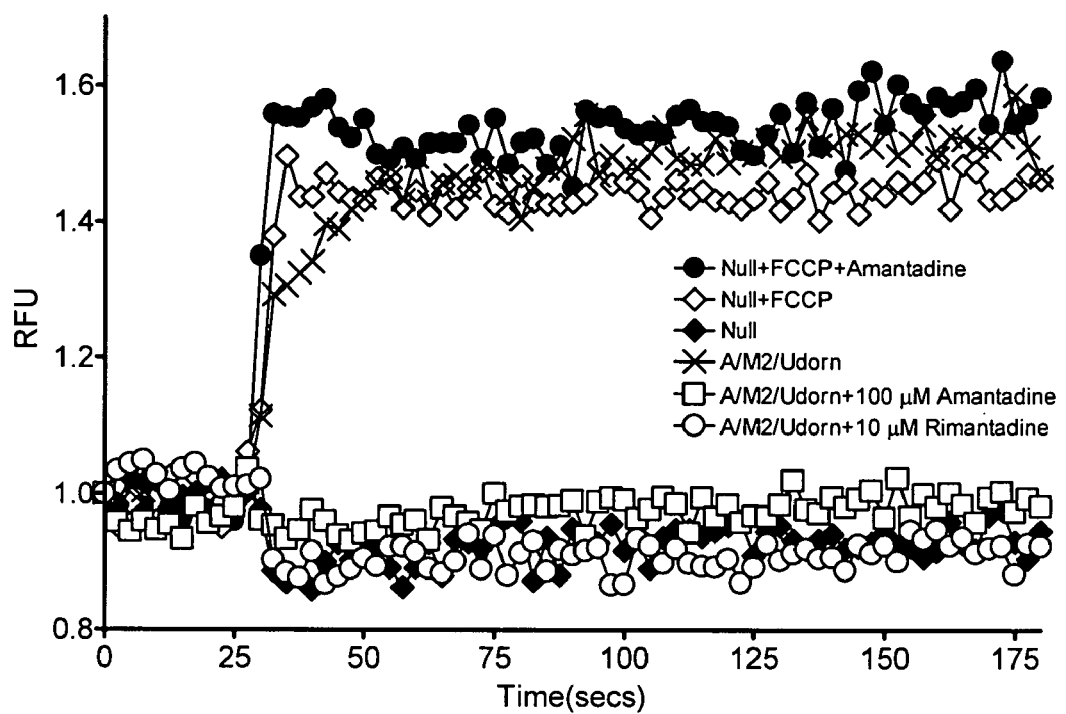

FIG. 28. Detection of M2 ion channel function and inhibition in VLPs. MLV VLPs incorporating A/M2 Udorn72 were produced and suspended in 10 mM HEPES pH 7.0/150 mM NaCl+0.2% FMP membrane potential dye ±amantadine (100 μM) or rimantadine (10 μM). VLPs were distributed across wells of a 384-well plate ($2.5 \times 10^6$ DLS counts/sec per well) and fluorescence monitored as MES buffer pH 4.5 was simultaneously added to each well to a final concentration of 30 mM. Relative fluorescence intensity values increased upon addition of MES, indicating $H^+$ transport across VLP membranes in VLPs containing A/M2, but not in those without M2 ion channel (null). VLPs not containing A/M2, but pre-treated with the protonophore FCCP, were used as a positive control. The inclusion of the specific M2 inhibitors, amantadine or rimantadine, in the assay buffer completely abrogated fluorescence signal associated with $H^+$ transportation, demonstrating its specificity for M2 function.

Figure 29:
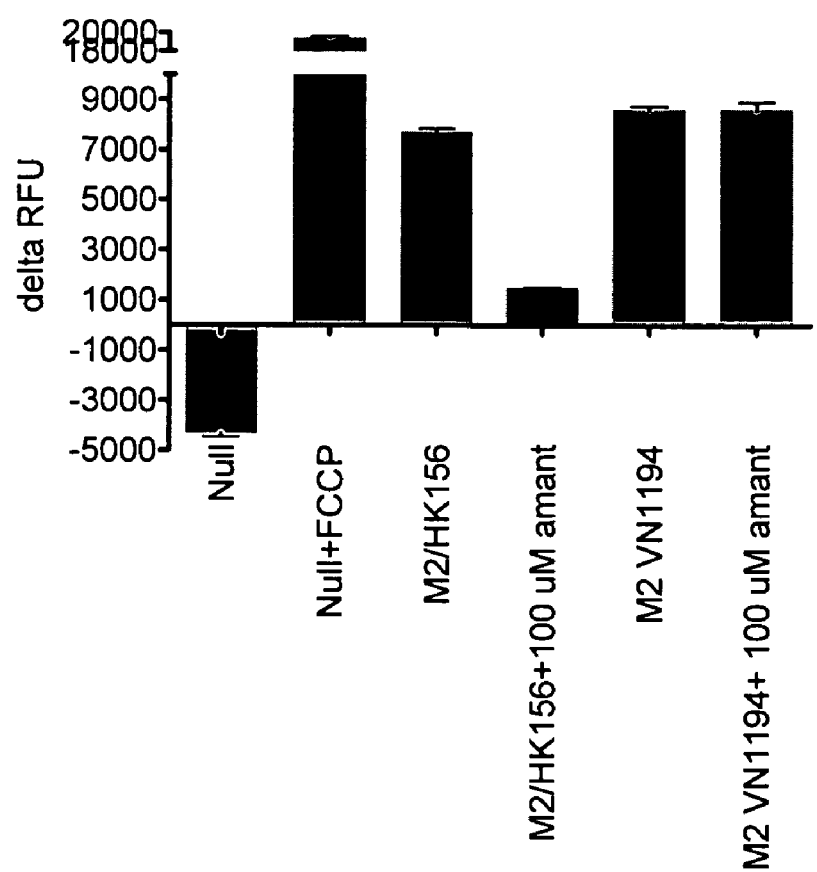

FIG. 29A. Transportation of H+ across VLP membranes is due to the specific activity of incorporated M2 ion channel. VLPs were suspended in 10 mM HEPES pH7.0/150 mM NaCl+1.0% FMP dye±100 μM amantadine and aliquotted in wells of 384-well plate ($5 \times 10^6$ DLS counts/sec per well). Fluorescence was monitored using a FlexStationII (Molecular Devices) during the addition of MES buffer pH 4.5. VLPs containing M2 from the amantadine-sensitive influenza A strain HK156/94 demonstrated an increase in fluorescence intensity, indicating $H^+$ transport by the M2 channel in the absence, but not in the presence of amantadine. VLPs incorporating M2 ion channel from the amantadine-resistant influenza A strain PR8/34 exhibited trans-membrane transportation of $H^+$ in the presence or absence of amantadine. However, VLPs incorporating A/M2 PR8/34 mutated to render it amantadine-sensitive (V27S31) exhibited $H^+$ translocation in the absence, but not in the presence of the drug. Null VLPs not containing any M2 ion channel were used as negative controls, while VLPs treated with the protonophore FCCP were used as positive controls. B. Detection of H+ transportation and inhibition in VLPs incorporating M2 ion channel from amantadine-sensitive and -resistant strains of Influenza. Translocation of $H^+$ across VLP membranes was assayed in 384-well microplates using a lipid-soluble membrane potential sensitive dye, FMP, as described. Fluorescence was monitored using a FlexStationII. VLPs ($5 \times 10^6$ DLS counts/sec per well) incorporating M2 ion channel from Udorn72, an amantadine-sensitive strain of Influenza A, were able to transport $H^+$ in the absence, but not in the presence of 5 μM amantadine. However, 5 μM of amantadine was not able to inhibit $H^+$ transport by VLPs incorporating A/M2 Udorn72 with a mutation (S31N) that renders it insensitive to amantadine, nor by VLPs incorporating M2 from Lee40, an influenza B strain that is naturally resistant to amantadine. VLPs not containing any M2 protein were used as a negative control, while VLPs pre-treated with the protonophore FCCP, were used as a positive control. C. Detection of M2 ion channel function and inhibition in VLPs. VLPs were suspended in 10 mM HEPES pH7.0/150 mM NaCl+1.0% FMP dye±100 μM amantadine and aliquotted in wells of 384-well plate ($5×10^6$ DLS counts/sec per well). Fluorescence was monitored using a FlexStationII (Molecular Devices) during the addition of MES buffer pH 4.5 to a final concentration of 30 mM. Transportation of $H^+$ across viral membranes, indicated by a change in fluorescence intensity (after correction for baseline values), was observed in the absence, but not in the presence of amantadine in VLPs containing M2 from HK156, an amantadine-sensitive strain of influenza A. The inclusion of amantadine did not, however, influence the transportation of $H^+$ across membranes of VLPs incorporating M2 from VN194, an amantadine-resistant strain of influenza A. VLPs containing no M2 were used as a negative control, while VLPs-pretreated with the protonophore FCCP were used as a positive control.

Figure 30:
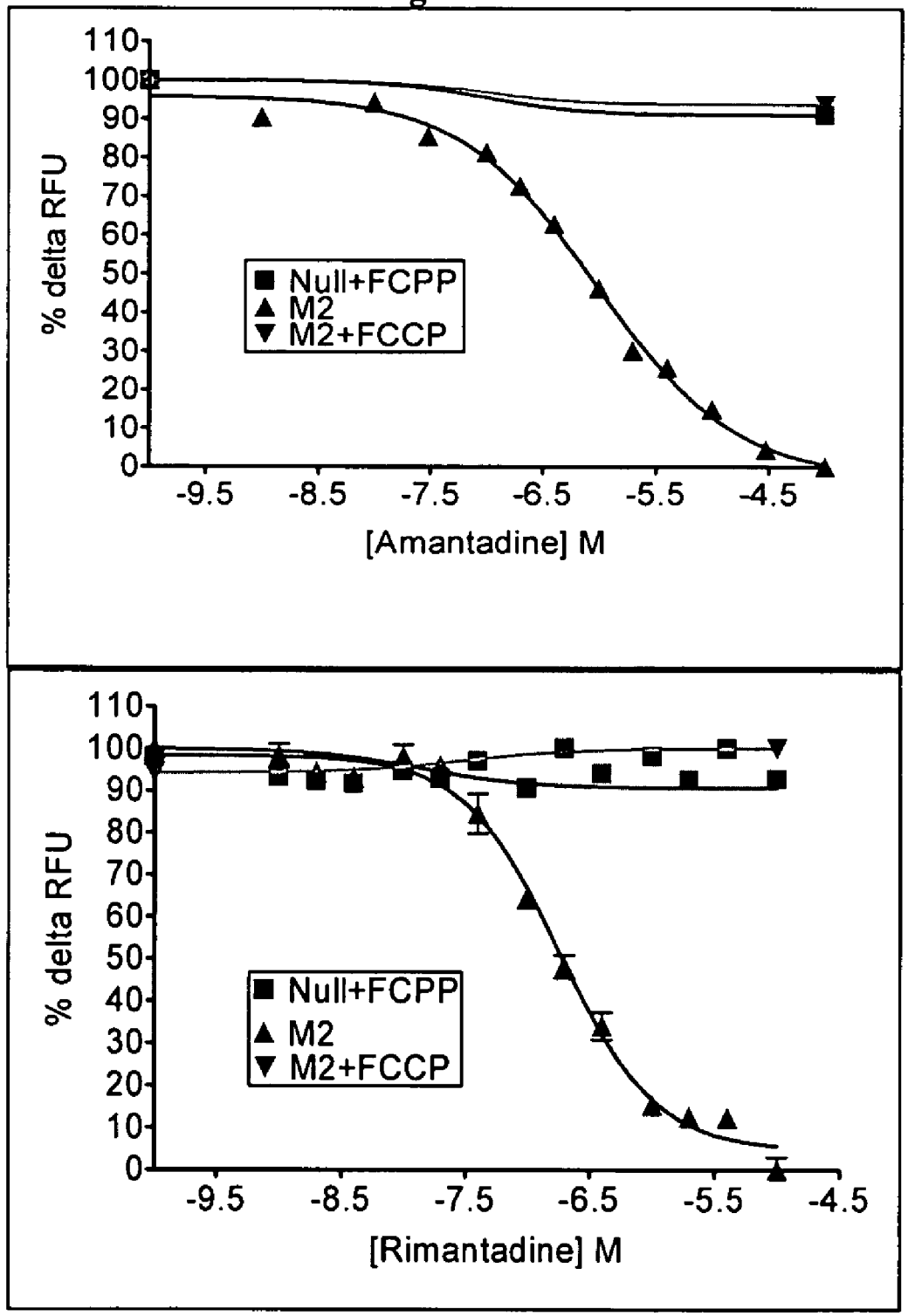

FIG. 30. Detection of M2 ion channel inhibition with amantadine and rimantadine in VLPs. VLPs ($5×10^6$ DLS counts/sec per well) were suspended in assay buffer containing 1% FMP membrane potential dye and the selective M2 inhibitors (A) amantadine (0.001-30 µM) or (B) rimantadine (0.001-10.0 µM). Fluorescence was monitored in triplicate wells using a FlexStationII during the addition of MES buffer (pH 4.5). The change in fluorescence intensities in triplicate wells, after normalizing raw fluorescence against baseline, was plotted against the negative log of the amantadine or rimantadine concentration to generate inhibition curves. Amantadine inhibited the movement of $H^+$ across membranes of VLPs containing M2 with an IC50 of 0.98 µM (Hillslope=−0.71). Rimantadine inhibited $H^+$ movement with an IC50 of 0.18 µM (Hillslope=−1.1). As expected, pre-treatment of VLPs with the protonophore FCCP rendered transmembrane $H^+$ movement resistant to abrogation by amantadine or rimantadine, supporting the specificity of their inhibitory effects on M2 in VLPs.

DETAILED DESCRIPTION OF THE INVENTION

The methods, modifications, and compositions disclosed herein can be applied to or incorporated into particles. As used herein, the term "particle" refers to any particle comprising a phospholipid layer comprising a viral core protein and at least one additional membrane-embedded polypeptide. The amino acid sequence, subunit of a protein, or protein components of the invention may be synthesized de novo by techniques well-known to those skilled in the art. The amino acid sequence, subunit of a protein, or protein components of the invention may also be encoded by nucleotide sequences endogenous to the viral or cell particle from which the article is derived. The amino acid sequence, subunit of a protein, or protein components of the invention may also be encoded by nucleotide sequences exogenous to the viral or cell particle from which the article is derived (i.e. not native to the cell or virus from which the particle is derived). Examples of particles include, but are not limited to, lipoparticles, enveloped viruses (e.g. influenza, baculovirus), and virus-like particles. Particles, such as lipoparticles, viruses, and virus-like particles, that incorporate membrane proteins are described in U.S. patent application Ser. No. 10/901,399, filed Jul. 28, 2004, which is herein incorporated by reference in its entirety. In some preferred embodiments, an additional protein is an ion channel polypeptide.

A "lipoparticle," as that term is used herein, means a small particle of about ten nanometers to about one micrometer, comprising an external lipid bilayer, a viral core protein, and at least one additional polypeptide that further comprises and ion channel polypeptide. Lipoparticles include enveloped virus-like particles. In some preferred embodiments, the lipoparticles are enveloped virus-like particles which comprise an enveloped viral core protein, a lipid bilayer, and an ion channel polypeptide. The lipoparticle may be about ten nm to about 500 nm, about 100 to about 500 nm, about 200 to about 400 nm, about 300 to about 399 nm, about 500 nm to about 1000 nm, about 600 to about 900 nm, or about 700 to about 800 nm. The lipoparticle does not encompass cell membrane vesicles, which are typically produced using empirical methods and which are usually heterogeneous in size. The lipoparticle also does not encompass liposomes, which typically lack core proteins that induce their formation. In some embodiments, the lipoparticle is dense, spherical, and/or homogeneous in size.

The lipoparticle is based on retrovirus structures and enables structurally intact cellular proteins to be purified away from the cell. Briefly, when a retrovirus is produced from a cell, the protein core of the virus buds through the membrane of the cell. As a consequence, the virus becomes enwrapped by the cellular membrane. Once the membrane 'pinches' off, the virus particle is free to diffuse. Normally, the virus also produces its own membrane protein (Envelope) that is expressed on the cell surface and that becomes incorporated into the virus. However, if the gene for the viral membrane protein is deleted, virus assembly and budding can still occur. Under these conditions, the membrane enwrapping the virus contains a number of cellular proteins.

In some embodiments, a lipoparticle comprises a multiple membrane spanning protein that spans the lipid bilayer at least twice. In some embodiments, the lipoparticle comprises a membrane protein that spans the membrane at least 3, at least 4, at least 5, at least 6, at least 7, at least 8, at least 9, at least 10, at least 11, at least 12, at least 13, or at least 14 times. The skilled artisan would understand, based upon the disclosure provided herein, that the invention encompasses a plethora of such complex proteins which traverse a membrane multiple times. Further, the invention provides a novel system comprising a lipid bilayer where one or more such proteins can interact to form, e.g., homo and/or heterodimers, or otherwise interact with other membrane proteins or itself similarly to such interactions in the native membrane where the proteins typically reside.

Multiple membrane spanning proteins include, but are not limited to, G protein-coupled receptors (GPCRs) (also known as 7-transmembrane receptors, $7^{TM}$) that span the membrane seven times, e.g., CCR5, CXCR4, CCR3, mu-opioid receptor, as well as transporters (proteins that transport molecules such as, but not limited to, amino acids or carbohydrates, across a membrane), ion channels, and the like.

As noted elsewhere herein, the invention encompasses a lipoparticle comprising a variety of membrane proteins, including combinations of proteins, which can form complexes when present in the lipoparticle. Such complexes include, but are not limited to, complexes of proteins that function together, e.g., CD4 and CCR5, CD4 and CXCR4, KCNQ2 and KCNQ3, hERG and MiRP1, and the like. The lipoparticle can comprise MCAT-1, an amino acid transporter that spans the membrane 14 times, and ion channels that span the membrane 6 times, e.g., K-channel KCNH2. All of these proteins have a similar feature: they span the membrane at least once. Many of these span the membrane multiple times.

In addition to these membrane proteins, which have been exemplified herein, other protein types and categories are encompassed in the invention and include, but are not limited to, the following: cytoplasmic domains of proteins (e.g., active conformations, G-protein coupling domains, kinase motifs of proteins such as EGF-receptor, and the like); organelle proteins (e.g., nuclear transporters, mitochondrial receptors, endoplasmic reticulum and Golgi membrane proteins); and multimeric complexes (e.g., dimers and trimers, viral envelope proteins, hetero-oligomers, and the like). More specifically, membrane proteins of the invention include, but are not limited to, GPCRs (e.g., CCR8, XCR1, CX3CR1, TAS2R38, TAS2R16, TAS2R4, TAS1R1, TAS1R2, TAS1R3), transporters (e.g., glucose transporter), ion channels (e.g., K-channel Kv1.3 tetramers), tetrameric Type II protein (e.g., DC-SIGN tetramers), tetraspanning membrane proteins (e.g. CD81), constitutively active GPCRs (e.g., HHV8 ORF74), viral proteins (e.g., HIV gp160, hepatitis C E1-E2 Envelope protein, expressed on endoplasmic reticulum membrane).

The ion-channel can be wild-type or have a modification, such as, for example, an insertion, deletion, substitution, or mutation. The modification can also be a post-translational modification, such as, for example, phosphorylation, glycosylation, and the like. The modification can also include the inclusion of an epitope tag or a fluorescent tag. The modification can also be a fusion protein such that the ion channel is fused in frame with another protein such as, for example, a fluorescent protein and the like. The ion channel can also be, for example, multimeric comprising one or more subunits. The multimer can be, for example, heteromeric or homomeric.

Lipoparticles can also comprise a GPCR (i.e. muscarinic acetylcholine receptor), G-protein subunits (e.g. Galpha, Gbeta, Ggamma), a GTP analog, an ion channel, or combinations thereof. In some embodiments, the ion channel is an inwardly-rectifying potassium channel, such as Kir3.x. A fluorescent dye (e.g. di-4-ANEPPS) can be loaded into this lipoparticle. In some embodiments, the dye fluoresces in a lipid environment and its fluorescence spectrum changes in response to fluctuations in membrane potential. The presence of the GPCR and the G-protein subunits in lipoparticles can be verified by Western blot using anti-G protein and anti-GPCR antibodies. One skilled in the art would recognize that alternative GPCRs, G proteins, and membrane potential-responsive fluorescent probes could also be used. To test their function, the labeled lipoparticles are exposed to a GPCR agonist. In some embodiments, stimulation of the GPCR causes dissociation of the G proteins from the GPCR and activation of the ion channel. The resultant movement of ions causes an alteration to the lipoparticle membrane potential, leading to a change in the fluorescence of the dye. In some embodiments, fluorescence emission is not altered in null-lipoparticles or in lipoparticles treated with a GPCR antagonist. Fluorescence can be measured in real-time before and after adding the agonist. Thus, lipoparticles can also be used to measure GPCR activation of ion channel activation.

Method of Generating the Lipoparticle of the Invention

Lipoparticles can be produced by any means. Examples of how to make lipoparticles can be found in, for example, US 2005/0123563A1, US2002/0183247A1, and WO2005042695, each of which is hereby incorporated by reference in its entirety.

One skilled in the art would appreciate, based on the disclosure provided herein, that the lipoparticle can comprise any membrane protein, i.e., any protein that typically is associated with a membrane. In some embodiments, the lipoparticle comprises a multiple membrane spanning protein. That is, the protein spans the membrane at least twice. Such multiple membrane spanning proteins encompass a wide plethora of membrane proteins including, but not limited to, the 7 transmembrane receptor proteins (e.g., G-protein coupled receptor proteins, GPCRs, which include chemokine receptors), ion channels, transporters (such as amino acid transporter MCAT-1, and the like). However, the lipoparticles may also comprise proteins that are targeted to the membrane by virtue of a signal peptide, whereas the protein would not normally be present at the membrane.

In other embodiments making a lipoparticle further comprises providing an additional component to the producer cell, whereby, upon formation of the lipoparticle, the lipoparticle comprises the additional component. The additional component may be any molecule which can be provided to the cytoplasm or the membrane of the producer cell. By way of example, the additional component may be a nucleic acid, an antisense nucleic acid, a gene, a protein, a peptide, Vpr protein, an enzyme, an intracellular antagonist of HIV, a radionucleotide, a cytotoxic compound, an antiviral agent, an imaging agent, or the like.

Inclusion of the additional component in the lipoparticle may be accomplished by directly coupling the additional component to the competent portion of the genome of the virus. For instance, if the competent portion of the genome is provided to the producer cell in the form of a plasmid, the plasmid may comprise a gene encoding an imaging agent or a reporter molecule, such as luciferase or green fluorescence protein. Inclusion of the additional component in the lipoparticle of the invention may also be accomplished by directly coupling the additional component to a nucleic acid encoding the membrane protein. For example, if the membrane protein is provided to the producer cell in the form of a DNA molecule encoding the same, an additional component comprising a protein may be provided to the producer cell by including the sequence of a gene encoding the protein in the DNA molecule, prior to provision thereof to the producer cell.

The additional component may also be provided directly to the membrane or the cytoplasm of the producer cell by, for example, including the additional component in the extracellular medium of the producer cell.

The present invention also provides for kits that comprise a lipoparticle comprising an ion channel, and/or compositions of the invention, a dye, a microplate, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention provides for kits for assessing the ability of an ion channel to signal. The kit comprises a lipoparticle comprising an ion channel, a stimulator of the ion channel, and a surface to which the lipoparticle can be attached.

In some embodiments, the kit comprises a lipoparticle attached to a substrate The substrate can then be examined using methods well known in the art to detect any change in the substrate mediated by or associated with the membrane protein present in the lipoparticle.

In some preferred embodiments, the kits of the present invention comprise a detection agent, such as a fluorescent dye or protein.

The present invention also provides for kits for identifying a potential ligand of an ion channel. The kit comprises a lipoparticle comprising an ion channel. In some embodiments, the kit comprises a lipoparticle that is attached to a surface and can also comprise a lipoparticle that is provided separately from the surface, which is also provided in the kit. In other embodiments, the kit further comprises a test ligand, or a plurality of such ligands, such as, but not limited to, a library of test ligands to be assessed for their ability to specifically bind with the membrane protein present in the lipoparticle.

The present invention also encompasses a kit where the lipoparticle is provided physically separated from a ligand and where the ligand is already bound with the lipoparticle. Similarly, the present invention encompasses a kit where the lipoparticle is provided physically separated from the surface, as well as a kit where the lipoparticle is provided attached to the surface. Further, the present invention also encompasses a kit with all possible permutations such that the ligand can be bound with the lipoparticle which is, in turn, attached to the surface, or each is provided separately, or any permutation thereof.

The present invention also provides for kits for identifying a compound that affects binding between a ligand and a protein (i.e., a receptor). The kit comprises a lipoparticle comprising a protein and a surface to which the lipoparticle can be attached. In some embodiments, the kit comprises a lipoparticle and a surface that are provided separately or where the lipoparticle is provided already attached to the surface.

In some embodiments, lipoparticles, viruses, or virus-like particles can be captured on surfaces for a variety of applications. Lipoparticles, viruses, or virus-like particles can be captured to surfaces by mixing the particles in solution with a capture agent, such as WGA-biotin, and then flowing or placing the particles over a suitable surface, such as avidin. Lipoparticles can also be captured using a membrane protein in the lipoparticle, such as a transmembrane-anchored avidin fusion protein or a fusion protein containing a His-tag, that allows attachment of the lipoparticle to a suitable surface such as biotin or $Ni^{+2}$ The present invention also relates to methods for spotting lipoparticles, virus-like particles, or viruses in an array format onto a solid surface without allowing the liquid to completely desiccate. In some embodiments, the spotting comprises including in the spotting medium trehalose, glycerol, sucrose, collagen, or gelatin. In some embodiments, the lipoparticles are dried or lyophilized.

In some embodiments, the present invention also provides methods of identifying channel openers or blocker comprising contacting a lipoparticle, virus, or virus-like particle comprising the ion channel with a library. In some embodiments, the library comprises more than one, more than 10, more than 50, more than 100, more than 1,000, more than 5,000, more than 10,000, about 500, about 1,000, about 5,000, about 10,000 potential openers or blockers. In some embodiments, the method comprises detecting the effect of the partner on the ion channel. In some embodiments, the library is a phage display library, ribosome display library, or chemical library. In some embodiments, the partner is a monoclonal antibody, a polyclonal antibody, an affinity-purified polyclonal antibody, a Fab fragment derived from a monoclonal antibody, an immunoglobulin-fusion protein, a single-chain Fv, an Fc-fusion protein, peptide, or polypeptide.

Lipoparticles Comprising Ion Channels and Methods Using the Same

Our ability to manipulate the interior and exterior ion concentrations of the particles enables ion channels in particles to be maintained in defined conformational states (i.e. open, inactivated, closed).

Techniques used to measure membrane potential in cells and vesicles (Montana, et al. (1989), Biochemistry, 28:4536-4539, Rohr, et al. (1994), Biophysical Journal, 67:1301-1315, Venema, et al. (1993), Biochim Biophys Acta, 1146:87-96) have been adapted for the measurement of membrane potential in viral particles. However, lipoparticles possess properties that may improve the versatility of membrane potential probes compared with what is achievable in cells. Lipoparticles, virus-like particles, and viruses can be loaded with much higher concentrations of dye (for increased sensitivity) than can be achieved with cells, in which overloading can produce artifacts from organelle interference and diminished cell health (Nicholls, et al. (2000), Trends Neurosci, 23:166-74, Plasek, et al. (1996), J of Photochemistry and Photobiology, 33:101-124, Zochowski, et al. (2000), Biol Bull, 198:1-21). Furthermore, dyes which are toxic to cells may be used with particles, allowing new and better dyes to be exploited. The ability to use "fast" dyes in particles could allow development of the system for new applications such as sub-cellular localization for microscopic imaging.

Additional changes in the composition of the particles could be introduced in order to facilitate ion channel measurement. Such changes can include changing the internal ion concentration, changing the membrane lipids, modulating fluorescent dye content, or modulating water content. For example, particles can be soaked in high potassium buffer for extended periods of time in order to equilibrate the internal content of the particles with the ion concentration of the outside buffer. Alternatively, the interior composition of particles can be equilibrated using electroporation (which opens transient pores in the viral membrane), enabling new methods of controlling virion interior ion concentration. Similarly, purified lipids can be added to suspensions of particles where the lipids will partition into the particle membrane.

A variety of detection formats can be used to detect fluorescent changes in membrane potential dyes. Cuvette-based monochromators such as the Perkin-Elmer LS-50B can be used. Alternatively, microplate-based fluorescence detectors such as the Wallac Victor2V and Molecular Devices FlexStationII and FLIPR-Tetra can be used. These detection devices are capable of detecting samples in 96, 384, and/or 1536-well microplates. In some cases, the detection devices permit ratiometric detection of two emitted or excited wavelengths. In order to capture signals generated quickly after addition, an automated injector is preferred to initiate the assay (e.g. the addition of high-K buffer to samples). In other cases, end point readings can be used to compare fluorescence before and after stimulation of the ion channels. Other detection devices, including stopped-flow detection devices, microfluidic flow-cells, and nano-wells, are also possible. For example, additional detection devices could also be used, including microfluidic devices, a 96-well plate, a 384-well plate, a 1536-well plate, a glass slide, a plastic slide, an optical fiber, a flow cytometer, a microscope, a fluorometer, a spectrometer, or a CCD camera. Alternative formats for ion channel detection within lipoparticles also include confocal-based detection (e.g. Evotec's FCS Opera system that detects nanometer-scale events within femtoliter volumes), FMAT (Applied Biosystems), CD-based microfluidic systems (e.g. from Gyros and Tecan), and increasingly sophisticated microfluidic components (e.g. from companies such as Micronics and Micronit). Other methods of detection can also be used, such as, for example, flow cytometry, confocal microscopy, fluorescent microscopy, and the like.

In some embodiments, microplates in 96- and 384-well format are used standard for cell-based assays, and are commonly used for screening large libraries of potential pharmaceutical agents. However, 1,536-well microplates can also be used. (Dunn, et al. (2000), J Biomol Screen, 5:177-88, Garyantes (2002), Drug Discov Today, 7:489-90), and advanced systems with 9,600 to 25,000 wells can also be used. Lipoparticles are ideally suited for these kinds of miniaturized formats because they can be dispensed and stored without affecting viability. Lipoparticles can also be used in further miniaturized systems because of the advantages of lipoparticles, which include, for example, their suitability to ultralow volume liquid handling and superior assay reproducibility at low volumes where cell numbers become limiting (a 25 nl volume holds only about 25 cells vs. $2.5 \times 10^6$ lipoparticles).

The level of fluorescence detected from membrane potential dyes or fluorescent probes can be calibrated to measure the absolute value of electrical membrane potential in mV. Absolute measurements are important as an internal control, for comparison of inhibitors, toxins, and new ion channels, and for comparison to others' results using different detection systems. The most widely used calibration procedure is based on membrane potential clamping to a potassium equilibrium diffusion potential. Saturating amounts (1 μM) of valinomycin are added at gradients of potassium solution from 0-150 mM. A calibration curve is plotted to correlate fluorescence to membrane potential, as calculated from the Nernst equation.

The present invention also provides methods of detecting cellular ion channel activity (e.g. voltage-gated, ligand gated, and the like) in particles. The present invention also provides methods of detection of viral ion channel activity within particles. In some embodiments, the detection of ion channel activity within particles can be used for drug discovery to identify compounds that can modulate the ion channel activity. Any drug discovery method can be used including those described herein.

In some embodiments, gag-GFP is used to measure ion channel activity by measuring the change in fluorescence of the GFP molecule that is incorporated into the particle.

In the present invention, the particles comprise ion channels and are used to measure function. When making lipoparticles, contaminants of unwanted proteins may also be included in the lipoparticles. In some embodiments, to avoid the contaminating proteins from having undesired effects on how one uses the lipoparticles, the lipoparticles can be contacted with inhibiting toxins and/or blockers to inhibit the contaminating proteins. The contaminating protein inhibiting toxin and/or blocker is selected so that it does not inhibit or affect the protein(s) that are desired to be present in the lipoparticle.

In some embodiments, a virus, lipoparticle, or virus-like particle can be used to measure ion channel function. For example, viruses such as influenza contain ion channels (e.g. M2) and the methods described herein can be used assess the function of virally encoded ion channels and transporter proteins in a virus, lipoparticle, or virus-like particle. In some embodiments, the ion channel is a viral ion channel.

In some embodiments, the ion channel protein is a neurotransmitter receptor.

The particles of the present invention can also be modified such that the modified particle can be used to detect ion channel protein function. The modifications can be any modification that results in a parameter that can be measured, quantified, visualized, and the like. Examples of modifications that can be made to particles include, but are not limited to, modifying the membrane lipid composition, modulating the fluorescent dye content of the particles (e.g. adding fluorescent dyes), modulating the water content of the particle, and modulating the ion content of the particle. In some embodiments, a change in the detectable agent can indicate an increase in protein function. In some embodiments, a change in the detectable agent indicates a decrease in protein function.

The fluorescent dyes can be used to monitor, visualize and/or measure protein function. For example, when an ion channel is activated, the dye can either flow into or out of the particles, which would indicate, in some embodiments, that proteins are functioning. Similarly, when an ion channel is activated, an ion or molecule can either flow into or out of the particle and interact with a dye either inside or outside or in the membrane of the particles, which would indicate, in some embodiments, that the proteins are functioning. The amount of dye and the fluorescent signal that is generated can be used to determine the level of activity of the ion channel.

The present invention also provides for methods to determine membrane protein function using particles comprising the membrane protein. In some embodiments, the particles comprise an ion channel and a detectable agent. The detectable agent can be any agent that can be detected by any means. For example, the agent can be detected using fluorescence, radioactivity, ultra-violet light, or visual light. Examples of detectable agents include, without limitation, voltage-sensitive fluorescent dyes and ion-sensitive fluorescent dyes.

As used herein, the term "voltage-sensitive fluorescent dye" refers to a dye that fluoresces or changes its fluorescent properties in response to a change in voltage.

As used herein, the term "ion-sensitive fluorescent dye" refers to a dye that fluoresces or changes its fluorescent properties in response to a change in ion concentration.

Examples of voltage-sensitive fluorescent dyes include, but are not limited to, di-4-ANEPPS($C_{28}H_{36}N_2O_3S$), di-8-ANEPPS, rhodamine 421, oxonol VI, JC-1, DiSC3(5), CC2-DMPE, DiSBAC2(3), DiSBAC4(3), VABSC-1, DiSBAC(1)$_3$, FMP-Blue™, FMP-Red™, and the like (Molecular Probes, Inc.). Examples of ion-sensitive dyes include, but are not limited to, Fura-2, Fluo-3, Rhod-2, Fura-C18, Fura-FF-C18, Calcium Green C18, Mag-indo-1, Mag-fura-2, FluoZin-1, FuraZin-1, Phen Green FL, NewportGreen, Nitrophyl EGTA, DMNP-EDTA, Diazo-2, BAPTA, TPEN, SNARF-1, SBFI, PBFI, SPQ, MQAE, MEQ, lucigenin L-6868, and their AM-esters (Haugland (2003)).

Examples of other useful membrane potential sensitive dyes include the membrane potential-sensitive dye selected from the group consisting of HLB 021-152, HLB 021-155, HLB 007-054, HLB 021-149, HLB 004-111, HLB 007-052, HLB 028-008, HLB 004-078, HLB 004-183, and combinations thereof.

The choice of which detectable agent is used is not essential and depends on the use of the particles. A plethora of fluorescent dyes and probes exist for detecting the function of ion channels, ranging from ion-specific dyes to dyes that respond to changes in membrane potential (Molecular Probes Handbook (2002)).

Of the more than two dozen different membrane potential dyes available, examples include, but are not limited to, the ANEPPS dyes, di-4-ANEPPS and di-8-ANEPPS. Both ANEPPS dyes have identical fluorophores, exhibit good photostability, low toxicity, and a fairly uniform 10% per 100 mV changes in fluorescence intensity (Molecular Probes Handbook (2002), Rohr, et al. (1994), Biophysical Journal, 67:1301-1315). Due to its longer alkyl chains, di-8-ANEPPS is better retained in the membrane, slightly more photostable, and less phototoxic, but also more difficult to work with. Both ANEPPS dyes are essentially nonfluorescent in aqueous solutions but have absorption/emission maxima of 467/631 nm when bound to lipid membranes. Di-4-ANEPPS can be incorporated into lipoparticles. Further, the ANEPPS dyes can be measured ratiometrically, responding to increases in membrane potential with a decrease in fluorescence excited at approximately 440 nm and an increase in fluorescence excited at 530 nm. Ratiometric measurements between +120 mV and −120 mV are linearly responsive to membrane potential using ANEPPS dyes.

A number of alternative dyes are also available that can measure membrane potential, (Molecular Probes Handbook (2002), Plasek, et al. (1996), J of Photochemistry and Photobiology, 33:101-124, Smith (1990), Biochim Biophys Acta, 1016:1-28). These dyes include but are not limited to the following.

Oxonol VI. Lipophilic anionic dyes such as the oxonols can detect relatively large changes in membrane potential which occur over periods of several minutes. In addition to the traditional use of oxonol to detect absolute changes in fluorescence, a ratiometric method has been developed using a fluorescence resonance energy transfer mechanism based on reactivity between oxonol and fluorescently labeled lipids (González, et al. (1995), Biophysical Journal, 69:1272-1280). This approach reportedly can sense fast potential changes with fluorescence changes that exceed 50% per 100 mV JC-1. JC-1 is a carbocyanine fluorescent dye that forms aggregates upon depolarization and can be measured ratiometrically. Aggregation within the confined membrane interior results in decreased fluorescence and maximal emission shifts from 527 nm to 590 nm. The dye has been used successfully in many experiments, but is noted by some to exhibit unacceptable variability.

DiSC3(5). For many years, DiSC3(5) was considered to be the dye of choice for membrane potential assays due its high sensitivity, 50-80% per 100 mV (the highest of all cyanine dyes). This high signal is unavoidably related to the dye's high accumulation in cells, and thus to its high toxicity, but the toxicity should not effect signal within lipoparticles. Depending on the environment of use, DiSC3(5) may be assayed ratiometrically, increasing signal-to-noise.

Rhodamine 421. RH 421 has yielded the most sensitive response recorded for a fast potentiometric probe, greater than 20% fluorescence change per 100 mV. The optimal excitation and emission from RH 421 is dependent on its environment.

The properties of some fluorescent dyes that can be used to measure membrane potential are listed in Table 1. Other detectable agents include, but are not limited to fluorescent probes (e.g. fluorescent proteins, fluorescent amino acids, or fluorescent lipids). In some embodiments, the detectable agents can be used to make a ratiometric measurement to determine the function of the membrane protein.

TABLE 1

Table 1: Fluorescent dyes are listed. Dyes were selected from more than two dozen fluorescent dyes that are responsive to membrane potential (Molecular Probes Handbook (2002), Rohr, et al. (1994), Biophysical Journal, 67: 1301-1315).

| Category | Dye | Ratiometric | Advantages/Disadvantages |
| --- | --- | --- | --- |
| Fast | Di-4-ANEPPS | yes | Fast response (msec)/ |
|  | Di-8-ANEPPS | yes | Low signal (10%/100 mV) |
|  | Rhodamine 421 | no |  |
| Slow | Oxonol VI | yes | Slow response (sec-min)/ |
|  | JC-1 | yes | High signal (100%/100 mV) |
|  | DiSC3(5) | yes | Slow dyes noted for variability of response |

As used herein the term "ratiometric measurement" refers to the ratio of at least two measurements that are used to create a ratio. For example, di-4-ANEPPS responds to an increase in membrane potential with a decrease in fluorescence excited at approximately 440 nm and an increase in fluorescence excited at 530 nm. By measuring the emission wavelength at 630 nm, the 440/630 response can be divided by the 530/630 response to produce a ratio measurement.

As with all methods described herein, a computer can be used to calculate and measure the detectable agent, and calculate and determine the ratiometric measurement, and the like.

When using fluorescent detectable agents, one can measure the function of the membrane protein by resonance energy transfer (FRET). Resonance energy transfer is well known to one of ordinary skill in the art. For example, two separate fluorescent species can interact and they generate a distinct and different fluorescent signal. The distinct signal can be used to determine the function of the membrane protein.

In some embodiments, the present invention provides for methods of identifying inhibitors or stimulators of proteins (e.g. GCPRs, ion channels, transporter proteins and the like) comprising measuring changes in detectable agents. A particle comprising a membrane protein (e.g. ion channel) and a detectable agent will generate a detectable signal when the protein is active or inactive. The particle can be contacted with a test compound and a change in the detectable signal indicates that the compound is either an inhibitor or a stimulator. The change in the detectable signal could be a complete inhibition of the detectable signal (e.g. the signal is no longer detectable) or the detectable signal may be reduced. In some embodiments, the detectable signal may increase. Examples of test compounds include but are not limited to, proteins, peptides, amino acids, organic molecules, antibodies, nucleic acids, inorganic compounds, and the like.

The present invention also provides for methods for identifying inhibitors of a known stimulator of a membrane proteins (e.g. GCPRs, ion channels, or transporter proteins) within a particle comprising contacting the particle with the stimulator and the potential inhibitor. In some embodiments, the potential inhibitor and stimulator are contacted concurrently. In some embodiments, the potential inhibitor is contacted with particle before or after the stimulator is contacted with the particle. This method can be used, for example, to test antagonists of known ligands of GCPRs, ion channels, and neurotransmitters. In some embodiments, instead of an inhibitor, an agonist is used to determine what effect the agonist has on the function of the membrane protein.

As used herein, the term "inhibitor" refers to a compound, peptide, or protein that inhibits the function of a protein. In some embodiments, the inhibitor is an antibody or fragment thereof.

Toxins are known to bind membrane proteins. Some toxins can only bind when the membrane protein is in a certain conformation or active state. Therefore, in some embodiments, the present invention provides methods of confirming membrane protein conformation by binding a toxin to a lipoparticle containing an ion channel comprising contacting the particle with the toxin. In some embodiments, the ability of the toxin to bind to the membrane protein indicates the structure or active state of the ion channel. The binding status of the toxin can also be used to determine that the membrane protein has properly folded and presented in the correct conformation on the surface of the lipoparticle. Therefore, this can be used in some embodiments as a quality control test to determine the structure and folding of a membrane protein in a lipoparticle.

The present invention also provides for methods of measuring membrane protein function comprising the steps of microinjecting particles to a location and measuring the function of the membrane protein. The location can be, for example, an intracellular compartment, an organelle (e.g. mitochondria), the cell surface, gap junctions, or a synapse. Once the particle is microinjected into its location, the particle can be used to detect membrane protein function. The particle can be used to detect the function of the membrane proteins within the particle and the particle can also be used to detect changes in the environment (e.g. ion concentration) of its surroundings. For example, if the ion concentration of the environment in which the particle has been injected into changes, a particle comprising an ion channel and a fluorescent dye can be used to detect this change. The change in ion concentration can, in some embodiments, open the ion channel allowing the signal generated by the fluorescent dye to increase, or in some embodiments, decrease, thereby indicating a change in the location. The particle comprising an ion channel can be used to detect the change in ion concentration or membrane potential. As with all the methods described herein, in some embodiments, the measured function of the ion channel is the absolute level. This can involve calibrating the particles to a calibration standard. Examples of a calibration standard include, but are not limited to, ionophores. When used with known molar amounts of a specific ion (e.g. potassium), the ionophore allows the ion to permeabilize the membrane, as measured by a 100% signal. By knowing the ion concentration and using the Nernst equation, the 100% signal can be converted to millivolts of membrane potential. The signal measured experimentally can then be calibrated to absolute units (e.g. millivolts).

As used herein, the term "absolute level" refers to the quantity of a substance as measured in units that represent the level of the substance, independent of experimental measurement. Units of absolute levels can be in molar or millivolts. For example, the membrane potential of a typical living cell in absolute units is approximately −70 mV.

The present invention also provides for kits for assessing the function of an ion channel, wherein the kit comprises a particle comprising a desired membrane protein and a protocol for assaying function.

The present invention facilitates the detection of ion channel function within a nano-scale sensor. The ability to sense ion channel function within a nano-scale sensor using particles has many applications, including, for example, microfluidic drug screening, and subcellular detection.

Nanometer-sized sensors of ions and voltage can also be used to probe subcellular structures during physiological responses. For example, neurons can be monitored under conditions in which they are activated. Moreover, the probes that can be constructed are not limited to sensing changes, but can be calibrated to detect absolute levels of ions and voltage, allowing local measurements of important, but inaccessible, structures.

As used herein, the term "array" refers to one or more compositions placed in an array format in or on a particular surface or in a container. For example, the composition can be placed onto a flat surface that has no wells. Alternatively, the composition can be placed within a well, where the wells are arranged in an array format. Examples of surfaces or containers include, but are not limited to, chips, slides, microplates, multi-well plates, microplate well, and the like. In some embodiments, the array is a microarray. A "multi-well plate" can be a plate with actual wells built in or a slide that is used for spotting compositions onto the slide as if there were wells. An "array within a microplate well" is, for example, when a well in a 96-well plate is spotted with more than one spot. This can also be referred to as an "array-within-array." The array can be any size, for example, standard plate sizes are 8×12, 16×24, 32×48. For array-within-array, standard sizes of the array (within each well) are, for example, 2×2, 3×3, 4×, 4, 5×5, 6×6, 8×8, 10×10. Arrays can also be based on pin configurations, with 2-4 rows of 4-12 pins each typical. Each touch of the pinhead can print multiple spots. In some embodiments arrays are often 100-300 spots per slide. In some embodiments, arrays can be 2,000-5,000 spots per slide. High density arrays can be, for example, 10,000-25,000 spots per slide or even higher. In some embodiments, the array will comprise 100 to 5,000 spots.

Definitions

Certain terminology that is used herein as follows.

The articles "a" and "an" are used herein to refer to one or to more than one (i.e., to at least one) of the grammatical object of the article. By way of example, "an element" means one element or more than one element.

The term "about", as used herein when referring to a measurable value is meant to encompass variations of ±10% from the specified amount.

As used herein, the term "membrane potential-sensitive dyes" can also be referred to as voltage-sensitive dyes or probes, potentiometric dyes or probes, and the like.

As used herein, a prefix to the term "lipoparticle" designates a specific membrane protein or other specific modification made to that lipoparticle. For example, "CXCR4-lipoparticle" is defined as a lipoparticle comprising the seven-transmembrane receptor CXCR4; "Gag/GFP-lipoparticle" is defined as a lipoparticle comprising a Gag/GFP fusion protein; "Gag/GFP-CCR5-lipoparticle" refers to a lipoparticle comprising a Gag/GFP fusion protein and the transmembrane receptor CCR5.

A "null-lipoparticle" is defined as a lipoparticle vehicle containing no specific membrane proteins. As used herein, "no specific membrane protein" means that a user has not specified a particular membrane protein to be incorporated into the lipoparticle. "Null-lipoparticles" can still comprise membrane proteins that naturally occur on the surface of the cell from which the lipoparticle was produced.

As used herein, the term "ion channel polypeptide" includes all ion channel proteins and fragments of proteins thereof. It includes voltage-gated, non-gated, ligand-gated, viral ion channels, and any ion channel with an open or closed conformation.

As used herein, the term "signaling component" refers to a reporter which allows an event to be detected or monitored.

"Virus," as the term is used herein, refers to a particle comprising a complete viral genome and the proteins encoded by that genome in their native state.

By the term "applicator" as the term is used herein, refers to any device including, but not limited to, a hypodermic syringe, a pipette, and the like, for attaching a lipoparticle and/or composition of the invention to a surface, including a sensor surface. Further, the applicator can be used to contact a ligand and/or a test compound with a lipoparticle.

The term "overexpressed" as used herein, refers to a level of protein expression that is greater than what is measured in a standard cell line. In some embodiments, a protein is overexpressed at least two times, at least three times, at least five times, at least 10 times, at least 100 times the level of standard cell line. The standard cell line can be any cell line that expresses the protein of interest. Examples of standard cell lines are mammalian cells, mouse cells, human cells such as, but not limited to HeLa cells, 293 cells, primary cells, stem cells, and the like.

The term, "cellular protein" is used to refer to a protein normally encoded by the cell and not viral DNA. However, the term also applies to a protein expressed by a recombinant virus wherein a cellular nucleic acid encoding the protein has been inserted into the genome of the recombinant virus for expression therefrom. Furthermore, the term also applies when the protein is provided to a virus or a virus vector in the form of a protein or a peptide.

The term "cell" refers to any type of living cell. Cells of both unicellular and multicellular organisms are included. Examples of cells include, but are not limited to, human cells, animal cells, mammalian cells, avian cells, stem cells, primary cells, hybridoma cells, vertebrate cells, invertebrate cells, insect cells, and the like. As used herein, the term "primary cells" refers to cells that are taken from tissues of an organism and are not immortal. Cells can also be immortalized cells, cancer cells, and the like, and cells that have been immortalized. To immortalize a cell is well known to those of skill in the art.

The term "virus-infected cell" refers to a cell which has been infected by a virus which comprises a viral protein including, but not limited to, a viral structural protein in its outer membrane.

As used herein, the term "organelle targeting sequence" refers to a peptide sequence that when fused with a second peptide sequence directs the second peptide sequence to a particular organelle. In some embodiments, an organelle targeting sequence targets a protein to the endoplasmic reticulum or the golgi apparatus.

As used herein, the term "gated" refers to a membrane protein whose opening and closing is governed by external conditions such as bound proteins or chemicals (e.g. neurotransmitters or hormones), membrane potentials, mechanical means (e.g., vibration or pressure), light, and the like.

As used herein, the term "non-gated" refers to a membrane protein that does not require specific stimuli to conduct ions.

Ion channels in the open and inactivated conformations contain pores in the open conformation, but the inactivated ion channel conformation cannot conduct ions.

As used herein, the term "ionophore" refers to a compound that facilitates transmission of an ion across a lipid barrier by combining with the ion or by increasing the permeability of the barrier to it.

As used herein, the term "inactivation gate" refers to a part of an ion channel that when closed prevents the channel from conducting ions For example, a voltage-gated ion channel is opened by a change in membrane potential. After a period of time in the open conformation, the inactivation gate closes and prevents the channel from conducting ions again until the inactivation gate opens. This is sometimes referred to as the "refractory" period.

As used herein, the term "contaminating protein inhibiting toxin" and "contaminating protein inhibiting blocker" refers to either a toxin or a blocker that inhibits the activity of a contaminating membrane protein (e.g. ion channel). "Contaminating protein" refers to a membrane protein whose presence is undesirable. The contaminating protein does not have to be identified before a contaminating protein inhibiting toxin or blocker is used. The "contaminating protein inhibiting toxin" and "contaminating protein inhibiting blocker" does not inhibit or interfere with the membrane proteins that are desired.

As used herein, the term "membrane potential" refers to an electrical potential difference between internal and external compartments separated by a lipid bilayer. The compartments can be the interior and exterior of a cell, separated by a cell membrane. The compartments can also be the interior and exterior of a lipid vesicle separated by a lipid bilayer of defined composition. The compartments can also be the interior and exterior of a virus or virus-like particle separated by a lipid membrane.

As used herein the term "low-molecular weight organic compound" refers to compounds having a molecular weight less than 3,000. A "low-molecular weight organic compound" can also refer to a compound having a molecular weight less than 1,000.

The term "membrane protein" includes proteins that span the lipid membrane surrounding a cell, so part of the protein is inside the cell and part of the protein is outside the cell. "Membrane protein" can also include proteins that span a lipid bilayer that is not part of a cell. "Membrane protein" also refers to a membrane spanning protein, a multiple membrane spanning protein, an intracellular membrane protein, an extracellular membrane protein, an organelle membrane protein, and the like. "Membrane protein" also refers to a protein that is attached or linked to a membrane, but does not span the membrane. A "membrane protein" can also be referred to as a "transmembrane protein".

The term "membrane protein" can also refer to a protein which is expressed within the lipid bilayer cell surface membrane of a cell. In the case of a cellular membrane protein, said protein is encoded by the cell and, at least under certain conditions, is associated with the outer surface of the membrane of the cell. In the case of non-cellular membrane proteins, the proteins may be derived from a source other than the cell expressing the protein, such as a virus, bacteria, yeast, or pathogen. A membrane protein may be a full-length protein, as encoded by a normal cell, or may be a fragment thereof. In some embodiments, the membrane protein is monomeric or multimeric.

A "membrane spanning protein," as the term is used herein, refers to a polypeptide that spans the cell membrane at least once. That is, the peptide is typically present in a cell membrane where it spans the lipid bilayer at least once.

As used herein, the term "1-TM" refers to a membrane protein that spans a membrane once. Examples of proteins that can be referred to as "1-TM" include, but are not limited to, CD4, Tva, EGFR, and the like.

"A multiple membrane spanning protein," as the term is used herein, is a polypeptide that spans the cell membrane at least twice. That is, the peptide is typically present in a cell membrane where it spans the lipid bilayer at least twice. A multiple membrane spanning protein also refers to peptide that spans the lipid bilayer at least three times, at least four times, at least five times, at least six times, at least seven times, at least eight times, at least nine times, or at least ten times. A multiple membrane spanning protein also refers to a peptide that spans the lipid bilayer three times, four times, five times, six times, seven times, eight times, nine times, or ten times.

"An intracellular membrane protein," as the term is used herein refers to a protein that is located inside the cell and is associated with the plasma membrane but does not span it. Examples of intracellular membrane proteins include, but are not limited to farnesylated proteins, lipid modified proteins, such as Ras, Src, kinases that associate with lipids, such as Protein Kinase C, and PI3-Kinase, and any other protein that is associated with intracellular side of the plasma membrane. An intracellular membrane protein can also refer to a membrane protein located on a membrane within the cell, such as, for example, in the endoplasmic reticulum, golgi, nucleus, mitochondria, and the like.

As used herein "associated with the plasma membrane" refers to a protein that is either covalently attached to the plasma membrane, but does not span it, or a protein that interacts through other bonding forces, such as polar and ionic bonds, with a molecule that is a part of the plasma membrane.

"Extracellular membrane protein," as the term is used herein refers to a protein that is located outside the cell and is associated with the plasma membrane, but does not span the plasma membrane.

As used herein, "an organelle membrane protein" refers to a protein that is either associated with an organelle membrane or spans the membrane of an organelle. Examples of organelle membranes include, but not limited to, golgi membranes and endoplasmic reticulum membranes.

"Exogenous protein" as the term is used herein refers to a protein not normally found in a specific cell type. For example, a human protein that is introduced into a mouse cell.

As used herein, the term "retention signal" refers to a signal that causes a compound to be retained at a specific location within the cell. In some embodiments the signal is a peptide or polypeptide. In some embodiments the retention signal retains a protein to the endoplasmic reticulum, nucleus, or golgi apparatus.

The term "ligand" refers to a substance (chemical or protein) that binds to a protein.

The term "ligand," as used herein, encompasses any protein or compound that can bind with a protein present in a lipoparticle. The ligand encompasses a protein or non-protein compound that can bind with a protein present in a lipoparticle. The term "ligand" can also be referred to as a "binding partner." In some embodiments, a "binding partner" can also be a monoclonal antibody, a polyclonal antibody, an affinity-purified polyclonal antibody, a Fab fragment derived from a monoclonal antibody, an immunoglobulin-fusion protein, a single-chain Fv, an Fc-fusion protein, peptide, polypeptide, and the like.

As used herein, the term "test ligand" refers to a ligand that is tested to determine if it binds to a lipoparticle comprising a protein. "Test ligand" can also refer to a ligand that is tested to determine if it inhibits the binding of another ligand to a lipoparticle comprising a protein.

As used herein, the term "test sample" refers to a sample that comprises a ligand, test ligand, and the like. Examples of test samples include, but are not limited to, blood, saliva, serum, cell lysate, organ lysate, tissue homogenate, animal secretions, vaginal secretions, feces, cell culture medium, and the like. In some embodiments, the test sample is diluted or concentrated, or dissolved with another solvent.

The term "receptor" refers to a protein, often a membrane protein, which binds to a ligand of biological significance and transmits the information so that it can influence cellular behavior.

The term "pseudotype" refers to an enveloped virus that does not comprise its natural or native envelope protein, which has been replaced by the envelope protein of another virus or another strain of the same virus.

The term "enveloped virus" refers to a virus comprising an envelope protein and a lipid bilayer.

The term "non-enveloped virus" refers to a virus that does not comprise an envelope protein or a lipid bilayer.

As used herein, the term "induced cell" refers to a cell that has been treated with an inducing compound that affects the cell's protein expression, gene expression, differentiation status, shape, morphology, viability, and the like. An induced cell can also be referred to as a "modified cell", a "selected cell," a "treated cell," and the like.

As used herein, the term "quaternary structure" refers to the way the subunits fit together. In some embodiments, "quaternary structure" refers to the way polypeptide subunits fit together or form oligomers. In some embodiments the quaternary structure is a homo-oligomer. In some embodiments the quaternary structure is a hetero-oligomer. In some embodiments the quaternary structure comprises a dimer, a trimer, a tetramer, and higher-order oligomers.

As used herein, the term "growth property" refers to the division of a cell. Examples of defects in growth properties include, but are not limited to, hyperplasia, neoplasia, metaplasia, cancer, and the like. Examples of cancer, include, but are not limited to breast cancer, colon cancer, lung cancer, skin cancer, brain cancer, leukemia, multiple myeloma, cervical cancer, uterine cancer, ovarian cancer, prostate cancer, head and neck cancer, bladder cancer, pancreatic cancer, liver cancer, and the like.

As used herein, the term "ion-conductance property" refers to a cell's ability to modulate the ion conductance or the ion concentration of the cell. In some embodiments, a defect in ion-conductance is due to a defect in an ion channel protein.

As used herein, the term "signaling property" refers to the cells ability to transmit signals throughout the cell. In some embodiments, the signaling property refers to a signal that originates from a membrane protein and is transmitted inside the cell, the nucleus, or other cytoplasmic compartment (e.g. mitochondria, golgi apparatus, and the like).

As used herein, the term "mutation" refers to a protein that has at least one amino acid mutated or changed to another amino acid residue.

As used herein, the term "deletion" refers to a protein that has at least one amino acid residue removed as compared to the wild-type sequence. In some embodiments at least 2, at least 5, at least 10, at least 20, at least 50, or at least 100 amino acid residues are removed. The residues that are removed can also be contiguous.

As used herein, the term "insertion" refers to a protein that has at least one amino acid residue inserted into the wild-type sequence. In some embodiments at least 2, at least 5, at least 10, at least 20, at least 50, at least 100 amino acid residues are inserted. In some embodiments about 1, about 2, about 5, about 10, about 20, about 50, about 100, or about 150 amino acid residues are inserted. In some embodiments about 1 to about 100, about 1 to about 50, about 1 to about 30, about 1 to about 10, about 5 to about 10 amino acid residues are inserted. The residues that are inserted can also be contiguous.

As used herein, the term "post-translational modification" refers to a modification of protein that occurs after it is translated from mRNA. Examples of post-translation modification include, but are not limited to, phosphorylation, dephosphorlyation, sulfation, desulfation, glycosylation, or deglycosylation chimeric modification.

As used herein, the term "chimeric modification" refers to joining fragments of two proteins to form a chimeric protein. A chimeric protein can also be referred to as a "fusion protein." An example of a chimeric protein includes, but is not limited to, a protein that comprises green fluorescent protein (GFP) and a fragment of another protein. In some embodiments, a fusion protein comprises a linker, a fluorescent protein, a fluorescent peptide, a protease cleavage sequence, a viral protein (e.g. Gag), and the like. In some embodiments, the fusion protein is a Gag-fusion protein.

As used herein the phrase "a portion of a lipoparticle's membrane" refers to the lipids and other proteins present in or on the surface of a lipoparticle. A portion of a lipoparticle's membrane is either the entire membrane of the lipoparticle or less than the entire membrane of the lipoparticle.

The "standard cell line" can be any cell line that expresses the protein of interest. Examples of standard cells lines are mammalian cells, mouse cells, human cells such as, but not limited to, HeLa cells, 293 cells, primary cells, stem cells, and the like. In some embodiments, the standard cell line expresses the protein of interest. In some embodiments, the standard cell line does not express the protein of interest or the protein of interest cannot be detected.

As used herein, the term "fluorophore" refers to a compound or composition that fluoresces. In some embodiments, a fluorophore is a dye or a protein.

As used herein, the term "labeling" refers to incorporating a fluorophore into a particle or bead. "Labeling" also refers to contacting a particle with a labeled bead.

As used herein, the term "viral particle" refers to complete virions (viruses), as well as related viral particles, and single or isolated viral proteins or particles containing a single viral protein. Examples of viral particles include, but are not limited to capsids, core particles, virions depleted of one or more envelope proteins, virion envelopes without the nuclear capsid core, virion envelope fragments and defective or incomplete virions. In some embodiments, viral particles are retroviral particles.

As used herein, the term "particle" includes lipoparticles, virus-like particles, and complete virions.

As used herein, the term "modulator" includes manufactured or naturally occurring compounds, molecules, peptides, polypeptides, nucleotide sequences, proteins, or combination thereof, any of which alter the physiological state, conformation, or function of a protein upon which the modulator acts. A "modulator of an ion channel" is any aforementioned compound that specifically alters the physiological state, conformation, or function of an ion channel polypeptide.

As used herein, the term "polypeptide" includes any manufactured or naturally occurring full-length protein, wild-type protein, modification of protein, or polypeptide fragment thereof.

In some embodiments a microfluidic device is narrower than about 1,000 microns, about 100 microns, about 10 microns, or about 1 micron.

EXAMPLES

The invention is now described with reference to the following examples. These examples are provided for the purpose of illustration only and the invention should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

Example 1

Detection of Ionophore-mediated Ion Movement Across the Membranes of Intact Retroviral-based Virus-like Particles Using a Membrane Potential-sensitive Dye We tested whether the selective movement of ions across the membrane of intact lipoparticles, mediated by the ionophore valinomycin, could be detected using a membrane potential-sensitive dye. Particles, produced as described ((Doranz, et al. (2004)) U.S. patent application Ser. No. 10/901,399, incorporated by reference herein), were incubated for 5 minutes in 1 uM valinomycin, a $K^+$-selective ionophore. Particles were then mixed with FMP-Blue dye (Molecular Devices) by re-suspension in 45 ul of 10 mM Hepes 7.0 containing 0.2 ul of dye. The mixture was placed in a 60 ul minicuvette inside of a Perkin Elmer LS-50B monochromator-based fluorometer, and fluorescence measured every 5 seconds using an excitation wavelength of 530 nm and an emission wavelength of 565 nm. After establishing a stable baseline, $K_2SO_4$ was injected to a final K+ concentration of 60 mM, and the solution was mixed. A rapid increase in fluorescence upon $K^+$ injection (FIG. 1), consistent with valinomycin-mediated movement of $K^+$ ions across the lipoparticle membrane from the exterior to the interior was observed. The membrane potential response to $K^+$ injection was entirely dependent upon the presence of valinomycin, which could be added either before or after the addition of $K^+$ (FIG. 1B), supporting the hypothesis that lipoparticle membranes are normally impermeable to small molecules. The fluorescent signal was proportional to the amount of particles used (FIG. 1A) and the amount of $K_2SO_4$ injected (FIG. 1C). The small (10%) decrease in fluorescence observed after $K_2SO_4$ injection in negative control samples was proportional to the change in sample volume. The subsequent decay of the fluorescent signal to baseline represents a combination of possible events, including $K^+$ and $H^+$ leakage and changes in lipoparticle size (Cooper, et al. (1990), Biochem Biophys Res Commun, 173:1008-12, Venema, et al. (1993), Biochim Biophys Acta, 1146:87-96). No signal was observed when other samples (NaCl, Hepes buffer alone) were injected, or when the lipoparticle membranes were first disrupted with deoxycholate detergent (DOC) (FIG. 5D) or with the non-specific pore-forming peptides gramicidin and melittin (FIG. 2). Collectively, the data indicate that lipoparticles are capable of maintaining an ion gradient, and that a change in this membrane potential can be detected using a fluorescent dye.

Example 2

Detection of Ion Movement Across the Membrane of Influenza a Viral Particles

We demonstrated that ion movement could be detected across the membrane of intact, native influenza virions, in a manner similar to that already shown for lipoparticles. Influenza A (Udorn/72) virus was grown in Madin-Darby Canine Kidney (MDCK) cells using standard techniques. Harvested virus was purified twice through a 20% sucrose cushion. Viral particle quantity was determined by dynamic light scattering (DLS) intensity (FIG. 3A), and titers measured using plaque assay. DLS intensity measurements were used herein as described in ((Doranz, et al. (2004)) U.S. patent application Ser. No. 10/901,399), where all DLS measurements are a relative value of a 1:50 dilution of particles, as measured in counts/sec units. An aliquot of virions was examined by fluorescent microscopy (FIG. 3, inset). $15 \times 10^6$ DLS units of purified virus was treated with 1 uM valinomycin for 5 minutes at room temperature, and added to 45 ul of 10 mM Hepes pH 7.0, containing 0.2 ul FMP dye (Molecular Devices) in a 60 ul minicuvette. Fluorescence in the minicuvette was measured every second using an excitation wavelength of 530 nm and an emission wavelength of 565 nm in a Perkin Elmer LS-50B monochrometer-based fluorometer. K2SO4 was then added to a final K+ concentration of 60 mM. An increase in fluorescence consistent with K+ movement into the virus interiors was detected in influenza viruses treated with valinomycin, but not in those pre-treated with buffer alone (FIG. 3B). Collectively these data suggest that the movement of ions across viral membranes can be detected using membrane potential-sensitive dyes in diverse viruses.

Example 3

Ion Movement can be Detected Across the Membranes of Lipoparticles Produced Using Diverse Core Structures Here we demonstrated that the ability to measure ion flow across viral membranes is not dependent on the structure of the viral core protein. Lipoparticles were produced from HEK-293 cells, as described in U.S. patent application Ser. No. 10/901,399, incorporated herein by reference in its entirety, using plasmids containing either the wild-type MLV Gag-Pol gene, the MLV Gag-Pol D32S mutant (which inactivates protease activity), or a gene constructed by fusing MLV Gag to GFP. Each type of lipoparticle (1×10(6) DLS units each) was treated for 5 minutes with valinomycin, added to a solution containing FMP dye, and fluorescence measured as described. After addition of K2SO4 to a final K$^+$ concentration of 60 mM, an increase in fluorescence, consistent with valinomycin-mediated ion transport, was detected in lipoparticles produced from all three core proteins (FIG. 4). These data indicate that disruption of the Pol gene, or fusion of the structural (Gag) protein to another protein, does not hinder the movement of ions across the viral membrane, nor its detection using a membrane protein-sensitive dye. One skilled in the art would recognize that ion movement across the membranes of other viral structures—including, but not necessarily limited to, naturally occurring or molecularly engineered viral core proteins, MLV Gag-fusion proteins, HIV Gag, or influenza M1—could be similarly monitored.

Example 4

The Concentration of Ions in Lipoparticle Interiors can be Altered Using Electroporation MLV lipoparticles were suspended in Hepes buffer 7.0 containing either 5 mM K$^+$ (low-K buffer) or 60 mM K$^+$(high-K buffer). Lipoparticles (2 ul) were then electroporated (100 ohms, 0.04 KV, 0.25 uFD). Electroporation induces small, transient pores to form in membranes. After electroporation, KCl was added to lipoparticles suspended in low-K buffer to a final concentration of 60 mM, and all lipoparticles were diluted 10-fold into 10 mM Hepes containing FMP dye. While measuring fluorescence (530 nm excitation, 565 nm emission), valinomycin (5 uL of 10 uL stock added to 45 uL solution) was added to a final concentration of 1 uM. Lipoparticles electroporated in low-K buffer emitted a fluorescent signal indicative of K+ movement down a concentration gradient, while those electroporated in high-K buffer did not (FIG. 5). This data demonstrates that electroporation porated the lipoparticle membrane, altering the internal ion concentration of the lipoparticle to match that of the electroporation buffer. One skilled in the art would recognize that other methods of temporarily, or permanently, porating or permeabilizing the viral membrane, such as pore-forming peptides, or allowing slow diffusion over time, would similarly allow for ionic or small molecule equilibration of the viral interior with the suspension buffer. Other ions, molecules, substances, or quantum dots could also be incorporated into viral particles using this method.

Example 5

Diverse Membrane Potential-sensitive Dyes can be Used to Monitor Ion Movement Across Viral Membranes A diverse range of membrane potential dyes at various concentrations can be used to detect ion movement across viral membranes. For example, the membrane potential dyes di-4-ANEPPS and DiBAC4(3) were used to monitor K$^+$ translocation in a manner similar to that already described herein for FMP. Briefly, MLV lipoparticles were suspended in 1 μM valinomycin for 5 minutes at room temperature and then added to 10 mM Hepes 7.0 with 100 μM di-4-ANEPPS or 0.5 μM DiBAC4(3) in cuvettes. While monitoring fluorescence, K$_2$SO$_4$ was added to a final K$^+$ concentration of 60 mM. An increase in fluorescent emission was observed in lipoparticles loaded with either dye (FIG. 6). No fluorescent signal was recorded when viral structure was first disrupted using DOC (FIG. 6A), or when lipoparticles were not treated with valinomycin (FIG. 6B). Similarly, K$^+$ movement across VLP membranes was detectable (data not shown) in 384-well microplates, using a FlexStationII, as described herein, when valinomycin-treated VLPs containing no particular ion channel (null VLPs) were loaded with a number of other membrane potential dyes at a range of concentrations, summarized in Tables 1 and 2 Null VLPs not treated with valinomycin failed, as expected, to emit a fluorescent signal upon challenge with K$_2$SO$_4$, indicating that K$^+$ movement is not normally possible across VLP membranes. Collectively, these data indicate that diverse membrane potential-sensitive dyes, at a range of concentrations, can be used to detect ion movement across viral membranes. One skilled in the art would recognize that other dyes or reporters, whether chemical or protein (such as GFP), with emission spectra or signaling properties sensitive to ion concentration, ion movement, or charge distribution, could similarly be used to monitor ion movement across viral membranes.

TABLE 2

| All membrane potential dyes were obtained from Molecular Devices, Molecular Probes, or Anaspec. ||
| --- | --- |
| Membrane Potential Dye | Concentration Range Tested |
| FMP Blue | 0.005-50% |
| FMP Red | |
| DiBAC(4)3 | 0.2-60 μM |
| DisBac2(3) | 0.003-10 μM |
| HLB 021-152 | |
| HLB 021-155 | |
| HLB 007-054 | |
| HLB 021-149 | |
| HLB 007-052 | |
| HLB 004-111 | |
| HLB 028-008 | |
| HLB 004-078 | |
| HLB 004-183 | |

Example 6

Detection of Protonophore-mediated Ion Movement Across Lipoparticle Membranes

We demonstrated that, using a membrane potential-sensitive dye, one could monitor the movement of H$^+$ across MLV lipoparticle membranes, mediated by the protonophore FCCP, in a manner similar to that already demonstrated for valinomycin-mediated K$^+$ movement across lipoparticle membranes. Briefly, MLV lipoparticles (15e6 DLS units), prepared as outlined herein, were treated with 20 uM FCCP, and then added to 45 ul of 10 mM Hepes 7.0 containing 0.2 ul FMP dye in a minicuvette. Fluorescence (530 nm excitation wavelength, 565 nm emission wavelength) was monitored at 5 second intervals in a Perkin Elmer LS-50B monochrometer-based fluorometer, and after a stable baseline was established, HCL was added (approximately 1 ul of 0.1-0.3 N, to a final pH of ~6.0). An increase in fluorescence intensity was observed consistent with the movement of H$^+$ across lipoparticle membranes (FIG. 7A). The fluorescent signal was not inhibited by pre-treatment with amantadine or rimantadine (inhibitors of M2-mediated $H^+$ transport in influenza A), but was greatly attenuated in lipoparticles that were not pre-treated with FCCP. Addition of 5 uM mellitin, a non-specific pore-forming peptide attenuated the fluorescent signal. A similar experiment was conducted using purified influenza A (Udorn) virions treated with FCCP and yielding similar results (FIG. 7B). These data indicate that the movement of diverse ions across lipoparticle membranes can be monitored using membrane potential-sensitive dyes. One skilled in the art would recognize that the activity of diverse ionophores, and other passive or active ion transporting elements, and that the movement of diverse ions across viral membranes, can be monitored by similar means.

Example 7

Detection of Changes in Lipoparticle pH Using a pH-Sensitive GFP Protein Incorporated into Virions Here it was shown that the movement of $H^+$ across viral membranes can be detected using lipoparticles constructed using a pH-sensitive fluorescent protein. The intensity of the fluorescent emission of Green Fluorescent Protein (GFP) is pH dependent, and variants of GFP with improved pH-sensitivity have been developed. cDNA coding for a fusion protein comprising eGFP (C-terminal) and the MLV structural protein (Gag) was constructed (Gag-GFP) and cloned into a CMV-driven expression vector by conventional means. This plasmid was transiently transfected into HEK-293 cells, and retroviral lipoparticles harvested, purified, and quantified, as described previously. Lipoparticles were then suspended in buffers of defined pH (6.0-7.5) and the viral interiors allowed to equilibrate with the suspension buffer. Fluorescence of each suspension, and of each solvent alone, was then measured using a Wallac Victor2V (FIG. 8A). Fluorescence was linearly correlated with pH of the equilibrium buffer, and was dependent upon the presence of lipoparticles.

Changes in pH were also measured in real-time. Gag-GFP lipoparticles were equilibrated at pH 6.5 (lipoparticle$_{6.5}$) and at pH 7.5 (lipoparticle$_{7.5}$) and fluorescence monitored in real time. Buffer was then added to each suspension of lipoparticles such that the final external pH of the lipoparticle$_{6.5}$ suspension was 7.5, while that of the lipoparticle$_{7.5}$ suspension was 6.5. An increase in fluorescence in the lipoparticle$_{6.5}$ suspension indicated the movement of H+ out of the lipoparticle interiors, while a decrease in fluorescence in the lipoparticle$_{7.5}$ suspension indicated a movement of H+ into the lipoparticle interiors (FIG. 8B). A similar experiment was conducted, changing the pH of the solution multiple times during the course of the experiment (FIG. 8C).

Collectively these data suggest that pH, changes in pH, and H+ movement can be monitored in lipoparticles using a pH-sensitive indicator. Similarly, pH-sensitive proteins or other molecules could be incorporated into lipoparticles by other means, including binding to or on the lipoparticle membrane or other constituents of the lipoparticle.

Example 8

Detection of Viral Ion Channel-mediated Ion Transport within Native Virions

We demonstrated that $H^+$ movement across the membranes of purified, intact native influenza A virions by the M2 viral ion channel can be detected. Influenza A (Udorn/72) virus was grown in Madin-Darby Canine Kidney (MDCK) cells using standard techniques. Harvested virus was purified through a 20% sucrose cushion. Viral particle quantity was determined by dynamic light scattering intensity, and titers measured using plaque assay. $15 \times 10^6$ DLS units of purified virus was re-suspended in 45 ul of 10 mM Hepes pH 7.0, and mixed with 0.2 ul FMP dye (Molecular Devices) in a 60 ul minicuvette. Fluorescence was measured every second using an excitation wavelength of 530 nm and an emission wavelength of 565 nm in a Perkin Elmer LS-50B monochrometer-based fluorometer. After a stable baseline was established, HCl was added (approximately 1 ul of 0.3 N HCl) to reduce pH to below 6.0 (at which M2 is activated). A fluorescent signal was observed upon reduction of pH, consistent with M2-mediated movement of $H^+$ across viral membranes (FIG. 9). Pre-treatment of influenza A virions with amantadine (1-100 uM), a known inhibitor of M2 activity, attenuated the fluorescent signal in a dose-dependent fashion (FIG. 9). Collectively, these data demonstrate that M2 activity can be detected within native virions.

Example 9

Incorporation of Eukaryotic Ion Channels into Intact Lipoparticles

Here, we demonstrated that MLV lipoparticles could be prepared to contain a eukaryotic ion channel. Drosophila Shaker (GenBank Accession Number M17211, GI: 157063) is a voltage-regulated (opens upon depolarization) K-channel that serves as a prototype ion channel due to its extensive characterization. Lipoparticles containing Shaker were produced as described herein by co-transfecting 293 cells with plasmids encoding MLV Gag and a variant of Shaker (Shaker (Δ6-46)T449V containing a FLAG epitope near its N-terminus) under the control of CMV promoters. Following harvest and purification as described previously, 4 ug of lipoparticles were analyzed by western blot using an anti-FLAG antibody. Analyses were conducted before and after deglycosylation using PNGase F (New England Biolabs). Lipoparticle-incorporated Shaker indicated appropriate apparent molecular weight before and after removal of the two N-linked carbohydrates (N259 and N263) in its first extracellular loop (FIG. 10). Identity with cell-expressed Shaker was determined by comparison to cell lysates (50,000 cells per lane) before and after deglycosylation (FIG. 10). These data demonstrate the successful incorporation of Shaker ion channel into lipoparticles, and its apparent identity with cell-expressed Shaker in cells. In a similar manner, lipoparticles containing the ion channels Kv1.3 and CFTR were also prepared, purified, and incorporation confirmed by western blot, as previously described (Doranz, et al. (2004)). Ion channels incorporated onto lipoparticles are derived from the cell surface, so one would expect that ion channels on lipoparticles have a high probability of retaining their native conformation and activity. One skilled in the art would recognize that alternative eukaryotic and non-eukaryotic ion channels could be incorporated by similar means, and that other producer cells could similarly be substituted for those described here.

Example 10

Detection of the Activity of a Eukaryotic Ion Channel in Lipoparticles

The ability to detect the ion-conducting activity of a eukaryotic ion channel (Shaker) in lipoparticles was demonstrated. Like many ion channels, Shaker is a complex membrane protein, containing six transmembrane domains and forming tetramers in the membrane (Deutsch (2002), Annu Rev Physiol, 64:19-46).

Whether Shaker, when incorporated into lipoparticles as described herein, could effect depolarization of the lipoparticle membrane was tested. Shaker lipoparticles (Shaker(Δ6-46)T449V) were suspended in 10 mM Hepes 7.0 containing 0.4% FMP-Blue dye (Molecular Devices). The mixture was placed in a minicuvette inside of a Perkin Elmer LS-50B fluorometer, and fluorescence was measured before and after addition of $K_2SO_4$ to a final K+ concentration of 1-60 mM. A rapid increase in fluorescence upon $K_2SO_4$ injection, consistent with Shaker-mediated movement of $K^+$ across the lipoparticle membrane was observed (FIG. 11A). The response was proportional to the concentration of $K^+$ injected, and no signal was observed when controls were injected (NaCl or buffer alone, not shown), when Shaker-lipoparticle structural integrity was first disrupted using 0.05% deoxycholate, or when lipoparticles incorporating a non-ion channel control protein (CXCR4) were substituted for Shaker lipoparticles. Similar experiments conducted with ion channel-expressing cells yielded nearly identical results (FIG. 11D). Shaker $K^+$ lipoparticles continued to support membrane potential response upon $K^+$ challenge even after 14 months in storage at 4° C.

As a further test of specificity, Shaker lipoparticles and valinomycin-treated null-lipoparticles (devoid of specific ion channels) were incubated with 10 nM charybdotoxin (CHTX), a selective inhibitor of Shaker function, or buffer alone. Lipoparticles were then loaded with FMP dye, $K^+$ added, and fluorescence monitored, as described. CHTX completely inhibited Shaker conductance of $K^+$ across lipoparticle membranes, but did not influence K+ movement mediated by valinomycin in control lipoparticles (FIG. 11B). Toxins, including iberiotoxin (10 uM) and margatoxin (10 uM), that are unable to bind Shaker but do inhibit other $K^+$ channels, did not inhibit Shaker activity (FIG. 11C). Together, these data indicate the specificity of Shaker-mediated $K^+$ transport across the lipoparticle membrane. Collectively, these data suggest that lipoparticle-incorporated Shaker exhibits functional similarity to that expressed in cells, and confirms the ability to detect Shaker activity in lipoparticles using a membrane potential-sensitive dye.

Example 11

Detection of Diverse Ion Channels in Lipoparticles

To show that the activity of diverse ion channels in lipoparticles could be monitored in a manner similar to that demonstrated for Shaker, lipoparticles were produced containing the human KCNQ2/3 channel (a hetero-oligomeric human K+ channel), the T449K mutation of Shaker (26 msec inactivation time constant), and the 5HT3a cation channel (pentameric serotonin-gated ion channel). Purified lipoparticles containing each ion channel were pre-treated with ion-channel-specific inhibitors (120 mM $BaCl_2$, 10 nM CHTX, 10 uM tubocurarine), or with buffer alone. Control null-lipoparticles (containing no specific ion channel) were pre-treated with valinomycin (1 uM for 5 minutes at room temperature), with or without the 5HT3a inhibitor tubocurarine. Lipoparticles were then (separately) added to 10 mM Hepes pH 7.0, containing 0.2 ul FMP, and, in the case of 5HT3a lipoparticles, 2.4 mM serotonin. Fluorescence was then measured while $K_2SO_4$ was added to a final $K^+$ concentration of 60 mM, as outlined herein. Each lipoparticle preparation containing an ion channel, and the valinomycin-treated control null-lipoparticles, each emitted a fluorescent signal upon addition of the appropriate cation ($K^+$ for Shaker and KCNQ2/3, and $Na^+$ for 5HT3a) indicating cation movement across the lipoparticle membrane (FIG. 12). In the case of 5HT3a lipoparticles, the signal was dependent upon the presence of the ion channel ligand, serotonin. Ion channel-specific inhibitors were, in each case, capable of inhibiting the fluorescent signal, indicating inhibition of the functional ion channel. Tubocurarine was not, however, able to abrogate the fluorescent signal accompanying $K^+$ movement mediated by valinomycin, demonstrating specificity of its inhibition. These data indicate that fully-functional ion channels with diverse structural, activation, and gating characteristics can be incorporated into lipoparticles, and that their ion-conducting activities can be monitored.

Example 12

Detection of Viral Ion Channel Activity within Lipoparticles

A viral ion channel (influenza A M2) can be incorporated within retroviral lipoparticles, and its activity monitored. Lipoparticles containing the Udorn/72 Influenza A M2 ion channel were produced from HEK-293 cells using methods described herein. $15 \times 10^6$ DLS units of purified M2 lipoparticles were suspended in 45 ul of 10 mM Hepes pH 7.0 containing 0.4% FMP dye, and fluorescence monitored in a 60 ul minicuvette. The addition of approximately 1 ul of 0.3 N HCl (which reduced pH to below 6.0) resulted in a fluorescent signal indicative of H+ transport across the lipoparticle membrane (FIG. 13). Null-lipoparticles (containing no specific ion channel) pre-treated with 20 uM FCCP emitted a similar fluorescent signal upon addition of HCl, but null lipoparticles not treated with FCCP exhibited a greatly reduced fluorescence upon addition of HCl. The inclusion of amantadine (100 uM) or rimantadine (10 uM) inhibited the fluorescent response in M2-lipoparticles (FIG. 13), but was not capable of inhibiting FCCP-mediated H+ transport (FIG. 7). Collectively, these data suggest that functional viral ion channels can be incorporated into lipoparticles, and their activity monitored.

Example 13

Detection of Viral Ion Channel Function within Lipoparticles Using a pH-Sensitive GFP Protein The activity of the influenza A M2 protein can be detected in influenza-based lipoparticles using a pH-sensitive fusion protein based on the influenza A structural (M1) core protein. cDNA coding for a fusion protein comprising the pH-sensitive GFP variant, pHFluorin (Hanson, et al. (2002), Biochemistry, 41:15477-88), and the M1 structural protein will be constructed and cloned into a CMV-driven expression vector. M1-GFP fusion proteins have been previously described (Sato, et al. (2003), Virology, 310:29-40). Because M1 is sufficient for virion formation (Gomez-Puertas, et al. (2000), J Virol, 74:11538-47, Latham, et al. (2001), J Virol, 75:6154-65), lipoparticles released from the cells will contain high concentrations of pHFluorin. A second plasmid containing the influenza A/Udorn/72 M2 gene will also be constructed. HEK-293 cells will be co-transfected with both plasmids, and lipoparticles harvested, purified, and quantified as outlined herein. M1-pHFluorin influenza lipoparticles can similarly be produced by transfecting cells with the M1-pHFluorin plasmid alone, and then infecting these cells with wild-type Udorn virus (the resulting harvested virions will co-package the M1-pHFluorin with wild-type M1 (Sato, et al. (2003), Virology, 310:29-40)).

Lipoparticles ($15 \times 10^6$ DLS units) produced to contain pHFluorin will be treated with valinomycin (1 uM, 5 minutes, room temperature), to ensure that subsequent pH changes are measured under electroneutral conditions (this will reduce electrostatic retardation of H+ movement across lipoparticle membranes). Treated lipoparticles will then be added to 10 mM Hepes (pH 7.0), 2 mM KCl, 2 mM NaCl. The translocation of $H^+$ across viral membranes by M2 will be monitored in real-time by detecting fluorescence (ex530/em565), using a Molecular Devices FlexStationII, during addition of MES buffer pH 4.5 (final concentration 30 mM). pHFluorin can be measured ratiometrically to increase signal-to-noise and eliminate artifacts such as the absolute concentration of fluorophore (Miesenbock, et al. (1998), Nature, 394:192-5). The lowering of the pH in the buffer will result in H+ translocation into the particles (through M2) and lowering of the pH inside the particle. The lowered pH inside the particle will change the fluorescence of pHFluorin. The specificity of the signal will be confirmed by pre-incubating control lipoparticles with amantadine (100 uM), by substituting MES with buffers of neutral pH, by substituting M2-lipoparticles with control null-lipoparticles that do not contain the M2 protein, and by pre-treating lipoparticles with the protonophore FCCP. One skilled in the art would recognize that alternative pH-sensitive fluorophores could be used, including other fluorescent proteins and dyes (e.g. CypHer (Amersham Biosciences), SNARF, SNAFL, Oregon Green (Molecular Probes)).

Example 14

Optimization of Ion Channel Density in Lipoparticles for Detection of Partial Membrane Depolarization One ion channel polypeptide may be sufficient to achieve maximum depolarization of the lipoparticle membrane. Additional ion channels in the lipoparticles would not further increase membrane depolarization but could bind inhibitors, thus potentially reducing the ability to detect inhibition of membrane depolarization. To test this, the minimum number of ion channels required for full membrane depolarization was ascertained. We demonstrated that using this ion channel density one could detect the action of an ion channel inhibitor at a range of potencies. Lipoparticles were prepared incorporating different quantities of Shaker ion channel per particle, by transfecting producer HEK-293 cells with 3-105 ug of Shaker($\Delta$6-46)T449V plasmid. 10 ug of Shaker plasmid used for production represents a 1:3 ratio of Shaker:pCGP plasmid. The stochastic nature of membrane protein incorporation into budding lipoparticles defines a predictable relationship between the amount of plasmid used to transfect producer cells, and the average number of membrane protein molecules incorporated into each lipoparticle. Each batch of lipoparticles was suspended in 10 mM Hepes (7.0) containing 0.4% FMP blue dye and fluorescence monitored as $K_2SO_4$ was added to a final $K^+$ concentration of 60 mM, as described previously. A fluorescent signal in all lipoparticles containing some Shaker ion channel was observed, and the fluorescent signal appeared to be at or near maximum in lipoparticles produced using 10 ug Shaker plasmid or more (FIG. 14A). Lipoparticles produced from cells transfected with less than 10 ug of plasmid exhibited a substantially less intense fluorescent signal upon addition of K+. These data suggest that the amount of plasmid required to produce lipoparticles with the minimum number of Shaker molecules for full membrane depolarization under these experimental conditions is approximately 10 ug.

Lipoparticles produced using 10 ug of Shaker plasmid were treated with CHTX at concentrations ranging from 100 pM to 10 nM. These lipoparticles were then loaded with 0.4% FMP blue dye, and fluorescence monitored during addition of K2SO4, as described. A CHTX concentration-dependent inhibition of the fluorescent signal was observed (FIG. 14B). These results are in close agreement with those reported in the literature for CHTX inhibition of Shaker in cells (~3.6 nM, (Goldstein, et al. (1994), Neuron, 12:1377-88, MacKinnon, et al. (1988), Neuron, 1:997-1001, Miller (1995), Neuron, 15:5-10)). These data indicate that the average number of ion channels incorporated into lipoparticles can be optimized to enable partial membrane depolarization, or partial inhibition of membrane depolarization to be detected. One skilled in the art would recognize that the quantities reported in this example are dependent upon the type of ion channel, the inhibitor being used, reaction conditions such as the amount of K+ added or the pH, and inherent characteristics of the lipoparticles, such as diameter. Other quantities of reagents could be substituted to allow for variation in any of these factors.

Example 15

Optimizing the Detection of Ion Movement Across Viral Membranes by Selecting a Membrane Potential-sensitive Dye with Appropriate Properties Different membrane potential-sensitive dyes have specific properties that make them more or less suitable for monitoring ion movement across lipoparticle membranes under different circumstances. In turn, viral particles possess properties that may improve the versatility of membrane potential probes compared with what is achievable in cells. The particles described herein can be loaded with much higher concentrations of dye (for increased sensitivity) than can be achieved with cells, in which overloading can produce artifacts from organelle interference and diminished cell health (Nicholls, et al. (2000), Trends Neurosci, 23:166-74, Plasek, et al. (1996), J of Photochemistry and Photobiology, 33:101-124, Zochowski, et al. (2000), Biol Bull, 198:1-21). Furthermore, dyes which are toxic to cells may be used with these particles allowing new and better dyes to be exploited.

Three key properties to assess the performance of dyes are: 1) sensitivity, 2) the ability to measure dye response using ratios of fluorescent wavelengths, and 3) the dye's speed of response (fast vs. slow) are used. Using these three criteria, four dyes—DiSBAC(1)3, DiSC3(5), Rhodamine 421, and di-4-ANEPPS are tested. The first two dyes are classified as slow dyes, while the latter two are classified as fast dyes. Both DiSC3(5) and di-4-ANEPPS can be measured ratiometrically. Additional commercially available dyes may also be tested (Haugland (2003)). Optimal concentrations of each dye to report Shaker activity within MLV lipoparticles will be determined. Briefly, Shaker lipoparticles will be suspended in buffer (10 mM Hepes 7.0, 2 mM NaCl, 2 mM KCl) containing various concentrations of each dye. The ion channels are activated by addition of 30 mM $K_2SO_4$, and fluorescence monitored in real-time using a Molecular Devices FlexStationII. Response curves will be generated, and the maximum fluorescence signal determined for each of the four dyes. Each dye is also evaluated in the presence of additives (DMSO, glycerol), inhibitors (charybdotoxin), and controls (valinomycin) to ensure compatibility and specificity. The results from each dye are compared to select dyes that can yield the best response.

Example 16

Conditions for Detecting Ion Movement Across Lipoparticle Membranes Using Membrane Potential-sensitive Dyes Conditions that effect the movement of ions across viral membranes can be monitored, such as the number of lipoparticles used, the amount of FMP dye with which they are loaded, the amount of valinomycin, and the assay temperature. These variables can be changed to produce fluorescent signals of different intensity. Various amounts of lipoparticles (0-7.5 ul) containing Shaker, or null-lipoparticles (containing no specific ion channel) were treated with a range of concentrations of valinomycin (0.5-10 uM, 5 minutes, room temperature) or buffer alone. After adding the particles to microplate wells containing 45 ul Hepes (pH 7.0) with a range of volumes of FMP dye (0.25-5 ul), fluorescence was monitored during the injections of 30 mM $K_2SO_4$ using a Wallac Victor2V. The effect of FMP dye concentration (FIG. 15A), lipoparticle amount (FIG. 15B), and valinomycin concentration (FIG. 15C) are shown, and demonstrate that the signal can be optimized for microplate formats by varying these factors.

Incubation of lipoparticles treated with FMP dye overnight or just prior to the addition of K+, resulted in a similar fluorescent signal (FIG. 16) when valinomycin (1 uM final) was added (5 min before assay), as measured on a Perkin Elmer LS-50B, indicating stability of the dye-lipoparticle interaction. In addition, storage of Null-lipoparticles (treated with valinomycin just before assay) or Shaker lipoparticles at −80° C., 4° C., 37° C. for 1 hour had only minor effects on signal, demonstrating the stability of the Lipoparticles for ion channel measurement at different temperatures. Shaker lipoparticles have been stored at 4° C. for over a year and they have still retained their ability to signal in response to K+.

Example 17

Lipoparticles can be Dried and Reconstituted for Ion Channel Studies

Lipoparticles were dried in the presence of 5% sucrose. Once dried, the particles were stored at room temperature. After 72 h the particles were reconstituted in 10 mM Hepes 7.0 and tested for K+ channel activity by adding 1 uM valinomycin, FMP dye, and challenging with K+. The Lipoparticles retained their ability to support a K+-mediated membrane potential response (FIG. 17). For comparison, particles that had not been dried, either with or without sucrose, were also tested. Particles that were also treated with 0.01% deoxycholate did not retain the ability to support a membrane potential. One skilled in the art would recognize that the ability to dry and reconstitute ion channel activity in lipoparticles can be applied to other formats, such as wells and microarrays, to create unique and useful tools.

Example 18

Detection of Lipoparticle Ion Channel Activity with a Microarray

Microarrays of GPCRs using lipoparticles (Doranz (2003)) (US Patent Application Publication No. 2005/0123563) and commercial membrane vesicles (Fang, et al. (2002), J Am Chem Soc, 124:2394-2395) have previously been described. In these cases, membrane structures were dried on the substrate in a form that preserves the structure of the membrane protein. Here, lipoparticles containing ion channels to be tested will be printed in triplicate on the surface of a gamma-aminopropylsilane (GAPS)-coated slide using a commercial microarray printing system. To preserve protein structure during sample spotting, lipoparticles will be printed in a solution containing 5% sucrose. The arrays will be stored at negative 80° C. until ready for use, at which time they will be brought to room temperature, placed in a 1×4 inch chambered dish (Quadriperm, VivaScience), and incubated with a model toxin (charybdotoxin, CHTX). During ion channel stimulation with $K_2SO_4$, array fluorescence will be recorded in real time using a CCD camera. Spots of lipoparticles containing CHTX-sensitive ion channels (e.g. Shaker) are not expected to produce a change in fluorescent signal, while spots containing K+ channels or transporters insensitive to CHTX (e.g. KCNQ2/3, valinomycin-treated lipoparticles) are expected to generate a change in fluorescent signal.

Although microarrays are traditionally printed on glass slides, arrays within 96-well microplates are more compatible with traditional screening equipment. These so-called "arrays within arrays" could permit compound specificity to be more easily determined. For example, an array of 16 different voltage-gated K+ channels spotted into each well of a 96-well microplate could be used to screen the specificity of 96-different compounds against all 16 ion channels using only a single microplate. The protein microarray format has important potential applications in investigating drug cross-reactivity.

Example 19

Detection of Lipoparticle Ion Channel Activity within a Microfluidic Device

The ability to present structurally intact, functional ion channels within a 150 nm particle allows more advanced technologies to be used for drug discovery against them. Microfluidic devices capable of automated screening at the nanometer scale are beginning to emerge (Sundberg (2000), Curr Opin Biotechnol, 11:47-53) but are rarely used for ion channels because of their dependence on cells. The goal of microfluidics is not simply to continually reduce the size and volume of a device, but to integrate different liquids, reagents, and functions into more automated detection systems. This requires not only miniaturized detection systems, but also miniaturized reagents such as the particles of the invention. Lipoparticles are used within several microfluidic devices to test their compatibility for the detection of functional response. Multiplexed microfluidic devices with the capability of detecting hundreds to thousands of samples are preferred.

The performance of hERG-lipoparticles in the microfluidic flow cell of a continuous-flow, automated system, the Caliper LabChip 3000 is tested. hERG lipoparticles suspended in 10 mM Hepes 7.0 buffer containing 1% FMP dye will be loaded into a Caliper LabChip. The LabChip will automatically mix into the stream of lipoparticles one of several compounds prepared for testing, including E-4031, astemizole, verapamil, and loratidine (all are known hERG inhibitors). Once lipoparticles are incubated with a potential inhibitor, $K_2SO_4$ is injected into the stream of lipoparticles and the fluorescent response is detected using laser excitation. The Caliper 3000 is capable of performing all of these functions automatically and within picoliter volumes, permitting automated drug screening of desired targets. Agonists and antagonists are titered to determine a dose response curve for each molecule. These data demonstrate that lipoparticles comprising ion channel polypeptides can be adapted for use with microfluidic devices.

Example 20

Detection within Microplates

Experimental conditions for monitoring ion channel activity in lipoparticles in microplates using a fluorescence microplate reader were established. Lipoparticles pre-treated with valinomycin (1 uM, 5 minutes, room temperature) were suspended in Hepes (pH 7.0) containing FMP dye (amounts of lipoparticles and FMP were optimized as described herein, FIGS. 18 A and B). Aliquots (50 ul) were dispensed across a 96-well microplate. A Wallac Victor 2V microplate reader was programmed to automatically inject 5 ul of 500 mM $K_2SO_4$ (45 mM $K_2SO_4$ final), simultaneously to each well, and to measure fluorescence at 2 sec intervals starting 10 sec before the addition of $K^+$.

To establish experimental reproducibility under these conditions, twelve replicates each of valinomycin-treated and non-treated null-lipoparticles (no ion channel) were mixed with FMP dye, exposed to $K^+$, and fluorescent signals recorded in the Wallac Victor2V. Valinomycin-treated lipoparticles produced a signal of 1.347+/−0.036, while untreated lipoparticles produced a signal of 1.023+/−0.009 (mean+/− standard deviation) (FIG. 18). These results yielded a statistical Z'-factor of 0.577, considered an excellent score for high-throughput screening purposes (Zhang, et al. (1999), J Biomol Screen, 4:67-73). The Z'-factor is an often-used, unitless statistical measure of the signal-to-noise and reproducibility of an assay (Zhang et al., 1999). A Z'-factor greater than 0.5 is highly desired in high-throughput screening assays. Collectively, our results demonstrate the utility of lipoparticles for high throughput-screening of potential ion channel modulators in miniaturized format, and suggest they are likely to be useful for high-throughput drug screening of potential ion channel modulators. Similar experiments were performed using valinomycin-treated lipoparticles in 384-well plates in a Molecular Devices FlexStationII and a Molecular Devices FLIPR-tetra (FIG. 19). These data establish the usefulness of lipoparticles on a high-throughput device for drug screening, especially drug screening for novel modulators of ion channels.

Example 21

Discovery of Novel Viral Ion Channels

Here, the existence of previously undiscovered ion channel activity within herpes simplex virus A is tested. Purified viral particles are suspended in assay buffer (10 mM Hepes pH 7.0 with 0.5% Molecular Devices' FMP dye). Viral suspensions are placed in a 96-well microplate, and fluorescence measured in real time using a Molecular Devices FlexStationII. After a stable baseline is established, solutions of ions are added (30 mM final concentrations of NaCl, KCl, $K_2SO_4$, CaCl2, or 0.01 N final concentration of HCl, each in different wells) and changes in fluorescence monitored. Viral particles pre-treated for 30 minutes at room temperature with ionophores (valinomycin, SQiRP, FCCP, ionomycin) are used as positive controls. Viral particles pre-treated with a detergent are used as negative controls. The entire experiment is repeated using purified virus suspended in assay buffer at pH 5.8 in order to detect any viral ion channel activity that may be dependent on acidification for activation. A change in fluorescence when the system is challenged with a particular ion would be indicative of the presence of an ion channel within the virus capable of conducting that ion. Thus, this methodology is capable of identifying previously undetected ion channel activities within viruses. The precise identity of the ion channel protein within the virus could then be determined using mass spectrometry, 2-D electrophoresis, protein arrays, or other proteomics techniques (e.g. with purified virions) to identify the ion channel sequence.

The existence of previously undiscovered ion channel activities within any enveloped virus can be screened using similar methodology. Examples of other enveloped viruses include, but are not limited to, influenza A, influenza B, influenza C, HIV-1, HIV-2, SIV, MLV, EIAV, ALV, chlorella, semliki forest virus, dengue virus, west nile virus, herpes simplex virus A, herpes simplex virus B (Knipe, et al. (2001)). In some embodiments, viruses from other virus families can be tested. Examples of other virus families include, but are not limited to, alphavirus, arenavirus, arterivirus, bornavirus, bunyavirus, coronavirus, filovirus, flavivirus, hepadnavirus, herpesvirus, orthomyxovirus, paramyxovirus, poxvirus, retrovirus, rhabdovirus, togavirus, adenovirus, astrovirus, calcivirus, papillomavirus, parvovirus, picornaviridae, polyomavirus, reovirus (Knipe, et al. (2001)).

Example 22

Discovery of M2 Inhibitors

The screening of compounds for their ability to inhibit influenza A M2 activity in lipoparticles is demonstrated. The benefits of using lipoparticles for screening for M2 activity and inhibitors are: 1) once produced, viral particles are stable and unaffected by M2 cytotoxicity, 2) M2 can be readily captured from the cell surface in its native and functionally-active structure, 3) M2 in viral particles is isolated from endogenous cellular processes that regulate membrane potential and pH, and 4) viral particles are readily adaptable to HTS format, including ultra-high-throughput and miniaturized formats that are difficult to adopt using cells.

Retroviral lipoparticles incorporating M2 are created by co-transfecting HEK-293 cells with one plasmid expressing the murine leukemia virus Gag structural protein, and another plasmid expressing M2 from influenza A/Udorn/72 (Udorn), as outlined herein. Lipoparticles are harvested, purified, and quantified as previously described.

Lipoparticles expressing M2 are suspended in HBS (pH 7.0) containing 1% FMP dye in 384-well microplates. Compounds from a large chemical library of potential inhibitors (Asinex) are then individually added (20 uM, 20 ul final total volume). After 1 h at room temperature, MES buffer pH 4.5 is added to a final concentration of 30 mM, while monitoring fluorescence in real time (Molecular Devices FlexStationII, excitation wavelength 530 nm, emission wavelength 565 nm). A change in fluorescence is observed in wells containing compounds with no inhibitory activity, while wells containing M2 inhibitors report no or minimal change in fluorescence. Separate wells containing known M2 inhibitors (100 uM amantadine, 10 uM rimantadine), inhibitors of other ion channels (e.g. 10 nM CHTX), and no inhibitors are included in quadruplicate on each microplate. As a counter-screen that can provide an independent measure of false-negatives and positives, lipoparticles without M2 (null lipoparticles) and lipoparticles treated with FCCP are also screened with the same library (null lipoparticles do not emit any fluorescent signal, while FCCP-lipoparticles emit an uninhibited fluorescent signal).

Compounds tested in the HTS that significantly block the change in fluorescent signal (more than 3 standard deviations from the uninhibited signal) are considered "hits" and are selected for confirmation and further characterization. Briefly, these "hits" are titrated (100 uM to 1 nM in 3-fold increments and in triplicate) to derive $IC_{50}$ values for M2-lipoparticles, lipoparticles treated with FCCP, and lipoparticles containing a non-specific ion-channel, Shaker (specific compounds do not inhibit other ion channels or ionophores). Hits that are specific for Udorn M2 are then cross-screened against other strains of M2 to identify compounds exhibiting the broadest spectrum of inhibition of M2 variants.

Using alternative M2 expression vehicles (such as other lipoparticles, or native influenza virions), and alternative detection modalities (such as other membrane-sensitive dyes or pH-sensitive proteins) will not alter the fundamental screening process. Similar approaches could be used to screen compound libraries for inhibitors of other viral ion channels.

One skilled in the art would recognize that alternative M2 clones could also be used, including, but not limited to, M2 clones derived from influenza A/HK/156/97 (H5N1), A/Vietnam/1194/04 (H5N1), B/Maryland/1/59, and B/Lee/40. Additional variants may include the most common drug-resistant variants (positions V27, A30, S31, G34) (Abed, et al. (2005), Antimicrob Agents Chemother, 49:556-9, Hay, et al. (1985), Embo J, 4:3021-4).

Example 23

Discovery of Inhibitors of Closed Ion Channels

Lipoparticles are prepared as described previously, by co-transfecting HEK-293 cells with the cDNA for the KCNQ1 ion channel, and a CMV promoter-based plasmid expressing structural components (the Gag protein) of the MLV genome. Lipoparticles are harvested from the culture supernatant, purified, and quantified as described herein, and suspended in a buffer with a $K^+$ concentration approximating that of cell cytoplasm (10 mM Hepes 7.0, 15 mM NaCl, 135 mM KCl). Lipoparticle interiors become equilibrated with this buffer over time (e.g. 1 week). Lipoparticles are then suspended in assay buffer (10 mM Hepes 7.0, 135 mM NaCl, 15 mM KCl, and containing 1% FMP dye) and distributed in 384-well plates using a Biomek FX automated liquid handler. The relative internal and external $K^+$ concentrations of lipoparticles are similar to that of a resting cell, ensuring that KCNQ1 channels are likely to be in the closed configuration. Compounds from a large chemical library of potential inhibitors (Asinex) are then added (20 uM, 20 ul final total volume) and allowed to bind for 1 hour at room temperature. Control (uninhibited) wells receive no compounds. While measuring fluorescence using a Molecular Devices FlexStationII fluorescence microplate reader, $K_2SO_4$ is added to a final $K^+$ concentration of 60 mM. Wells in which the fluorescent signal (indicating $K^+$ translocation) is significantly blocked (more than two standard deviations different from the uninhibited signal) are considered "hits" and are selected for confirmation and further characterization by measuring their IC50.

Example 24

Discovery of Inhibitors of Open Ion Channels

Many drugs bind to ion channels only when the channels are in the open or inactivated states (e.g. most inhibitors of hERG bind only to the pore of the open or inactivated channel (Sanguinetti, et al. (2005), Trends Pharmacol Sci, 26:119-24)), which is difficult to detect using cell-based HTS. Lipoparticles, in which the open and closed states of ion channels can be defined, may thus play a pivotal role in helping reduce off-target drug side-effects. Lipoparticles containing KCNQ1 ion channels are prepared as described herein, and suspended in assay buffer (10 mM Hepes 7.0, 135 mM NaCl, 15 mM KCl), with which the viral interiors are allowed to equilibrate for 1 week. Prior to assay, lipoparticles are suspended in fresh assay buffer (10 mM Hepes 7.0, 135 mM NaCl, 15 mM KCl) containing 1% Molecular Devices' FMP dye, and distributed in 384-well plates using a Biomek FX automated liquid handler. The relative internal and external $K^+$ concentrations of lipoparticles will thus be equimolar, conditions under which most KCNQ1 channels are expected to be open (or inactivated over time). Compounds from a large chemical library of potential inhibitors (Asinex) are then added (20 uM, 10 ul final total volume) and allowed to bind for 1 hour at room temperature. Control (uninhibited) wells receive no compounds. While measuring fluorescence in real time using a Molecular Devices FLIPR-Tetra fluorescence microplate reader, $K_2SO_4$ is added to a final $K^+$ concentration of 60 mM. Wells in which the fluorescent signal (indicating $K^+$ translocation) is significantly blocked (more than two standard deviations different from the uninhibited signal) are considered "hits" and are selected for confirmation and further characterization by measuring their IC50.

Example 25

An Array of Cardiac Ion Channels

Ion channels involved in the cardiac action potential are validated disease targets and are implicated in off-target adverse drug effects. Here, five ion channel combinations (Table 3) that have been implicated in over 95% of inherited and drug-induced cardiac arrhythmias are incorporated into lipoparticles, as previously described, for screening of potential inhibitors. Incorporation of individual ion channel $\alpha$-subunits into lipoparticles allows inhibitors specific to a given protein to be identified. However, the ability to also evaluate assembled ion channel $\alpha+\beta$ subunits is potentially important for a drug screen. For example, compounds that differentiate between KCNQ1 and the naturally occurring KCNQ1–minK complex have been described (Tristani-Firouzi, et al. (2003), J Mol Cell Cardiol, 35:27-35). Briefly, HEK-293 cells are transiently co-transfected with a plasmid coding for the MLV Gag structural protein, and either one (KCNQ1, hERG, SCN5A) or two (KCNQ1+minK, hERG+MiRP1) mammalian expression vectors containing specific ion channel cDNAs. To ensure maximum sensitivity of inhibition, lipoparticles containing the minimum number of ion channels required for membrane depolarization are determined by titrating the amount of each ion channel plasmid used for transfection. After harvest and purification, lipoparticles are suspended in, and allowed to equilibrate with (48 hours, room temperature) buffers that 'prime' their incorporated ion channels into either "closed" (10 mM Hepes 7.0, 15 mM NaCl, 135 mM KCl) or "open" (10 mM Hepes 7.0, 135 mM NaCl, 15 mM KCl) conductance states during assay. After equilibration, lipoparticles are suspended in assay buffer (10 mM Hepes 7.0, 135 mM NaCl, 15 mM KCl, and containing 1% Molecular Devices' FMP dye). The lipoparticles are arranged in an array format in a 384-well microplate, ready to be tested against inhibitors, as described herein.

TABLE 3

The ion channels responsible for >95% of the cases of familial and drug-induced cardiac arrhythmias will be incorporated into lipoparticles. KCNQ1 (also referred to as KvLQT1) is the protein product of the KCNQ1 gene (KvLQT1), hERG is the protein product of KCNH2, minK the protein product of KCNE1, and MiRP1 the protein product of KCNE2. minK and MiRP1 are beta subunit single-transmembrane proteins that do not conduct ions but regulate ion conduction by their respective partners.

| Ion Channels | Electrophysiology |
|---|---|
| KCNQ1 | Voltage-gated ($K^+$) |
| KCNQ1 + minK | Voltage-gated ($K^+$), $I_{Ks}$ |
| hERG | Voltage-gated ($K^+$) |
| hERG + MiRP1 | Voltage-gated ($K^+$), $I_{Kr}$ |
| SCN5a | Voltage-gated ($Na^+$), $I_{Na}$ |

Example 26

Detection of Drugs that Block hERG Activity

Here, drugs capable of modifying the activity of the hERG $K^+$ channel are identified by HTS, and confirmed by subsequent IC50 determination. Lipoparticles containing hERG, and lipoparticles containing hERG+MiRP1, are produced, as described herein. For each ion channel type, one set of lipoparticles is equilibrated with "closed-state buffer" (10 mM Hepes 7.0, 15 mM NaCl, 135 mM KCl), and one with "open-state buffer" (10 mM Hepes 7.0, 135 mM NaCl, 15 mM KCl) for 48 hours at room temperature, as described herein. Lipoparticles are then added to inhibitory compounds (20 uM final concentration). After re-suspension in assay buffer (10 mM Hepes 7.0, 135 mM NaCl, 15 mM KCl, and containing 1% Molecular Devices' FMP dye), lipoparticles are distributed across 384-well microplates using a Biomek FX automated liquid handler, and a large library of potentially inhibitory compounds (Asinex) are added to a final volume of 20 ul. Control (uninhibited) wells receive no compounds. After 1 hour at room temperature, fluorescence is measured using a Molecular Devices FLIPR-Tetra fluorescence microplate reader, while $K_2SO_4$ is added to a final $K^+$ concentration of 60 mM. Wells in which the fluorescent signal (indicating $K^+$ translocation) is significantly blocked (more than 2 standard deviations different from the uninhibited signal) are considered "hits". As an independent measure of false-negatives and positives, lipoparticles without any specific ion channel (null-lipoparticles, which should demonstrate no fluorescent signal) and null-lipoparticles pre-treated with the $K^+$ ionophore valinomycin (which should exhibit a fluorescent signal that is not chemically inhibited) are also screened (separately) with the same library.

Compounds identified in the HTS as significant inhibitors of hERG function are confirmed and further characterized by determination of $IC_{50}$. Briefly, each compound is titrated (100 uM to 1 nM in 3-fold increments and in triplicate) against a constant concentration of hERG-lipoparticles, hERG+MiRP1-lipoparticles, null-lipoparticles, and valinomycin-treated null-Lipoparticles.

Example 27

Detection of Ion Channel Activity in Lipoparticles by Electrical Stimulation

Here we detect ion channel activity in Lipoparticles using electrical impulses to stimulate the opening of channels within Lipoparticles. Analogous methods have been used to detect ion channel activity within cells (Burnett, et al. (2003), J Biomol Screen, 8:660-7)(Vertex, Inc. VIPR and E-VIPR). The voltage-gated ion channel Shaker is incorporated into Lipoparticles which are resuspended in a high $K+$ concentration buffer (10 mM Hepes 7.0, 15 mM NaCl, 135 mM KCl) and allowed to equilibrate, as described herein. The Lipoparticles are mixed with 1% FMP-Blue dye and placed in a 96-well microplate in a low $K+$ buffer (10 mM Hepes 7.0, 135 mM NaCl, 15 mM KCl). The buffers mimic the normal physiological balance of $Na+$ and $K+$ across the cell membrane. A different test compound is added to each well of the microplate to test its effect on the ion channel. 10 nM Charybdotoxin is included as a control in two wells of the microplate. Each well of the microplate is then electrically stimulated using a computer controlled electrode array (E-VIPR, Vertex, Inc.) integrated with a fluorescence plate reader (Huang, et al. (2006), Nat Biotechnol, 24:439-46) The electrical stimulation (rather than a change in $K+$ concentration) opens voltage-gated ion channels. If Shaker is capable of opening and conducting ions, the emission of the FMP fluorescent dye will change in intensity as a membrane potential is established by $K+$ translocation. If a drug blocks the ability of Shaker to open, no fluorescent change will be measured. One skilled in the art would recognize that alternative electrical stimulation devices could also be used, as well as combinations of $Na+$ and $K+$ channels for repetitive electrical field stimulation, as well as alternative reporter dyes (such as FRET pairs) and fluorescence detection methods.

Example 28

Detection of Ion Channel Activity in Lipoparticles by Radioactive Ion Efflux

Here we detect ion channel activity in Lipoparticles using radiolabeled ions to detect the activity of ion channels within Lipoparticles. Analogous methods have been used to detect ion channel activity within cells (Birch, et al. (2004), Drug Discov Today, 9:410-418, Cheng, et al. (2002), Drug Dev Ind Pharm, 28:177-91). The ion channel hERG is incorporated into Lipoparticles and resuspended in low $K+$ buffer (10 mM Hepes 7.0, 135 mM NaCl, 15 mM KCl) and allowed to equilibrate, as described herein. The Lipoparticles are placed in a 96-well microplate in the same low $K+$ buffer but also containing radioactive rubidium (86Rb). A different test compound is added to each well of the microplate to test its effect on the ion channel. The hERG ion channel is then stimulated by the addition of high $K+$ (60 mM final). $K+$ and 86Rb+ will enter the Lipoparticle while the ion channel is open. The Lipoparticles are then isolated by washing the wells with low $K+$ buffer through GF/C filter plates (pre-treated with 0.1% polyethyleinamine). The Lipoparticles will bind to the GF/C filter while free 86Rb+ will pass through the filter. The filters are then counted for radioactivity as an indication of how much Rb+ has been transported into the Lipoparticles by the hERG ion channels. Lipoparticles without hERG will serve as negative controls. One skilled in the art would recognize that other types of ion detection could be used, such as atomic absorption (Aurora Biomed ICR). One skilled in the art would also recognize that other types of radioactive ions could be used depending on the ion channel, including radioactive $Na+$ and $Ca++$.

Example 29

Detection of hERG Ion Channel Function in VLPs

The hERG ion channel can be incorporated within retroviral VLPs, its $K^+$-translocating function detected, and chemical inhibition of this function quantitatively monitored. VLPs were produced as described ((Doranz, et al. (2004)) U.S. patent application Ser. No. 10/901,399, incorporated by reference herein), using MLV Gag and hERG under the control of CMV promoters. Successful incorporation of the hERG channel was determined by Western Blot, after separation of lysed VLPs by SDS-PAGE, using a mouse monoclonal anti-HA antibody and an HRP-conjugated anti-mouse monoclonal secondary antibody (FIG. 20). An approximately 155 kDa-sized band was detectable in HA-hERG VLPs, and in lysed 293T cells expressing HA-hERG (positive control). No protein bands were observed in negative controls, which comprised VLPs containing hERG (without HA) and 293T cells expressing hERG (without HA).

To demonstrate that hERG incorporated within VLPs is functional, hERG or HA-hERG VLPs were suspended in buffer (10 mM Hepes 7.0, 135 mM NaCl, 15 mM KCl, and containing 1% Molecular Devices' FMP dye), and aliquotted to wells of a 384-well microplate. A FlexStation II microplate reader (Molecular Devices) was programmed to automatically and simultaneously inject $K_2SO_4$ to a final concentration of 30 mM in each well, and to measure fluorescence at 2 sec intervals starting 30 sec before the addition of $K^+$ (FIG. 21). Fluorescence was observed to increase to a maximum within 2 seconds of the addition of $K^+$, and was maintained through the entire 180-second observation period. No response was observed when $K_2SO_4$ was substituted with buffer alone (10 mM Hepes) or buffer with 60 mM NaCl. Incubation of VLPs for 1 hour at room temperature with the selective hERG inhibitor, E4031, prior to the addition of $K_2SO_4$, abrogated the increase in fluorescence intensity, demonstrating the specificity of $K^+$ transportation by hERG in these VLPs. The potency with which E4031 was able to inhibit hERG activity in the VLPs was quantitatively determined after pre-incubation for 1 hour at room temperature with E4031 at a range of concentrations (0.0001, 0.001, 0.01, 0.1, 1.0, 10, 100 µM). An inhibition curve was generated by plotting the mean change in fluorescence (corrected for baseline values) following the addition of $K_2SO_4$ against the log of the Molar concentration of E4031 in each well (FIG. 22). E4031 was able to inhibit the translocation of $K^+$ ions in VLPs incorporating hERG with a potency (IC50) of 2.33 uM E-4031.

Example 30

Detection of 5HT3a Ion Channel Function in VLPs

The function of 5HT3a, a ligand-gated cation channel, can be detected in VLPs. VLPs were produced as described ((Doranz, et al. (2004)) U.S. patent application Ser. No. 10/901,399, incorporated by reference herein), using MLV Gag and 5HT3a under the control of CMV promoters. VLPs containing the 5HT3a protein were suspended in 10 mM Hepes containing 50 µM serotonin and 1% FMP blue dye (Molecular Devices). VLPs were aliquotted into triplicate wells of a 384-well microplate ($5 \times 10^6$ DLS counts/sec per well), and fluorescence (565 nm) monitored in a FlexStation II (Molecular Devices) while NaCl (0-150 mM final concentration) was simultaneously added to each well. A substantial increase in mean fluorescence intensity (compared with baseline values) was observed in wells to which 75 mM NaCl or more had been added, and this appeared to be concentration dependent. No change in fluorescence intensity was noted in those wells to which no NaCl (buffer alone) was added. Demonstrating the specificity of 5HT3a-mediated $Na^+$ transport in these VLPs, omission of the ion channel ligand, serotonin, from the assay mix resulted in no change in fluorescence intensity. Tubocurarine (5 µM), a non-selective inhibitor of ion channel function, was able to inhibit the fluorescent signal associated with $Na^+$ transport by VLP-incorporated 5HT3a.

Example 31

Detection of Ion Channel Function in Intact Baculovirus Particles

Ion channels, such as the hERG $K^+$ ion channel, can be incorporated, and their function monitored, in other enveloped viruses as well, such as baculovirus. A recombinant baculovirus expressing the human hERG protein (with an HA tag), was created using Invitrogen's Bac-to-Bac kit followed by Cellfectin transfection of HA-hERG bacmid into Sf9 cells. Baculovirus particles were grown and then purified by 0.45 um filtration followed by two ultracentrifugations across sucrose cushions (29,000 rpm, 4° C., 1.5 hr, 20% sucrose). The incorporation of hERG into purified baculovirus was confirmed by Western blot, using mouse anti-HA monoclonal antibody, and HRP-conjugated anti-mouse IgG monoclonal secondary antibody (FIG. 24). Similarly, other multiple-spanning membrane proteins, such as the G protein-coupled receptor CXCR4, were also incorporated into recombinant baculovirus, purified, and shown to be incorporated by western blot (not shown).

The ion-transporting function of baculovirus-incorporated hERG was monitored by $K^+$ flux assay. Briefly, purified baculovirus were suspended in buffer (10 mM Hepes 7.0, 135 mM NaCl, 15 mM KCl, and containing 1% Molecular Devices' FMP dye), and aliquotted to wells of a 384-well black-walled, clear-bottom microplate. Fluorescence was monitored using a FlexStationII microplate reader as $K_2SO_4$ was simultaneously added to all wells, to a final concentration of 30 mM. Fluorescence intensity was recorded every 2 seconds for 180 seconds. The change in fluorescence was calculated by subtracting the mean fluorescence of the first 30 seconds of recording (baseline) from the mean fluorescence of the final 30 seconds of recording (maximum). An increase in fluorescence was observed in wells containing hERG baculovirus in which $K_2SO_4$ was added (FIG. 25A). Control wells that did not receive $K_2SO_4$ (Hepes buffer alone) did not respond. No substantial change in fluorescent signal following the addition of $K_2SO_4$ was observed from baculovirus incorporating a non-ion channel protein (the chemokine receptor CXCR4). These data suggest that that the fluorescent signal being observed is due to the specific transportation of $K^+$ across the baculoviral membranes by the incorporated hERG ion channel. Further evidence of this is provided by the abrogation of fluorescent signal by the selective hERG inhibitor, E4031. Pre-incubation of hERG baculovirus with E4031 (1-300 µM) for 1 hour at room temperature, prior to the addition of $K_2SO_4$, inhibited fluorescence intensity in a concentration-dependent fashion (FIG. 25B).

Example 32

Detection of Ion Channel Activity in Intact Influenza Virions

The function of the influenza virus $H^+$ ion channel, M2, can be detected in intact Influenza A virions using a lipid-soluble dye that is sensitive to changes in membrane potential. PR8/34 strain influenza A virions were grown and purified from embryonated chicken eggs, as described previously (Zhang, et al. (2000), J Virol, 74:4634-44). Virions were suspended in 10 mM HEPES pH 7.0, containing 150 mM NaCl and 0.4% FMP dye (Molecular Devices) and aliquotted in wells of a 384-well plate at titers ranging from $1.0 \times 10^6$-$7.5 \times 10^6$ DLS counts/sec per well. Fluorescence (530/565 nm excitation/emission) was monitored using a FlexStationII, while MES buffer pH 4.5 was simultaneously added to each well to a final concentration of 30 mM. An increase in fluorescence signal (corrected for baseline values), indicating a change in the membrane potential as $H^+$ ions were transported by M2, was observed, and was positively correlated to the amount of PR8/34 virions in each well (FIG. 26). MLV retroviral lipoparticles which did not contain an M2H$^+$ ion channel showed no such change in fluorescence ('Null' control). $H^+$ ions could, however, be transported across the membranes of retroviral particles by prior treatment with the protonophore FCCP. Collectively, these data suggest that the movement of $H^+$ across influenza particle membranes is due to the active function of the M2 ion channel.

Example 33

Detection of Diverse Influenza M2 Ion Channels after Incorporation in MLV-based VLPs Functional influenza M2H$^+$ channels can be incorporated into various virus-like particles, and their activity and inhibition monitored. M2 ion channels from a number of influenza A and B strains, including A/M2 Udorn 72, B/M2 Lee 40, and A/M2 HK 156/97, each containing a C-terminal V5 epitope tag, were cloned by gene synthesis (Blue Heron Biotechnology, Bothwell Wash.). Retroviral VLPs were produced using MLV Gag, and one each of the M2 genes, under control of the CMV promoter, as described ((Doranz, et al. (2004)) U.S. patent application Ser. No. 10/901,399, incorporated by reference herein). Successful incorporation of each 17 kDa M2 ion channel was confirmed, after lysing VLPs and separating proteins by reducing PAGE, by Western blot analysis, using a mouse anti-V5 monoclonal primary antibody, and an HRP-conjugate anti-mouse monoclonal secondary antibody (FIG. 27).

The functional activity of M2 ion channels incorporated in retroviral VLPs was determined by $H^+$ flux assay. VLPs were suspended in 10 mM HEPES pH 7.0 containing 150 mM NaCl and 1.0% FMP blue membrane potential dye (Molecular Devices), and aliquotted in wells of a 384-well plate (2.5-$5\times10^{6}$ DLS counts/sec per well). Fluorescence (530/565 nm excitation/emission) was monitored using a FlexStationII microplate reader (Molecular Devices) during the addition of MES buffer pH 4.5 to a final concentration of 30 mM. An increase in raw fluorescence intensity indicated transportation of $H^+$ across the membranes of VLPs in which M2 had been incorporated, but not across the membranes of VLPs without M2 (FIG. 28). Prior treatment of VLPs for 1 hour at room temperature with the selective M2 inhibitors amantadine (100 μM), or rimantadine (10 μM), abrogated the subsequent movement of $H^+$ across viral membranes, only in VLPs incorporating M2 channels from influenza strains sensitive to these drugs (A/M2 Udorn72, FIG. 28 and FIG. 29B; A/M2 HK156/94 FIG. 29A and FIG. 29C). These drugs exerted no effect on the transport of $H^+$ across VLP membranes incorporating M2 channels from influenza strains resistant to amantadine and rimantadine (A/M2 PR8, FIG. 29A; B/M2 Lee40, FIG. 29B; A/M2 VN1194, FIG. 29C). Furthermore, VLPs which incorporated a mutant of A/M2 PR8/34 (V27S31), rendering it (abnormally) sensitive to amantadine, could transport $H^+$ in the absence, but not in the presence of 100 μM of the drug (FIG. 29A). Incorporation of the N31S substituted mutant of A/M2 Udorn72 (Udorn is usually an amantadine-sensitive variant of M2), rendered $H^+$ transport across VLPs resistant to inhibition by amantadine (FIG. 29B). Collectively, these data confirm that the movement of $H^+$ across VLP membranes is due solely to the activity of incorporated functional M2 proteins.

The potency with which amantadine and rimantadine were able to inhibit $H^+$ transportation by M2 proteins incorporated in retroviral VLPs was quantitatively estimated from the IC50 of each drug. VLPs incorporating A/M2/HK156/94 were suspended in 10 mM HEPES pH 7.0 containing 150 mM NaCl and 1.0% FMP blue membrane potential dye (Molecular Devices). VLPs were then aliquotted in wells of a 384-well plate (2.5-$5\times10^{6}$ DLS counts/sec per well) containing amantadine (0, 0.001, 0.01, 0.03, 0.1, 0.2, 0.4, 1.0, 2.0, 4.0, 10.0 or 30.0 uM) or rimantadine (0, 0.001, 0.002, 0.004, 0.01, 0.02, 0.04, 0.1, 0.2, 0.4, 1.0, 2.0, 4.0, or 10.0 uM), and left at room temperature for 1 hour. Fluorescence (530/565 nm excitation/emission) was then monitored in triplicate wells, using a FlexStationII microplate reader, during the addition of MES buffer pH 4.5 simultaneously to each well to a final concentration of 30 mM. Raw fluorescence intensities were corrected for baseline values. Inhibition curves for amantadine and rimantadine were generated by plotting the mean change in fluorescence against the log of the drug concentration (Molar) in those wells. Amantadine was able to inhibit the translocation of $H^+$ ions in VLPs incorporating A/M2 HK156/97 with a potency (IC50) of 0.98 μM (Hillslope=−0.71) (FIG. 30). Rimantadine inhibited transmembrane $H^+$ movement in the same VLPs with a potency (IC50) of 0.18 μM (Hillslope=−1.1). These values correspond well with those reported in the literature (and calculated using other measures of M2 function, such as plaque assay), in which the IC50 of amantadine is in the range of 1-10 μM, with rimantadine being approximately 10-times more potent (Fischer, et al. (2002), Biochim Biophys Acta, 1561:27-45). As expected, neither drug was capable of preventing $H^+$ movement across membranes of VLPs pre-treated with the protonophore FCCP, demonstrating the specificity with which drug inhibition of M2 activity was able to be monitored.

To determine the utility of the ion channel assay described here for high-throughput identification of potential inhibitors (i.e. drugs), we calculated the Z'-factor, an often-used, unitless statistical measure of the signal-to-noise and reproducibility of an assay (Zhang et al., 1999), for the amantadine and rimantadine inhibition assays of M2 activity in VLPs. The change in corrected fluorescence intensity associated with the addition of MES buffer in wells not containing any amantadine or rimantadine was 5,894±266 (mean±S.D.). In the presence of 30 μM amantadine, the mean change in fluorescence resulting from MES addition was 314±206. In the presence of 10 μM rimantadine, the mean change in fluorescence was −432±167. These results yield Z'-factors of 0.746 and 0.794, respectively, considered excellent scores for high-throughput screening purposes. A Z'-factor greater than 0.5 is highly desired in high-throughput screening assays. Additional buffers of various pH values (30 mM MES pH 2.83, 3.02, 3.25, 3.35, 3.5, 4.0, 5.0, 5.5; HCl 5 μl of 0.001, 0.005, 0.01, 0.025, 0.05, 0.1, 0.3, 1.0 N; Citrate buffer 5 μl of 50, 100, 150, 200, 300 mM pH 4.5; 30 mM Citrate buffer pH 4.0, 4.5, 5.0, 5.5) were also tested as pH stimulants. Various temperatures were also tested for running the M2 assay, including 4, 23, 25, 30, and 37 degrees Celsius. The function of M2 in VLPs also was not effected by DMSO (up to 5%), a common drug solvent.

Collectively, these results demonstrate the utility of the miniaturized VLP format for high throughput-screening of potential M2 modulators.

The disclosures of each and every patent, patent application, publication, and accession number cited herein are hereby incorporated herein by reference in their entirety. The appended sequence listing is hereby incorporated herein by reference in its entirety.

While this invention has been disclosed with reference to specific embodiments, it is apparent that other embodiments and variations of this invention may be devised by others skilled in the art without departing from the true spirit and scope of the invention.
The appended claims are intended to be construed to include all such embodiments and equivalent variations.

What is claimed is:

1. A method for identifying a test compound that can modulate ion conductance comprising:
   a) contacting an isolated virus particle purified away from a cell, the particle comprising an external lipid bilayer, a viral core protein, and a selected ion conductor with a membrane potential sensitive dye and a test compound; and
   b) detecting a change in membrane potential with the membrane potential sensitive dye,
   wherein a modulation in ion conductance in the presence of the test compound indicates that the test compound modulates ion conductance.

2. The method of claim 1, wherein the selected ion conductor is an ion channel polypeptide or an ionophore.

3. The method of claim 1, further comprising activating the selected ion conductor prior to contacting the particle with the test compound.

4. The method of claim 3, wherein the activating comprises contacting the isolated virus particle with a ligand that binds to the selected ion conductor and activates the selected ion conductor.

5. The method of claim 3, wherein the activating comprises contacting the isolated virus particle with a salt concentration effective to activate the selected ion conductor.

6. The method of claim 1, wherein the detecting a change in membrane potential comprises detecting a change in fluorescence.

7. The method of claim 1, wherein the membrane potential sensitive dye is di-4-ANEPPS, di-8-ANEPPS, rhodamine 421, oxonol VI, JC-1, DiSC3(5), CC2-DMPE, DiSBAC2(3), and DiSBAC4(3), DiSBAC(1)3, FMP-Blue, FMP-Red, VABSC-1, HLB 021-152, HLB 021-155, HLB 007-054, HLB 021-149, HLB 004-111, HLB 007-052, HLB 028-008, HLB 004-078, HLB 004-183, and combinations thereof.

8. The method of claim 2, wherein the ion channel polypeptide is hERG, SCN5a, KCNQ1+minK, hERG+MiRP1, M2, 5HT3a, Shaker, KCNQ2+KCNQ3 and KCNQ1, and combinations thereof.

9. The method of claim 1, wherein the viral core protein is an influenza core protein, HIV core protein, SIV core protein, MLV core protein, EIAV core protein, RSV core protein, VSV core protein, ALV core protein, or baculovirus core protein.

10. The method of claim 2, wherein the ion channel polypeptide is a viral ion channel polypeptide or a non-viral ion channel polypeptide.

11. The method of claim 10, wherein the non-viral ion channel polypeptide is a eukaryotic ion channel polypeptide.

12. The method of claim 1, wherein the modulation is inhibition or activation.

13. The method of claim 1 further comprising comparing the test compound's ability to modulate an ion conductor's activity to a compound known to modulate an ion channel conductor's activity.

14. The method of claim 13, wherein the compound known to modulate an ion channel conductor's activity is amantadine or rimantadine.

15. The method of claim 1, wherein the isolated virus particle consists of one selected ion conductor.

16. The method of claim 1 further comprising measuring the change in membrane potential.

17. The method of claim 2, wherein the ionophore is a protonophore.

18. The method of claim 2, wherein the ionophore is valinomycin, SQiRP, FCCP, or ionomycin.

19. The method of claim 2, wherein the isolated virus particle comprises the ion channel polypeptide and the ionophore.

20. The method of claim 1, wherein the virus particle is a virus-like particle.

21. The method of claim 2, wherein the virus particle is a virus-like particle.

* * * * *